US007220261B2

(12) United States Patent
Truckai et al.

(10) Patent No.: US 7,220,261 B2
(45) Date of Patent: May 22, 2007

(54) ELECTRICAL DISCHARGE DEVICES AND TECHNIQUES FOR MEDICAL PROCEDURES

(75) Inventors: Csaba Truckai, Saratoga, CA (US); John H. Shadduck, Tiburon, CA (US)

(73) Assignee: Sciogen, Inc., Saratoga, CA (US)

( * ) Notice: Subject to any disclaimer, the term of this patent is extended or adjusted under 35 U.S.C. 154(b) by 0 days.

(21) Appl. No.: 11/065,180

(22) Filed: Feb. 23, 2005

(65) Prior Publication Data

US 2006/0058782 A1   Mar. 16, 2006

Related U.S. Application Data

(63) Continuation of application No. 10/282,555, filed on Oct. 28, 2002, now Pat. No. 6,890,332, which is a continuation-in-part of application No. 09/614,163, filed on Jul. 11, 2000, now abandoned, which is a continuation-in-part of application No. 09/317,768, filed on May 24, 1999, now abandoned.

(51) Int. Cl.
*A61B 18/18* (2006.01)

(52) U.S. Cl. .................................. 606/41; 607/101
(58) Field of Classification Search ................ 128/898; 606/41, 46, 5; 607/101, 114; 600/437, 439, 600/466
See application file for complete search history.

(56) References Cited

U.S. PATENT DOCUMENTS

| 5,281,217 A * | 1/1994 | Edwards et al. ............... 606/41 |
| 5,873,855 A | 2/1999 | Eggers et al. |
| 5,888,198 A | 3/1999 | Eggers et al. |
| 5,891,095 A | 4/1999 | Eggers et al. |

(Continued)

OTHER PUBLICATIONS

Tucker et al., "Histologic Characteristics of Electrosurgical Injuries", *Journal Am. Assoc. Gyneco. Laproscopy*, 4 (2), pp. 201-206, 1997.

(Continued)

*Primary Examiner*—Rosiland Rollins
(74) *Attorney, Agent, or Firm*—Townsend and Townsend and Crew LLP

(57) ABSTRACT

A medical instrument coupled to first and second energy means and a computer controller for the controlled volumetric removal of thin tissue layers. The system provides a source for introducing a gas to controllably form and capture transient gas volumes in a microchannel structure at the working surface of the instrument that interfaces with a targeted tissue site. Each of the microchannel features of the working surface carries an electrode element coupled to the electrical source. The energy may be applied to the targeted site in either of two modes of operation, depending in part on voltage and repetition rate of energy delivery. In one mode of energy application, electrical potential is selected to cause an intense electrical arc across the transient ionized gas volumes to cause an energy-tissue interaction characterized by tissue vaporization. In another preferred mode of energy delivery, the system applies selected levels of energy to the targeted site by means of an energetic plasma at the instrument working surface to cause molecular volatilization of surface macromolecules thus resulting in material removal. Both modes of operation limit collateral thermal damage to tissue volumes adjacent to the targeted site. Another preferred embodiment provides and an ultrasound source or other vibrational source coupled to the working end to cause cavitation in fluid about the working end.

17 Claims, 38 Drawing Sheets

U.S. PATENT DOCUMENTS 5,989,248 A * 11/1999 Tu et al. .................. 606/41
6,024,733 A    2/2000 Eggers et al.
6,032,674 A    3/2000 Eggers et al.
6,066,134 A    5/2000 Eggers et al.
6,394,956 B1   5/2002 Chandrasekaran et al.

OTHER PUBLICATIONS

Kim et al, "Optical Feedback Signal for Ultra Short Pulse Ablation of Tissue," *Appl. Surface Sci.* 127-129(1998) pp. 857-862.

* cited by examiner

ELECTRICAL DISCHARGE DEVICES AND TECHNIQUES FOR MEDICAL PROCEDURES

CROSS-REFERENCES TO RELATED APPLICATIONS

This application is a continuation of U.S. patent application Ser. No. 10/282,555, filed Oct. 28, 2002 now U.S. Pat. No. 6,890,332, which was a continuation-in-part of U.S. patent application Ser. No. 09/614,163, filed Jul. 11, 2000, titled Electrical Discharge Devices and Techniques for Plasma-Assisted Skin Resurfacing, now abandoned which was a continuation-in-part of U.S. patent application Ser. No. 09/317,768, filed May 24, 1999, titled Photoionized Gas Enabled Electrical Discharge Technique for Plasma-Mediated Cold Tissue Ablation, now abandoned the full disclosures which are incorporated herein by reference.

BACKGROUND OF THE INVENTION

1. Field of the Invention

The invention is related to electrosurgical instruments and techniques for precision application of energy to tissue, and more particularly to a system for thin layer ablation. More in particular, the working surface of a probe carries (i) delivery means for introducing and capturing a gas volume in a microchannel structure at an interface between the probe and the targeted site, (ii) energy delivery means for creating an intense electrical field of micron-dimensioned gas volumes to controllably apply intense energy to the targeted site to cause volumetric tissue removal, and (iii) vibration means for assisting in the creation of micron-scale gas volumes or bubbles.

2. Description of the Background Art

Various electromagnetic and acoustic energy delivery sources have been investigated for surgical tissue ablation or removal, including radiofrequency (Rf) current flow within tissue, high intensity focused ultrasound (HFU) tissue interactions and microwave energy absorption in tissue. In general, at high intensities, the above listed energy sources generate thermal effects that can vaporize tissue as the means of tissue ablation or removal. In other words, the energy sources elevate the temperature of water in intra- and extracellular spaces to above 100° C. thereby explosively vaporizing water to damage or destroy the tissue. The drawback to such purely thermally-mediated ablations is significant collateral damage to tissue volumes adjacent to the targeted site. While in many surgical fields, the above-described collateral thermal damage may be acceptable, in fields such where thin layer ablations are required, such as skin resurfacing, ophthalmology, neurology, and interventional cardiology, there is a need to prevent, or limit, any such collateral damage.

Lasers for Use in Tissue Ablation. Various laser systems have been developed for tissue ablation. The conventional long-pulse laser systems outside the UV range, wherein long-pulse is defined as a system operating in a range of 10's of nanoseconds to microseconds in pulse duration, have been found to be inefficient in volumetric tissue removal without causing extensive collateral damage. In a the conventional long-pulse laser system (e.g., Nd:YAG, Er:YAG, IR lasers), the photonic energy delivered to a targeted site does not directly disrupt the molecular integrity of surface layers of the site, but rather the energy is transferred into surrounding tissue volumes as photothermal energy, or photomechanical energy. These collateral effects propagate through surrounding tissues as heat, and perhaps mechanical shock waves, which manifest themselves as undesirable collateral damage. More specifically, the generally accepted model of volumetric ablation or removal with lasers having a pulse longer than tens or hundreds of picoseconds is described as follows: The energy absorption is chromophore dependent (and/or scattering dependent), and the energy transfer involves the heating of conduction band electrons by the incident beam of coherent photons which is followed by transfer of thermal energy to the structure's lattice. Ablation or damage occurs by conventional heat deposition resulting in vaporization, melting, or fracture of the structure. The rate of volumetric structure removal depends on thermal conduction through the structure lattice and its thermodynamic properties (heat capacity, heat of vaporization, heat of fusion, etc.). Thus, the minimum energy requirements to cause an ablation effect in the structure's properties may be defined by a threshold of incident laser energy per unit of structure volume at the target site, which threshold is directly dependent on pulse duration. It has been found that ablation thresholds generally require relatively long pulse durations, which in turn are the source of undesirable collateral photothermal (or photomechanical) damage.

In certain tissue ablation fields (e.g., corneal ablation in ophthalmology), excimer lasers have been developed that emit high intensity pulses of ultraviolet (UV) light, typically with pulse durations in the 1 ns to 100 ns range. The short wavelengths, as well as sequenced nanosecond pulse regimes, define a substantially non-thermally mediated form of tissue ablation. Short wavelength UV photons are highly energetic and when radiated onto biological tissue can directly break the chemical bonds in surface layer molecules of the tissue. As a consequence, UV excimer lasers can vaporize or breakdown a surface tissue layer with minimal thermal energy transfer to underlying (or adjacent) tissue volumes. The by-product of the breakdown is predominantly a gas that is ejected away from the surface on which the energy was deposited, thus generally leaving the subsurface layer free from substantial collateral thermal damage. Tissue ablation with UV irradiation with can be controlled depth-wise since biological tissues exhibit strong absorption in the UV region of the electromagnetic spectrum (e.g., at c. 1.93 $\mu$m). In biological tissue, UV radiation typically only penetrates to a depth of from about 0.25 $\mu$m to about 4.0 $\mu$m per pulse in the ns duration pulses described above. Thus, to ablate to a certain depth, the system uses a pre-determined number of pulses of ns energy delivery While UV photonic energy delivery can reduce collateral damage in tissue ablation, there are numerous disadvantages that limit the applicability of UV lasers to biomedical procedures. First, UV photonic energy delivery cannot be easily delivered to a targeted site of a body structure in a fluid environment (e.g., thrombus in a blood vessel) since intervening fluid may absorb energy rather than the target site. For this reason, UV energy delivery is most useful for ablating tissue surfaces exposed to the atmosphere, such as a patient's cornea in a LASIK procedure. Second, the desired lack of collateral damage in UV ablation is known to occur when a single pulse of UV photonic energy irradiates a tissue surface. However, when the UV pulse repetition rate exceeds about 5 to 10 Hz, considerable photothermal collateral damage (as well as photomechanical collateral damage) has been observed. Thus, UV ablation generally may result in low volumetric removals of tissue surfaces per unit of time. Third, while UV photons carry sufficient energy to directly break chemical bonds in surface molecules of tissue, UV wavelengths also may be sufficiently energetic to promote mutagenic effects thus elevating concerns about the long-term health and health of the clinician and the patient.

Conventional Electrosurgical Ablation of Tissue Volumes. Radiofrequency currents in tissue have been known for many years in the prior art for cutting a tissue mass, or for coagulating regions within a tissue mass. Conventional electrosurgical systems known in the art ablate tissue by applying an electrical field across the tissue to be treated. The actual energy-tissue interaction in Rf cutting is typically described in terms of a voltage differential that causes a spark or arc across a gap between an active electrode 2a and the targeted site (e.g., coupled to a return electrode 2b) as shown in FIG. 1A. In the prior art instrument of FIG. 1A, a high energy density capable of tissue cutting is created when the gap between the active electrode 2a and the tissue surface is occupied with an electrically non-conductive gas, or an electrically insulative liquid. FIG. 1A depicts a typical ablation modality in which electrode 2a is moved into contact with a liquid or moisture layer on an exposed tissue mass which vaporizes a plurality of random bubbles 3. The bubbles comprise insulative gas volumes and randomly can form a momentary insulative physical gap between the active electrode 2a and the tissue (coupled to return electrode 2b) resulting in a spark across the gap. Such an Rf spark created between the active electrode and the tissue will cause localized damage and ablation at the discharge conduction site at the surface of the tissue. In other words, the spark causes very high energy densities at the random location that the tissue interfaces the bubble 3 which in turn results in intense heat that disrupts and ablates a site on the tissue surface. In FIG. 1A, it can be seen that conductive paths 4 indicate the paths of current flow. The conventional electrosurgical ablation of FIG. 1A generally is achieved at frequencies ranging from 500 kHz to 2.5 MHz, with power levels ranging from 75 to 750 W. In such prior art tissue cutting with Rf currents, the current density rapidly decreases with distance from the exact energy deposition site on the tissue which is contacted by the spark. Still, the depth of tissue disruption and damage in such prior art electrosurgical cutting may range from about 0.3 mm. to as much as 3.5 mm. (see R. D. Tucker et al, *Histologic characteristics of electrosurgical injuries, Journal Am. Assoc. Gynecol. Laparoscopy* 4(2), pp. 201-206 1997.) The depth of tissue ablation depends on several variables, including (i) the conductivity of the tissue, (ii) the insulative characteristics of the media in the physical gap between the active electrode(s) and the tissue; (iii) the dimension of the physical gap between the electrode(s) and the tissue; (iv) the power setting and optional feedback control of the power level based upon electrical characteristics of the targeted tissue; (v) and the translation of the working end relative to the tissue.

Electrosurgcal Ablation with the Coblator™ System. A recently commercialized invention in the field of electrosurgical ablation was invented by Eggers et al and is a called Coblator™ system (see. e.g., disclosures of Eggers et al in U.S. Pat. Nos. 5,873,855; 5,888,198; 5,891,095; 6,024,733; 6,032,674; 6,066,134 and the companion patents cited therein). The Coblator™ system relies on the creation of a voltage difference between a plurality of closely spaced rod-like electrode elements 2a and a return electrode 2b (see FIG. 1B) wherein the working end carries both the active and return electrodes. The Coblator™ system differs from conventional electrosurgical devices in that the system introduces an electrically conductive fluid such as isotonic saline 5 into the physical gaps 6 between the closely spaced active electrodes, and between the electrode group and the targeted tissue. The system applies electrical energy with a frequency of about 100 kHz and a voltage of about 100 to 300 V.

The Coblator™ company promotional materials explain that at high voltage levels, the electrically conductive fluid 5 in the gaps 6 that intervene between the closely spaced active electrodes 2a is converted into an ionized vapor or plasma. As evidence of the character of such a plasma, studies have shown that a typical plasma has an orange glow. Spectroscopic analysis of Coblator emissions show an emission peak of around 590 nm which is characteristic of the sodium ionization peak (NaCl normal solution used as conductive fluid), with negligible emissions above 600 mm. The company promotional material claims that conventional electrosurgical ablation yields a continuous spectrum from 490 nm to 900 nm, peaking at around 700 nm.

The supposition underlying the Coblator™ is that the actual energy-tissue interaction produced by the system relates to charged particles in the plasma having sufficient energy to cause dissociation of molecular bonds within tissue structures that come into contact with the plasma. Based on this hypothesis, the accelerated charged particles have a very short range of travel, and the energy-tissue interaction is confined largely to thin surface layers. Further, the supposition is that the energy-tissue interaction is a "cold" process that does not rely on the thermal vaporization of intra- and extracellular fluids to ablate tissue. In this respect, the Coblator™ system has been described as producing an ablation that compares to that of an excimer laser, both of which produce similar ablation by-products—if relying on comparison of spectrographic emission peaks. The energy required to cause molecular break-down of common molecular bonds in tissue is believed to be in the range of 3.0 eV to 5.0 eV or more. Considering the amount of energy utilized by the Coblator™ system to initially and thereafter continually vaporize NaCl from within a saline solution, it raises the question whether the plasma volumes can sustainably provide the energy levels required for true molecular dissociation of compositions in tissue surfaces, as with an excimer laser.

Another hypothesis that explains the Coblator™ ablation process in more mundane. Referring to FIG. 1B, it can be seen that the Coblator™ working end traps conductive fluid 5 within the many gaps 6 between the closely spaces electrode elements. As electrical potential is increased at the electrodes 2a, random and dynamic conductive paths are created to the return electrode 2b from random discharge points on the active electrodes 2a. Such conductive paths essentially comprise a dynamic uncontrolled distribution of NaCl molecules in the fluid, that can be momentarily linked by high energy densities along the conductive path that will, in turn, vaporize such compositions. The result is a frothy environment of random expanding and collapsing bubbles 3 as shown in FIG. 1B. Since the random transient bubbles 5 may comprise a quasi-neutral gas or a substantially insulative gas—thereafter a spark or discharge path 4 can occur along some random routes between the active electrode 2a and the return electrode 2b and within the bubbles 3. As shown in FIG. 1B, when such random insulative bubbles and an electrical spark path 4 occurs with the tissue surface being intermediate to the active and return electrodes, a spark-type energy-tissue interaction will occur that delivers ablative energy to the tissue at any random location that a bubble 3 in the path 4 interfaces the tissue. While FIG. 1B shows two random spark-type events through a frothy gas bubble environment, if this hypothesis were accepted, an actual Coblator™ ablation comprises 1000's of such random and discrete spark-type events per second to cause tissue ablation. According to this hypothesis, the Coblator™ system would produce an energy-tissue interaction much like that of conventional electrosurgical ablation as depicted in FIG. 1A.

This hypothesis easily explains the two observations made by proponents of the Coblator™ that state (i) that spectroscopic analysis of energy delivery within a conductive fluid supports the theory of molecular dissociation, and (ii) that evidence of limited collateral thermal damage (so-called "cold" ablation) must be the result of a molecular dissociation process. First, the spectroscopic analysis of the Coblator™ ablation certainly would show emission peaks for vaporization of the sodium analytes in the fluid, which is a primary sink of the energy applied from the device—which is different from and predominates over any emission peaks from the tissue ablation. The tissue ablation, if the competing hypothesis of a spark-type interaction of FIG. 1B is accurate, would be characterized by energy-to-tissue events that produce mostly water vapor from the vaporization of intra- and extracellular fluids. Such vapor would be rapidly absorbed by the surrounding fluid environment and might not contribute to any emissions that could be observed by spectrographic analysis of the bubbles of vaporized NaCl. Second, FIG. 1B depicts that the random discrete spark-type events that vaporize tissue are brief—occurring in a the very short, random time intervals in which the insulative bubbles are intact. The lifespan of a bubble is likely to have a duration ranging between 100's of ns to 10's of ms. As is well known, for a tissue ablation to be a substantially cold process, the intervals between successive thermal energy delivery events simply must be longer than the thermal relaxation time of the tissue which is dependent of several tissue characteristics. The thermal relaxation time also must take into consideration the boundary conditions. In the Coblator™ process as depicted in FIG. 1B, the thermal relaxation time of any typical tissue is probably in the range of 100's of ns. In addition, the fluid comprises a boundary condition that acts as a tremendous heat sink. Since the location of spark-type energy applications to tissue is random in location and brief in duration, the combination of (i) the thermal relaxation of the tissue, and (ii) the fluid heat sink removing heat from the tissue can easily return the ablated tissue location to a normal temperature before another random spark-type event occurs in a similar location. Thus, the hypothesis of molecular dissociation is not necessary to explain the "coolness" of the ablation depicted in FIG. 1B.

The types of ablation caused by conventional electrosurgical ablation (see FIG. 1A) and the type of ablation caused by the Coblator™ system (see FIG. 1B—no matter the hypothesis selected to explain the Coblator™ energy-tissue-interaction—share several common characteristics. While conventional and the Coblator™ ablations are suitable for many procedures, both types of ablation are caused by totally random events wherein high electrical energy densities vaporize a fluid or elements therein to create an insulative gas or plasma volume that thereafter causes random localization of an energy-tissue interaction that ablates tissue. By the term random localization, it is meant that while the general location of tissue ablation is known for any time interval, the exact location of an ablation event, for example for any interval in the ns range, is unpredictable. As a further explanation, FIG. 2 represents an enlarged view of a portion of the Coblator™ working end of FIG. 1B with a grid in perspective view as the tissue surface. The location at which the gas volume, or plasma, interfaces the tissue surface is random and the application of energy to the surface will be of very low resolution. If each grid of FIG. 2 is between 10 to 20 µm, the lateral distance d between the point of energy emission and the point of highest energy density (herein called the energy deposition or application site) wherein the energy-tissue interaction is localized may as much as 100 to 500 µm from a reference axis x of the working end, or the lateral distance d could be zero. A further graphically depiction of what is meant by the concept of random localization of energy-tissue interactions is shown in FIG. 2. In that Figure, the energy delivery horizon (or perimeter) is indicated at h, by which is meant that, at a ns or ms time-scale, the actual application of energy to the tissue may be localized anywhere in the delivery horizon h, and the location of any such application will be entirely random within this horizon.

Another characteristic common to both conventional electrosurgical ablation (FIG. 1A) and the Coblator™ ablation (FIG. 1B) relates to (i) the random size of and energy contact site and (ii) the random distribution of energy across the localized site of energy contact. FIG. 2 graphically depicts a random energy contact and ejecta e from such energy application being irregularly distributed across the energy deposition site. Since the actual energy application occurs only in a dynamic, frothy, expanding and collapsing vapor bubble environment, it is believed that FIG. 2 somewhat accurately depicts the typical energy distribution. In any event, on a ns or ms time-scale, it is clear that the dimensions and energy distribution characteristics of energy delivery are uncontrolled and random. This is to be contrasted with lasers energy delivery systems in which localization can be precise with a few µm's and energy distribution across the site can be designed as Gaussian (higher energy in center of site) or "top-hat" (even energy distribution across the energy deposition site).

While conventional electrosurgical ablation and Coblator™ type ablations are suitable for various procedures, the following characteristics common to both types of ablation prevent the possibility of more precise ablations with such prior art systems:

(i) the actual energy deposition site is randomly localized instead of precisely localized;

(ii) the energy density across the energy deposition site is random and uncontrolled;

(iii) the conductive path between and energy deposition site and the emission point on an electrode is random;

(iv) the dimensions of the energy deposition site are random and uncontrolled;

(v) the amount of energy applied per unit of surface at an energy deposition site is random;

(vi) the amount of energy applied per time interval at an energy deposition site is uncontrolled;

(vii) the duration of intervals between successive energy applications to a site are random;

(viii) the actual duration of an interval of energy application is random and uncontrolled;

(ix) the conductive or insulative characteristics of media between the active electrode and the targeted site, at a micro-scale, are uncontrolled, (xi) the dimensions, localization, distribution and duration of insulative gas volumes or plasma volumes that facilitate energy delivery are random and uncontrolled; and (xii) the prior art instrument working ends function dramatically differently depending on the axial distance between an electrode surface and the targeted tissue surface, It would be highly desirable to have greater precision in thin layer ablations for microsurgeries, neurology, and precision skin resurfacing for burn debridement or cosmetic purposes. What is needed are systems and methods for selective volumetric removal of body surface layer portions (i) that are precisely controllable; (ii) that do not rely on thermal vaporization effects to ablate tissue; (iii) that can be activated in a controlled mode that ratably removes depths or volume of tissue in a given time interval to provide selective tissue decomposition; (iv) that allow for well-defined post treatment boundaries between layers of tissue decomposition and undamaged layers; (v) that removes surface structure that is exposed to a gas environment or immersed in a fluid environment; (vi) that provide for energy delivery to a patient's body structure via a working end that can be reduced in scale to less than 1 mm. to 3 mm. in diameter for micro-interventional use; and (vii) that utilize a working end that is simple to manufacture and therefore inexpensive and disposable.

BRIEF SUMMARY OF THE INVENTION

The principal objective of the present invention is to provide controlled and precise applications of energy to a thin surface layer of structure in a patient's body to cause volumetric removal of layer portions substantially without collateral thermal damage. More in particular, an instrument working end is adapted (i) to deliver high intensity electrical energy in a preferred modality to create a highly energetic and dynamic microplasmas for causing molecular volatilization of surface macromolecules to remove tissue with microscale precision, or (ii) to optionally deliver a spark-type energytissue interaction (herein termed a conventional electrosurgical ablation modality) but in a novel micro-scale modality to controllably ablate discrete tissue portions.

The novel energy delivery modalities and energy-tissue interactions are based on utilizing either of two novel principles (hereafter defined at times as control principles) in the application of electrical energy to body structures for ablation purposes. The principles may be applied to a system and instrument working surface independently, or preferably in tandem, and are designed to control the numerous factors that to date have been uncontrolled and random in tissue ablations (i.e., the 12 factors listed above at the end of the Section titled Description of the Related Art.

The first control principle relates to bifurcation of a discrete electrical energy delivery event into two components. (i) the provision of electrical potential at an electrode at an intensity level that can ablate tissue with the electrode spaced apart from the targeted site; and (ii) the ms or ns (microsecond or nanosecond) control of conductive the characteristics, or ionization, of selected media in the interface between the electrode and the targeted site. In other words, it is postulated that the selected media can be switched between non-conductive (or insulative) and conductive (or ionized) stated in a controlled and ultrafast manner to advantageously deliver energy to cause a novel energy-tissue interaction. In a subset of this principle, several ionization methods, as well as energy-enhancing means for energizing a plasma, are disclosed-with photoionization being a preferred means.

The second control principle relates to a tremendous reduction in scale, or micronization, of the features of the working surface for the purpose of controllably localizing a large number of discrete energy-tissue interactions, as well as controlling the physical dimensions of plasma volumes. As will be described below, the working surface may be fabricated by semiconductor processing techniques to provide features in the 5 μm to 10 μm range, by which is meant that widely dispersed micron-scale electrode elements may each apply electrical energy to a localized site to provide discrete spaced apart ablation events. Referring to FIG. 4, it is believed that the system and method of the invention can provide the type of resolution of energy application represented in FIG. 4, which depicts a controlled, discrete, localized energy-tissue interaction eti having a micro-scale dimension (FIG. 4 representing a perspective view of a 5 μm to 10 μm grid).

The system is coupled to a computer controller for controlling intervals of energy delivery-both the ionization means and the electrical energy means for the ablation-as well as for optional flows of the selected media. By controlling the duration of intervals of energy applications and the repetition rate in relation to the thermal relaxation time of the targeted surface, it is postulated that the disclosed plasma-assisted tissue removal method will be a substantially cold process, ie., there will be substantially no collateral thermal damage to tissue.

Each pulse, or burst, of energy application in the disclosed ablation process is assisted or enabled by a sequence of distinct plasma formation processes to achieve the operational objectives of the invention, followed by plasma decay intervals. In an initial portion of the process, an ionized gas (plasma) is formed to allow subsequent electrical potential in a spatially-controlled region at the surface layer. In a second portion of the process, an electrical discharge is created in the ionized gas and surface layer thus causing volatilization of macromolecules of the targeted surface layers to remove layer portions. To define the uses of plasmas herein, it is useful to provide the following background. A plasma is a quasineutral (partly ionized) gas having a significant proportion of charged particles relative to neutral particles which may, in an equilibrium state, exhibit collective behavior. Of interest to this invention are non-equilibrium or highly dynamic microplasmas formed proximate to structure in a patient's body to allow for energy transfer to, or deposition of energy within, thin surface layers of structure in a patient's body to remove (ablate) material without transfer of thermal energy. In the lexicon of physicists, a plasma may be defined simply as an ionized gas, to distinguish it from ordinary or neutral gases. In a neutral gas, each gas atom carries the same number of negatively charged electrons orbiting its nucleus as there are positively charged protons in that nucleus. While a neutral gas may carry the potential of substantial chemical activity together with dynamic effects (e.g., fluid turbulence), such a neutral gas exhibits little or no response to electric and magnetic fields— and such neutral gases are substantially unable to conduct electrical potential therethrough. A neutral gas, however, can be excited or energized to the plasma state when a sufficient proportion of its atoms become ionized by losing one or more electrons. Ionization can occur as a result of a number of processes, such as (i) a neutral gas becoming so hot as to cause the atoms to collide and jar loose electrons (thermal ionization or TI), (ii) a neutral gas being subjected to a high intensity light source that strikes the atoms with energetic photons that displace electrons from their orbits (photoionization or PI), (iii) a neutral gas being subjected to electric fields that are strong enough to strip away electrons from the atoms (field ionization of FI), and (iv) in the case of non-gaseous materials, a spark or electrical discharge pulse can ionize analytes in the surface of a solid.

A resulting plasma (ionized gas) consists of interpenetrating and interacting accumulations of freely roaming charges (both negative and positive). This gas state can shift from neutral to ionized by photoionization or field ionization by the means disclosed herein, it is believed, within the range of tens of femtoseconds to hundreds of picoseconds. For purposes of this disclosure, the method of forming the initial plasma (ionized gas) volume involves irradiating a captured neutral gas volume with a high intensity wavelength (λ) ranging between about 190 nm to 263 nm (or more broadly, within the UV spectrum defined as λ from 10 nm to 400 μm; or, frequency range of $1.0 \times 10^{15}$ Hz to $6.0 \times 10^{16}$ Hz). Thereafter, an intense application of energy is applied by to targeted surface layer by creating an ultrafast high-intensity electrical discharge within the ionized gas volume and the surface layer to cause an electrochemical volatilization of molecules of the surface layer, i.e., a plasma-mediated ablation. Each high intensity burst of electrical energy forms a critical density plasma at the surface layer thus removing surface material that is ionized. According to this plasma-mediated form of electrochemical material removal, each energy pulse applied to the surface layer when above a certain threshold level is channeled into to the formation of ejecta (gas plume and fragments) by the volatilization or decomposition of macromolecules of the surface layer. The plasma, or microplasma, decays rapidly as ejecta and the plasma transfers heat and energy away from the surface layer and also releases energy in the form of radiative emissions. It is postulated that such energy applications to the surface layer (dependent on ionization proportion of neutral gas and intensity of the electrical discharge), can be modeled to provide selective volumetric removal of material per pulse of energy. In sum, a controllable process for selective volumetric tissue removal is provided by a system including a computer controller for successively rapid sequencing of (ii) photoionization of a partially-captured neutral gas volume, and (ii) creation of a high-intensity electrical field for volatilization of a targeted thin surface layer.

In the present invention, at sufficiently high energy levels (or voltage V), charged particles in a plasma can possess sufficient energy to break down common molecular bonds in macromolecules of a tissue surface. For example, such bonds may be carbon-carbon bonds, carbon-nitrogen bonds, etc. It is believed that the energy required to disrupt such bonds is within the range of 3.0 eV to 4.0 eV. Preliminary calculations (to be refined for publication in a future disclosure) suggest that the estimated electron energy applied by the inventive system can far exceed 4.0 eV when operating at 300 to 1000 volts, making various assumptions concerning distances between the active electrode(s) and the targeted site; and the electron population of the media (gas or liquid) interface between the electrode(s) and the targeted site.

The invention provides a technique for biological material removal that allows precision of ablation depth by removing a discrete thin layer of material with optional modes of (i) pulsed applications of intense energy to a targeted site, or (ii) the creation of a sustainable high energy plasma at the interface between a working surface and the targeted site to cause molecular volatilization.

The invention advantageously provides a control technique for controlling material removal by causing a plurality of micron-dimensioned energy-tissue interactions over a grid of an instrument working surface.

The invention advantageously provides a control technique for controlling material removal by creating a plurality of micron-dimensioned gas volumes that can be switched between non-conductive and conductive states for controlling energy applications to the targeted tissue surface.

The invention provides a control technique for controlling the distribution of energy across a targeted site by creating a plurality of micron-dimensioned plasma volumes that evenly apply energy across tissue.

The invention provides a control technique for enhancing the energy of a plasma to facilitate a plasma-mediated ablation by utilizing electron-emissive coatings and UV irradiation of a microchannel plate.

The invention advantageously provides a technique for removal of surface layers of body structure substantially without collateral thermal damage.

The invention advantageously provides a technique for ablation (material removal) that is generally insensitive to tissue's linear absorption characteristics.

The invention advantageously provides a technique for ablation (material removal) that is generally insensitive to tissue hydration.

The invention advantageously provides a technique for ablation of surface layers of body structure that is exposed to a gas environment or immersed in a fluid environment.

BRIEF DESCRIPTION OF THE DRAWINGS

FIG. 8A being a view of introducing the working end of the probe of FIG. 5 into a workspace proximate to the patient's spine; FIG. 8B being an enlarged view of the working end in a portion of a fluid-filled workspace proximate to surface layers of a targeted structure.

FIG. 9A being an illustration of the distal working face in the fluid environment; FIG. 9B depicting a neutral gas being introduced into shape structure of the working face displacing the immersion fluid; FIG. 9C depicting irradiation of the neutral gas volume with UV energy thereby photoionizing the gas in a first (estimated) ps time interval; FIG. 9D depicting an initial (estimated) ps time interval in creating a high-intensity electrical field in the ionized gas volume to create a plasma and thereby ablating tissue; FIG. 9E depicting a subsequent time interval wherein the sequence of events begin to be repeated as the neutral gas is introduced into the working face.

FIG. 15A is a view of a plurality of microchannel terminations with the surrounding structure of the working surface in phantom view in relation to a micron-dimensioned grid representing the targeted site, and further depicting the step of creating electrical potential at the electrodes;

FIG. 15B is a view of the plurality of introduced media volumes similar to FIG. 14A after the step of ionization of the volumes by a UV source with the ionization graphically depicted as shading;

FIG. 15C is a similar to that of FIG. 15B this time depicting the transient (ionized) conductive path in the surrounding gas media that is extended distally from the working surface.

FIG. 15D is similar to FIG. 15B and occurs substantially contemporaneous with the ionization of FIG. 15B at which time the electrical potential at the electrode controllably applies energy across the ionized media volume to the targeted site.

FIG. 15E follows FIG. 15D after a brief interval (estimated at 10's of ns) and depicts the material removal process (not-to-scale) wherein the application of energy cause volumetric material removal resulting in an ejecta plume into the remnants of the ionized gas media.

DETAILED DESCRIPTION OF THE INVENTION

Figure 1A:
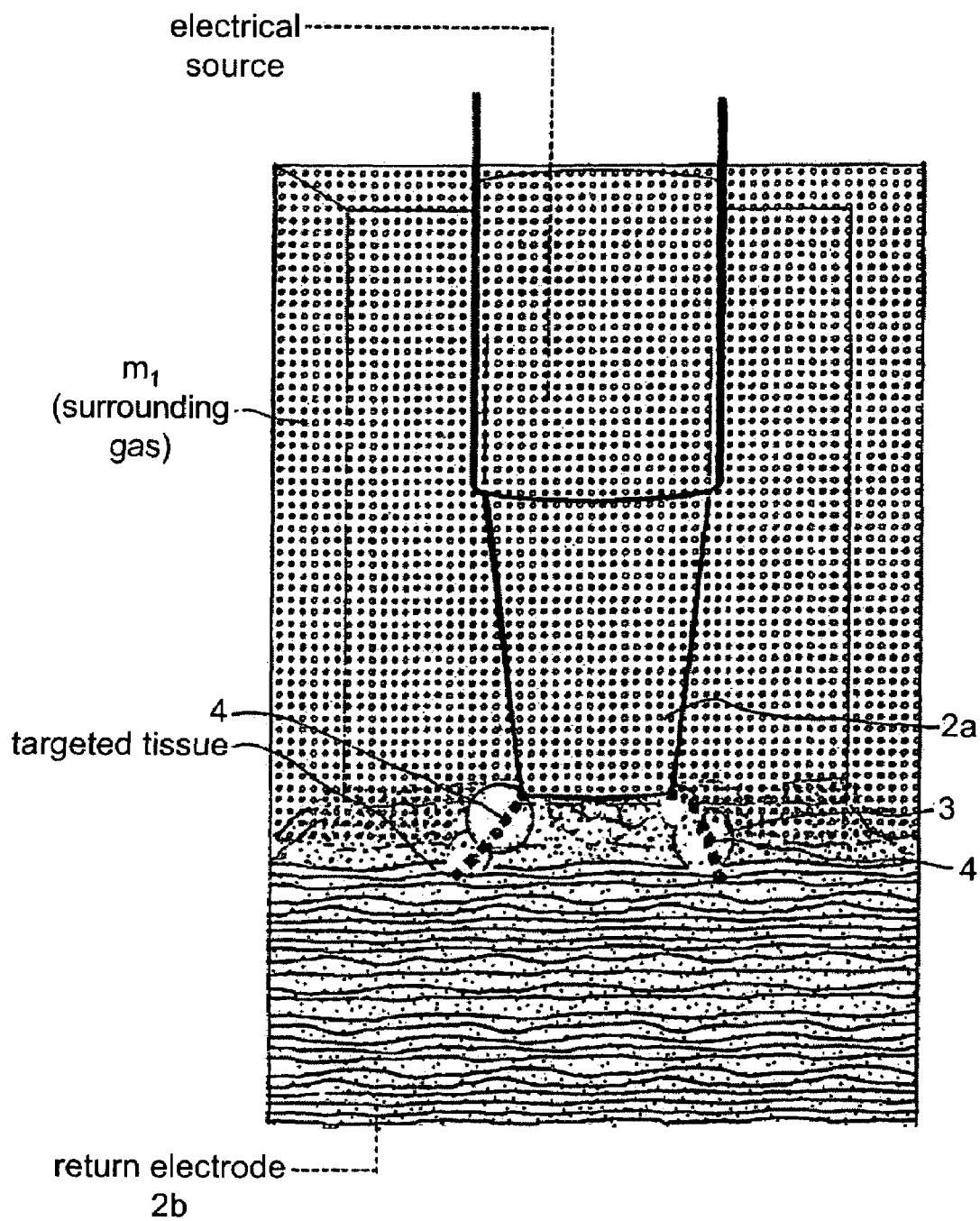
FIG. 1A is a view of a prior art working end of a monopolar probe in relation to a tissue surface illustrating the method of creating insulative gas bubble to cause spark-type discharges to ablate tissue.

I. Operational Principles of Plasma-Assisted Cold Ablation of Thin Surface Layers.

The several principles of operation of an exemplary plasma-mediated ablation system 5 (see FIG. 5) for the ratable removal of thin surface layers will be described in detail in the following sections in connection with an exemplary procedure: the selective removal of targeted tissue that is proximate to a delicate structure such as a nerve (e.g., material removal in a laminectomy/disketomy procedure for treating a herniated disc). The following description of the operation the probe of FIGS. 5-6 and the techniques of FIGS. 9A-9B and 9A-9F are for exemplary purposes only and are not intended to limit the application of the system and methods of the invention. As will be described in further detail herein, the system may have application in a wide variety of surface layer ablations and volumetric tissue removal procedures. The system 5, which may be described herein as a PASCAL system (plasma-assisted cold ablation layer-by layer), is developed in accordance with the following operational principles, which will be described seriatim. The PASCAL system provides: (A) ultrafast pulses of energy applied to thin surface layers to create critical density microplasma events without transfer of thermal energy, (B) confinement means for at least partially confining a non-equilibrium microplasma formed by photoionization to allow electrical potential therein to thereby allow energy application by an electrical source (as opposed to laser source), (C) control means for controlling pulse duration and the repetition of energy application events to provide layerby-layer volumetric material removal; and (D) feedback control systems (optional) based on analysis of plasma luminescence caused by the plasma-mediated ablation process.

A. Operational Principle: Ultrafast Pulsed Energy Application for Volatilization of Surface Layers.

A first objective of the present invention is to provide an ultrafast pulsed application of electrical energy to a targeted site on a surface layer of structure in a patient's body. In this invention, each discrete application of energy (pulse or burst) can be defined by quantity of energy (J) and a duration in which such energy is deposited within the surface layer. A first operational principal of the invention is that, for a given energy quantity in joules, the duration of energy application is less than a threshold electron-to-lattice energy transfer time for the surface layer of the targeted structure. It is postulated that for surface layers of structures here in question, this characteristic energy transfer time is in the range of about 10 ps to 100 ps. Thus, when a high-intensity pulse of energy is applied in a sub-threshold duration, the mechanism of layer removal can be characterized as a chemical alteration of surface molecules, or more specifically an electrochemical-tissue interaction since the energy is applied by means of an intense electrical field. In contrast, if the pulse duration of energy application is at an above-threshold level (e.g., in the ms range) with sufficient energy to cause damage, the mechanism and characteristics such of ablation would differ. That is, above-threshold energy delivery would cause damage that is largely thermal in nature and characterized by vaporization, melting, denaturation, fracture, etc. (In this above-threshold energy delivery modality, the electron kinetic energy transfer to the material's lattice structure is dependent on thermal diffusivity, a material property which expresses the ability of heat to diffuse and is equal to the square root of the ratio between heat conductivity and specific heat capacity). The present invention, however, is directed to ultrafast pulses (subthreshold duration) of energy application that create a critical density plasma from a thin surface layer. More specifically, the intensity of the electrical field (or discharge) and its absorption in the surface layer results in volatilization of macromolecules in the layer thus causing actual ionization of the thin layer thereby removing bulk. The energy burst is absorbed non-linearly and produces quasi-free electrons which, in turn, may act as seed electrons to cause an electron avalanche by various ionization processes. (Various ionization processes fall within the scope of the practice of the method, e.g., collisional ionization, multiphoton ionization, and field ionization). These ionization processes lead to irreversible alteration in the surface of the structure as ejecta (gas and bulk material) is ejected from the layer. It is believed that a very high fraction of the applied energy is removed by the high-velocity ejecta. Thus, any instantaneous high temperatures caused by the energy application are removed from the layer by the plasma formation process. It is further believed that mechanical shock waves to the bulk material will be insignificant compared to energy applications at above-threshold levels as defined above. At the subthreshold energy duration applications proposed herein in accordance with practice of the method, there will be insufficient time for lattice coupling, thus resulting in insignificant thermal diffusion-induced collateral damage to the structure.

A further desirable consequence of using such ultrafast pulse of energy application for surface layer removal is that the method is relatively insensitive to hydration and density of the targeted surface layer, and is entirely chromophore independent. The drawback to the layer-by-layer plasma-mediated process disclosed herein is that the ablation rate, defined generally as the depth of layer removal per pulse, is small. That is, each pulsed energy application will only remove a layer having a thickness measured in μm's (microns). It is postulated that layer removal rate will range from about 1 μm to about 200 μm within the anticipated energy application parameters (from 0.1 J/cm.$^2$ to 1000 J/cm.$^2$; or 0.1 J to 10 J per pulse). In order to overcome the low rates of material removal per pulse of energy in the typical case that needs substantial volumetric removal, the repetition rate of pulsed energy application must be high. This operational principle of the invention will be described below in Section I(C).

B. Operational Principle: Photoionization of Neutral Gas and Confinement by Shape Structure and/or Fluid.

The previous Section I(A) described a means for plasma-mediated cold electrochemical ablation of layers of body structure, but to construct a system feasible for surgical use, it is necessary define operational principles for spatial control of the energy application at the targeted layer to cause molecular volatilization. The operational principles according to this aspect of the invention relate to (i) providing means for creating an electrically conductive (partially ionized) gas volume proximate to the layer that is targeted, since the plasma-mediated ablation process described in Section I(A) can only occur in such a condition; and (ii) providing means for at least partially confining the ionized gas volume in its non-equilibrium state for a sufficient time interval to create the intense electrical field therein to cause volumetric removal.

The present invention utilizes a probe with a distal working surface that in placed proximate to the targeted site for energy delivery. Thus, it is necessary to create the non-equilibrium ionized gas (an initial plasma) generally about this working surface. The invention utilizes a concept novel to biomedical applications for photoionizing a neutral gas volume introduced to the working surface. In such photoionization, a high-energy photon (e.g., from a UV source) irradiating the neutral gas may interact with an ionic electron leading to removal of that electron from the ion. To photoionize an ion requires a photon energy greater than the binding energy of the electron. As photons increase in energy (wavelength dependent), the cross-section for photoionization of a particular electronic state is zero until at a certain point the cross-section jumps to a finite value, which is termed a photoelectric edge. The method of the invention thus selects a radiation source characterized by photon/wavelength energies beyond the photoelectric edge as it relates to the selected neutral gas composition (for purposes of the disclosure, the gas may be any ionizable gas compatible with biomedical application, e.g., air, nitrogen, oxygen, $CO_2$, etc.). In the case of such photoionization, the departing electrons must exchange virtual photons with the nuclei for the process to occur. Such photoionization, therefore, tends to preferentially remove inner-shell (i.e., K-shell) electrons since these can most readily interact with the nucleus. Due to this effect, this process general leaves highly excited ions. After photoionization by photons of energy, the liberated electrons possess a kinetic energy and successive electron-electron collisions distribute this energy throughout the electron population with such kinetic energy being thermalised into a surrounding plasma. The non-equilibrium plasma thus created at the working surface of the probe and at the surface layer is capable of interfacing an intense electrical field (electrical discharge) with the targeted layer to cause the electrochemical ablation described in Section I(A). It is postulated that the photoionization of the neutral gas volume occurs within fs or ps and the duration of UV light pulse for such photoioization is described below in Section I(C) relating to repetition rates In accordance with practicing this method of creating a photoionized gas volume (non-equilibrium plasma), another aspect of the invention relates to confining or containing the ionized gas in its non-equilibrium state proximate to, or in contact with, the layer targeted for ablation. Essentially, two operational principles are employed to maintain the plasma's condition for sufficient duration to allow the high-intensity electrical discharge therethrough. First, the targeted surface layer is preferably immersed in a fluid environment (the fluid being any suitable water, non-conductive water-based solution or a saline solution, or a hydrogel) to prevent the ionized gas from rapid dispersion into the surrounding environment. In a surgery in the interior of a patient's body, such as an arthroscopic procedure, the standard use of saline immersion is compatible with the invention. By the term immersion, it is meant that the surface layer is covered in any suitable fluid to any particular depth, and the depth may be very slight and still accomplish the purpose of preventing dispersion of the ionized gas volume. For example, the fluid immersion may comprise a layer as thin as a film if it provides a seal between a perimeter of the working face and targeted layer to briefly contain the plasma. Thus, the method of the invention may be used on surface layers of body structure exposed to the atmosphere, such as a patient's skin, when covering the structure with a thin gel or water.

A second (optional) principle that is utilized to confine the plasma is the provision of a shape structure at the working surface of the probe, such as a concavity to at least partially confine the photoionized gas. This shape structure also is useful for controlling the volume of ionized gas which will play a role in the plasma-mediated transfer of energy to the targeted surface layer. This shape structure, as well as particular dimensions of an exemplary embodiment, will be described in Section II below.

C. Operational Principle: Controlled High Repetition Rate of Pulsed Energy Applications.

The above Sections described a novel pulsed plasma-mediated ablation process that occurs, per pulse, in a time interval that may range from picoseconds to microseconds. In the sequential energy deliveries and plasma formations, only a thin layer of tissue is removed by the electrochemical-tissue interaction. In order to provide functional volumetric removal, the ultrafast pulsed energy event must be repeated at a high rate, and this Section describes operational principles relating to the selection of such a repetition rate. At a theoretical high repetition rate, there will be a high rate of volumetric removal. However, if the repetition rate is too high there may be collateral damage from thermal effects conducted to the surface layer by the plasma, which would defeat the objective of the invention in providing a substantially cold volumetric removal process. While it is postulated that the electrochemical-tissue interaction will occur without substantial thermal effects, a succession of ultrafast plasma creation and decay events may build up thermal effects in the plasma that would be conducted to the surface layer thus being capable of causing collateral thermal damage.

The operational principle in determining a maximum theoretical repetition rate for pulsed energy applications concerns the relationship between duration of energy absorption effects by the surface layer and the layer's confinement of heat, which thus may result in unwanted collateral thermal damage. The operative construct is the so-called thermal relaxation time, and is defined as the time required for significant cooling of a defined volume of a body structure that has been elevated in temperature. Thermal relaxation is often defined as the time required for an elevated tissue temperature to be reduced by 50 percent. Many processes are involved in such cooling, such as conduction, convection and radiation. Macroscale conduction cooling in body structures probably dominates, but microscale radiational cooling at a very small target site proximate to a plasma may be important. For targeted sites on structure in a patient's body in laser applications, the rule of thumb is that the thermal relaxation time in seconds approximately equals the squared dimension of the targeted site in mm. (For example, a 0.5 µm size structure ($5 \times 10^{-4}$ mm.) will substantially cool in about 250 ns ($25 \times 10^{-8}$ seconds)). In the case of the inventive method disclosed herein, the fluid immersion aspect of the method is advantageous and will help provide rapid thermal relaxation. The fluid further may be pre-cooled which is beyond the scope of this disclosure.

In accordance with practicing the principles of the method, it is postulated that ultrafast pulses of energy will be absorbed in the range of 100's of ps to 100's of ns. It is further postulated that repetition rates in the range of from about 10 Hz to about 500 Hz (or even 1000 Hz) are possible without exceeding the relaxation time of the surface layer. At this time, the repetition rates are theoretical and are to be explored with bench tests. As a practical matter, the timing of controlled flows of a neutral gas to the working surface and irradiation of the gas volume may prevent extremely high repetition rates. It is believed that with repetition rates in range of 2 Hz to 100 Hz, layer removal rates could be as high a 1 mm./s while maintaining the desired minimal collateral damage characteristics of the plasma-mediated ablation.

D. Operational Principle: Plasma Luminescence Feedback System for Tissue Layer Differentiation.

A final operational principle underlying the practice of plasma-mediated ablation relates to the potential need for diagnostic means in the selective layer removal process to prevent the removal of layers of structures that must be protected. In many procedures relating to tissue removal by a surgeon, the ablation process will be initiated and terminated on the basis of the surgeon's visual observation of the targeted surface layer and evaluation of the ablation process. However, when ablating surface layers in the interior of a patient's body, particularly in a fluid environment, endoscopic observation of the ablation process may be poor. A principal reason for the author's investigation of plasma-mediated ablation in a fluid environment is that the inventive method advantageously will allow spectroscopic analysis of luminescence of the plasma, and control signals may be derived therefrom to terminate the ablation process. In other words, as each successive plasma is formed by the pulsed high-intensity electrical discharge, an opportunity is provided to use tissue layer differentiation diagnostic procedures based on spectroscopic plasma emission signatures. Such a spectroscopy system would utilize an optic fiber for collecting emitted light from the plasma generated by the volatilization of the surface layer and ejecta in the plasma. The light would be dispersed and analyzed by an analyzer system, such as an intensified, gated, optical multi-channel analyzer/spectrograph. Emission peaks characteristic of different tissue types would be used as reference data within the analyzer system. Thus, when the system detected emission characteristics of material that is not targeted, a signal would be provided to the controller to terminate the ablation process. It is believed this type of feedback system is novel to any electrosurgical ablation modality, and is made possible only because the practice of the method includes the creation of successive microplasmas at the targeted site. Further, this type feedback signal system is novel in that it can be utilized in a fluid operating environment. (Optical feedback systems based on spectroscopy have been tested with forms of laser energy delivery, but such laser systems cannot operate in a fluid environment. See, e.g., B. M. Kim, M. D. Feit, A. M. Rubenchik, B. M. Mammini & L. B. Da Silva, *Optical feedback signal for ultra short pulse ablation of tissue*, Appl. Surface Sci. 127-129(1998) pp. 857-862.)

II. Construction of Exemplary Type "A" System for Plasma-Assisted Cold Ablation

Figure 5:
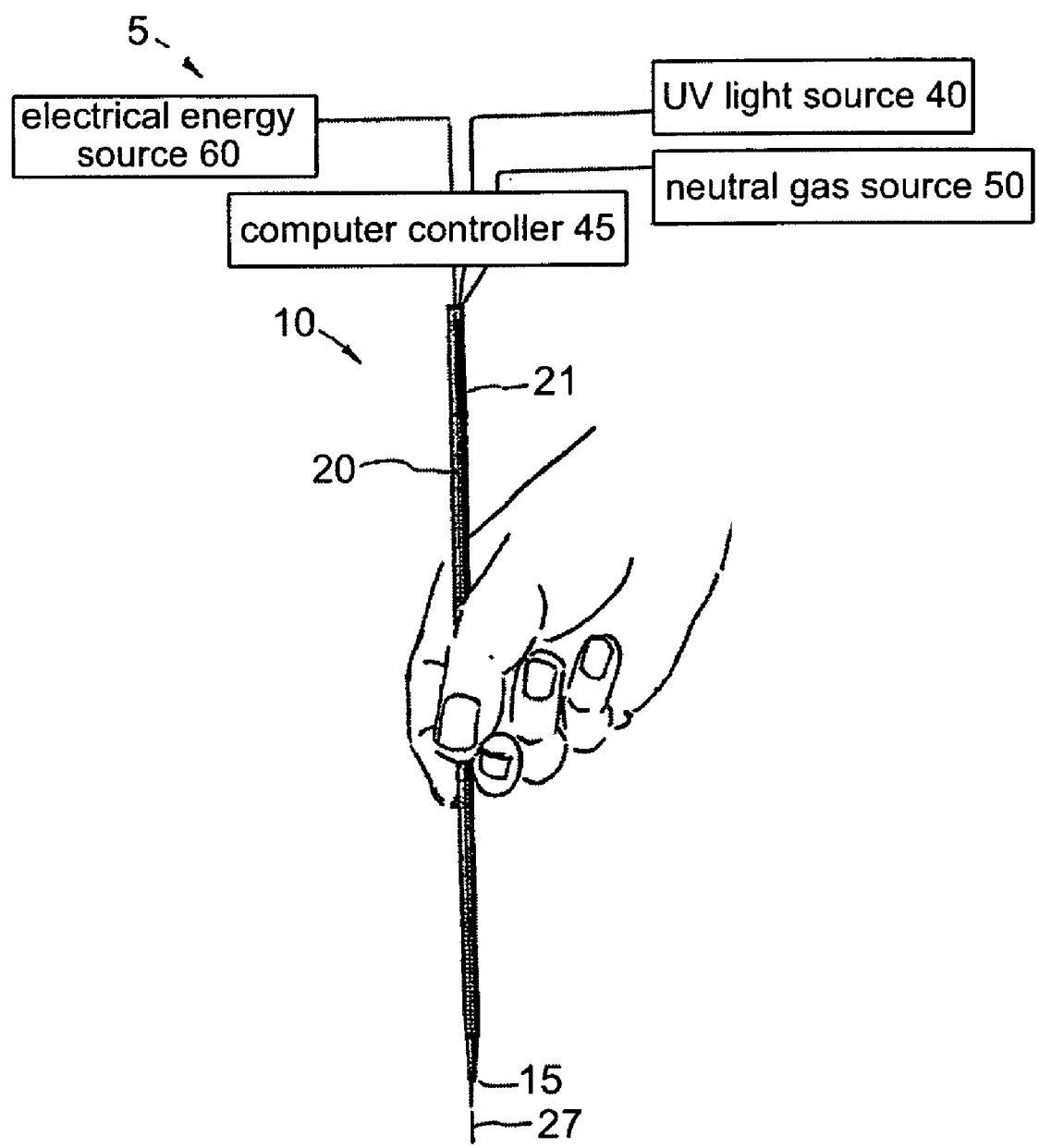
FIG. 5 is a plan view of an exemplary probe of the invention in relation to a human hand and a simplified block schematic diagram of the energy sources of the system suitable for practice of the principles of the invention.

Referring to FIG. 5, an exemplary Type "A" embodiment of PASCAL system 5 is shown which includes probe 10 and a remote energy sources in block diagrams. In this disclosure, the working surface 15 of probe 10 is adapted for positioning proximate to a targeted site on a surface layer of body structure to accomplish cold plasma-mediated ablation of the layer. The term ablation is used to characterize the surface layer removal process, and other descriptive words may be used interchangeably herein, such as, breakdown, decomposition, disintegration, obliteration, removal and volumetric removal to describe and define the plasma-mediated process that causes layers of a structure in, or on, a body to be altered, broken down, destroyed, damaged, or fragmented and ejected from the surface layer. The term structure of a patient's body as used herein is intended to be inclusive of any composition in a patient's body, and principally encompasses biological tissues but also is intended to describe all other body structures (some of which are sometimes not termed tissue) such as calculi, accretions, deposits, occlusions, bones and teeth, and the like.

The exemplary probe 10 of the system comprises an elongate extension member 20 having proximal (handle) end 21 and a distal working surface end indicated at 15 with a cross-section or diameter of body 22 being about from 1.0 mm. to 5.0 mm. (not limiting), the extension member defining longitudinal axis 27. The extension member may be fabricated in a variety of configurations to mechanically support at least one active electrode about in the working surface 15 and to allow the operator to position the working surface 15 in relation to a targeted site on a surface layer by manual or robotic manipulation of the proximal end 21 of the extension member. Typically, the extension member 20 comprises a small cross-section member or tube being dimensioned for introduction into the interior of a patient's body through a trocar (cannula) in a minimally invasive procedure, for example in arthroscopy, laparoscopy, or another thoracoscopic or endoscopic procedure. The elongate member may have any suitable length. The elongate member also may be rigid or flexible. A flexible probe may be provided with pull wires, shape memory actuators, and other mechanisms known in the art for articulating a distal end for positioning the working face proximate to the targeted site.

Figure 6:
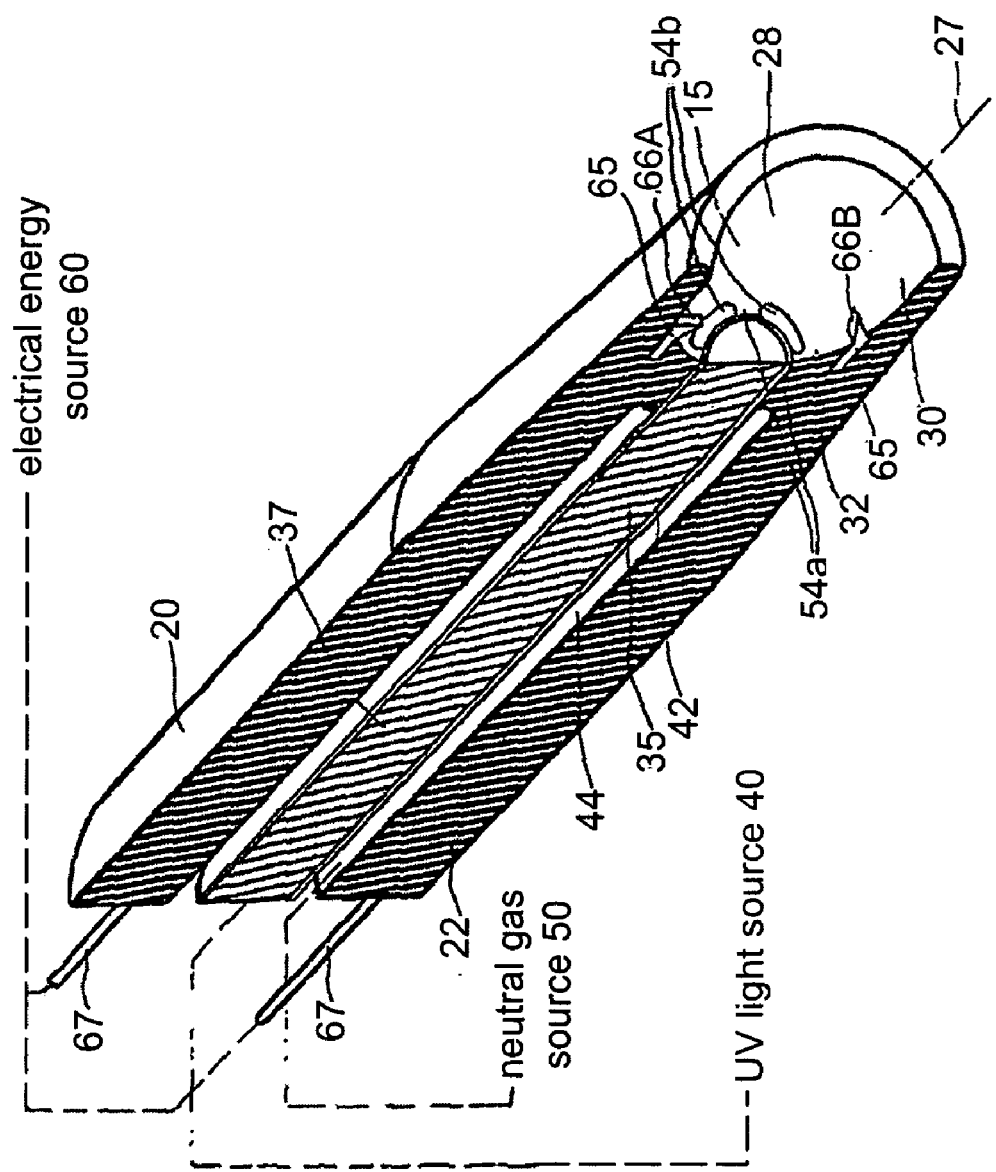
FIG. 6 is an enlarged sectional view of the working end of the probe of FIG. 5 taken along line 6-6 of FIG. 5.
Figure 7A:
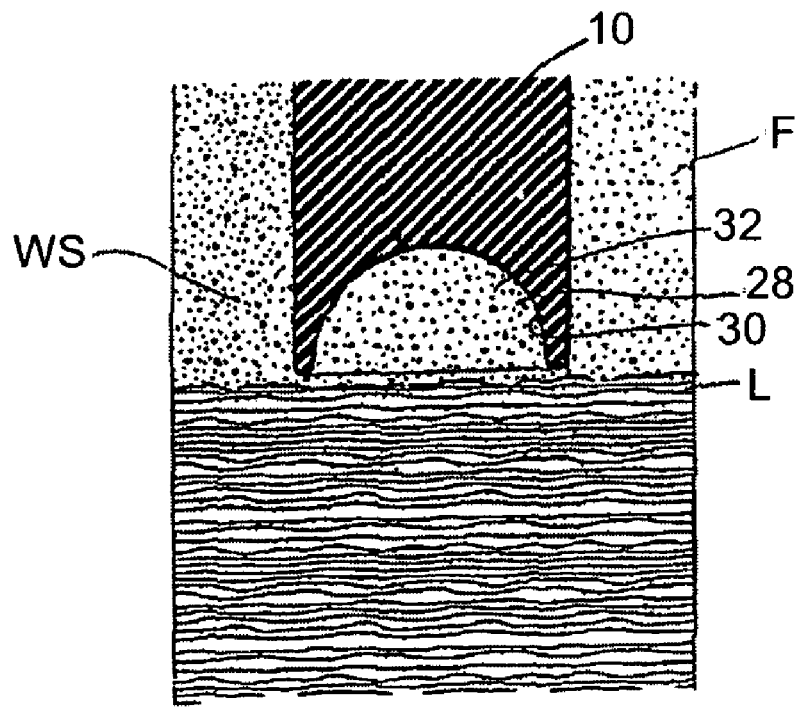
FIGS. 7A-7B are sectional schematic views of alternative shape structures at a working face of a probe similar to that shown in FIG. 6.
Figure 7B:
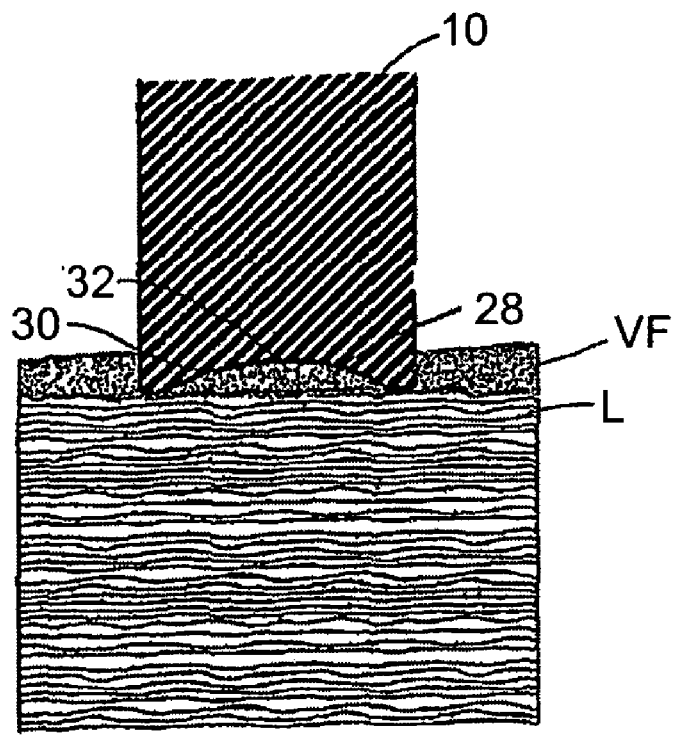

In FIG. 6, it can be seen that working surface 15 defines a shape structure 28 comprising a concave or recessed portion 30. The recessed shape structure 28 is adapted to at least partially contain a neutral gas and its photoionized counterpart and the concavity may be of any suitable dimension or extend inwardly (proximally) to an interior chamber portion 32 and fall within the scope of the invention. FIGS. 7A-7B show sectional silhouettes of alternative shape structures 28 with FIG. 7A depicting a more concave shape structure suitable for use in an immersion fluid F in a workspace WS over tissue layer L and FIG. 7B showing a slight concavity (a lack of concavity altogether may fall within the scope of the invention) for use with a more viscous fluid VF or gel layer over tissue layer L.

Returning to FIG. 6, probe 10 carries a optical delivery or light-channeling means such as an optical fiber 35 (or fiber optic bundle, wave guide or other light-channeling means) in central portion 37 of extension member 10 which is adapted to direct light energy from a high-intensity source or UV source 40 as described above in Section I(B). The optical delivery subsystem depends on the design parameters of the tissue removal system and may alternatively comprise a fiber optic cable, an articulated arm with mirrors, or an open beam delivery system including coated reflectors and lenses to focus the radiative beam. In this embodiment, the optic fiber with cladding 42 is carried in central lumen 44 of the extension member 20. In any event, the working surface 15 is carried at a distal end of probe 10 to allow the operator to maneuver the working surface into proximity to a targeted surface layer. It should be appreciated that the distal termination of the fiber 35 may have its cladding 42 partly removed (not shown) to cause photoionization along a distal portion of passageway or lumen 44.

A computer controller 45 is operatively connected to the high-intensity light source 40, and controls the activation of the source, as well as its pulse repetition rate, in response to control signals that are provided by the system operator. Any sort of on-off switch (foot pedal or hand switch not shown) is connected to controller 45 and provides activation signals in response to the actuation of the switch. The pulse repetition rate may be set by the operator by a form of rheostat control connected to controller 45 which increases or decreases the repetition rate in response to the operator selection. It should be appreciated that any suitable high-intensity UV source 40 may be suitable for delivering energy along the light-channeling means 35, and a conventional discharge lamp known in the art is preferred together with optional filters, combiners, and associated optics may be suitable to perform the method of photoionization aspect of the method described above (i.e, a discharge lamp passes an electric current through a rare gas or metal vapor, wherein electrons collide with gas atoms exciting them to higher energy levels which then decay to lower levels by emitting light; mercury, hydrogen, deuterium, Ne, Ar, Kr, and Xe discharge lamps all may useful for the photoionization aspect of the method). The light source is preferably remote and carried to probe 10 by a flexible fiber (not shown) but the light source also could be carried in a handle portion of the probe. The light source 40 also may be an excimer laser, such as an OPTex system by Lambda Physik, Inc., 3201 West Commercial Blvd., Ft. Lauderdale, Fla.

The UV energy radiated from source 40 is pulsed as is known in the art by a computer controller 45 capable of controlling the delivery of light pulses having a pulse duration ranging from about 100 ps to tens of ms with a repetition rate ranging from about 1 Hz to 1000 Hz. In the exemplary embodiment of FIG. 6, extension member 20 may carry a single optical fiber or a fiber bundle having any suitable diameter, for example ranging from about 100 μm to 500 μm.

FIG. 6 further shows a neutral gas delivery source 50 that communicates with the interior lumen 44 or passageway in member 20 that is configured concentrically around fiber 35. The lumen 44 extends to its distal terminus 52 at the interface with the concavity or shape structure 28 with web portions 54a and opening portions 54b maintaining the fiber in a central portion of lumen 44. It should be appreciated that any fluid-tight passageway may be provided and it need not be a concentric relative to the light channeling means 35. The system further provides a positive (+) pressurization system indicated at 55 for moving the neutral gas to the working surface 25 and may include any pump means or gas metering means known in the art, such as a peristaltic pump. As illustrated in FIG. 5, the neutral gas pressurization system 55 is operatively connected to the controller 45 for timing gas inflows, or pulsed inflows, relative to the irradiation of the gas volume with photonic energy from the photoionizing source 40.

Referring to FIGS. 5-6, an electrical source 60 is provided as the energy delivery means to perform the electrochemical ablation, and the intense electrical field in the photoionized gas volume is created via an electrode arrangement indicated at 65. The exemplary active conductive electrode 65 of FIG. 6 is carried in the concave shape structure 28 of the working face 15. In accordance with the practice of the invention, the electrode arrangement 65 will have one active surface portion 66 with a particular surface geometry shape that is adapted to enhance the intensity of the electric field and the current density at the time of each pulsed energy delivery. For this reason, such surface geometry preferably includes at least one projecting portion or sharp edge portion at the active surface. In the exemplary embodiment of FIG. 6, the surface geometry is characterized by a plurality of two projecting sharp edges 66A-66B that extend into the concave shape structure 28 of working face 15. It should be appreciated such preferred surface geometry may include only one conductive electrode portion, or a plurality of micro-scale sharp edges that may be characterized simply as surface roughness on the active surface of the electrode, and as such may be provided by any suitable chemical, electrochemical or abrasive method to create micro-edges on the active surface portion to thus enhance the high electric field intensities between the active electrode surface 66 and the targeted surface layer. In any type of electrode arrangement, the electrodes edges or projecting portion may be isolated but are the same source polarity as they will be electrically coupled to with a common electrical lead 67 either in the proximal end 21 of the extension member or at the electrical source 60. The exemplary active electrode 65 is shown as extending around axis 27 of the concave portion 28 but it should be appreciated that the electrode could be located at any other suitable location about the working surface. Referring still to FIG. 6, the electrode 65 is coupled to a conductive lead or wire element 67 that extends through body portion 22 of elongate member 20. The body portion 22 of extension member 10 may be any suitable insulated material such as a ceramic, plastic, glass or a combination of separate elements as are known in the art.

In the block diagram portion of FIG. 5, it can be seen that the system 5 has an electrical source 60 that is connected to electrode arrangement 65. The electrical source 60 may be any suitable electrical energy source as is known in the art than is capable of delivering high intensity electrical current, for example in the range of 10 to 2000 volts. The electrical source 60 of the present invention preferably delivers a high frequency voltage that may be selected from a range to generate average power levels ranging from a few milliwatts to hundreds. of watts depending on the targeted surface layer and the desired the rate of removal. The controller 45 associated with the electrical source 60 would allow the operator to select the voltage level according to the specific requirements of surface layer removal procedure. It is postulated that the voltage applied between the active electrode and the surface layer and return electrode will be in the range from about 50 volts to 2000 volts. The electrical source 60 is coupled to computer controller 45 to control the timing of energy delivery in relation to the timing of the photoionization step, and also may be programmed with suitable software 72 to allow independent modulation of parameters of electrical energy delivery, including: (i) voltage, current and peak electrical power per time interval; (ii) the length of a time interval of current delivery; and (iii) the profile of energy delivery within each time interval, to allow 1 to 1000 Hz repetition rates.

The computer controller 45 of the invention depicted in FIG. 5 may further be provided with feed-back circuitry known in the art for measuring the impedance between the active electrode surface 66 and the targeted surface layer. The impedance level will change, as will be described in the steps of the method shown below in Section III, as the neutral gas volume is photoionized, and thus feedback of the change in impedance can be used as a control signal for initiating the step of high-energy electrical energy delivery.

III. Method of Use of Type "A" System for Plasma-Assisted Cold Ablation of Surface Layers.

Figure 8A:
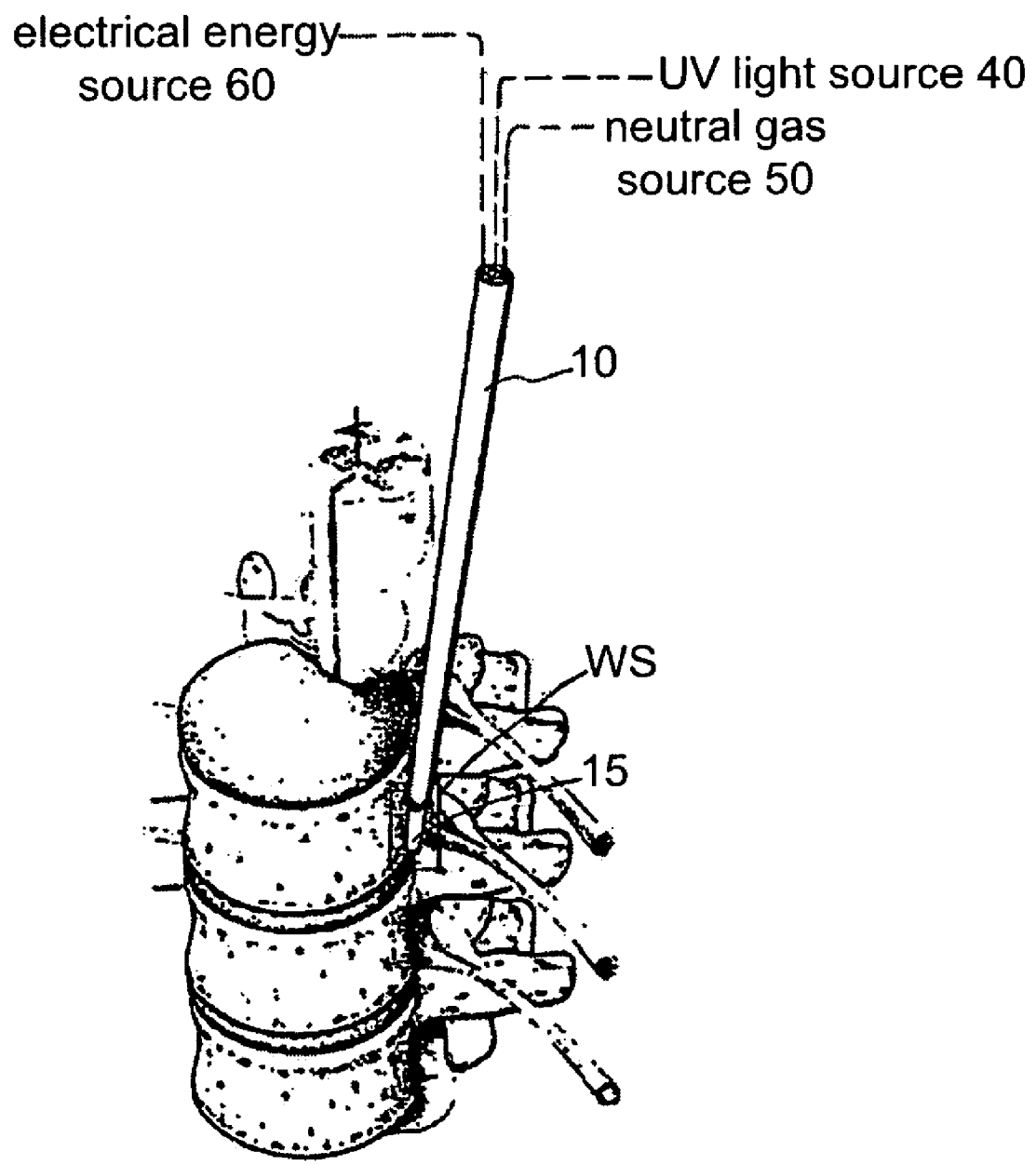
FIGS. 8A-8B are views of a method of practicing the principles of the invention in a laminectomy/disketomy procedure for treating a herniated disc.
Figure 8B:
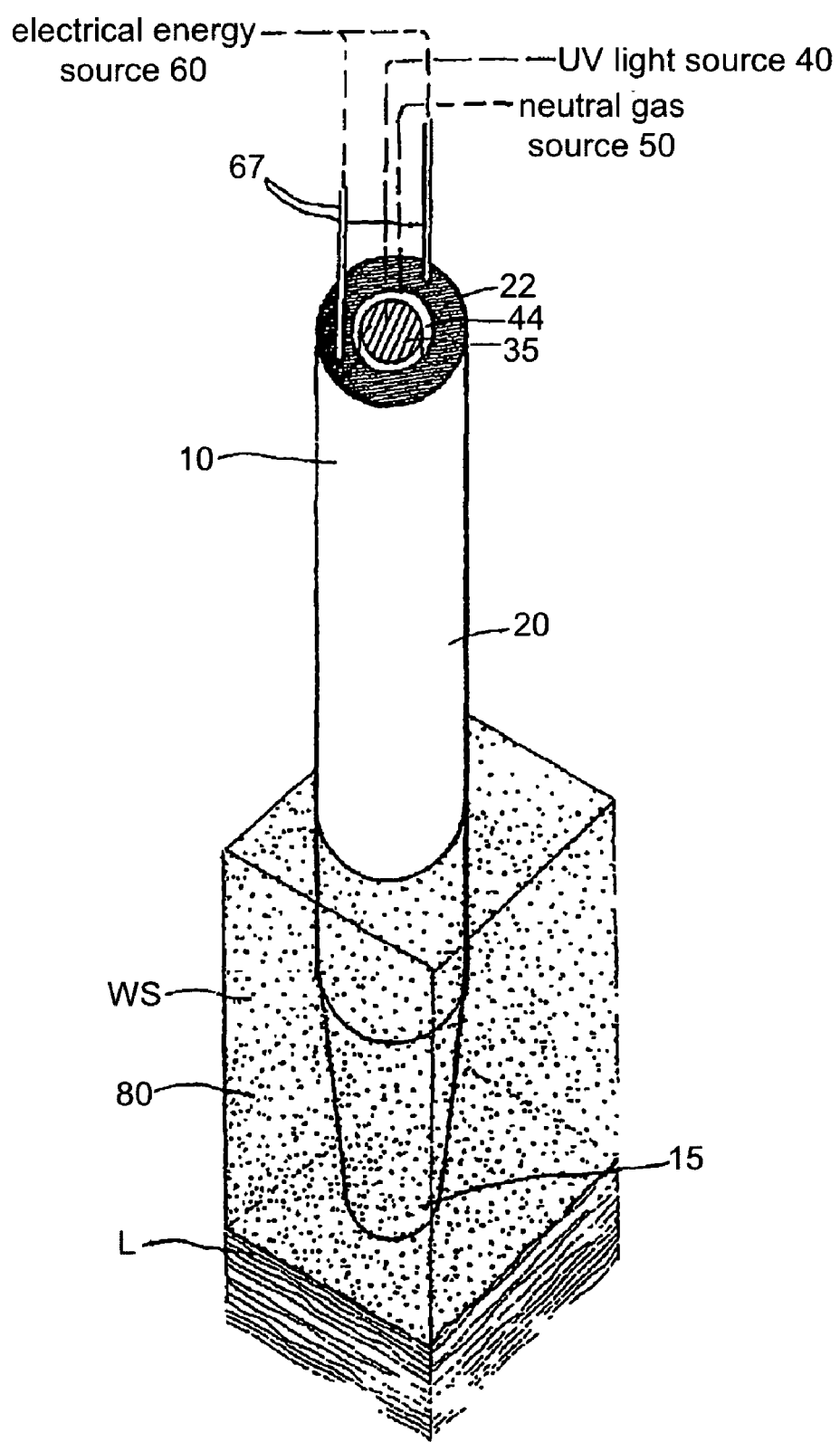

In practicing the method of the invention in a laminectomy/disketomy procedure to treat a herniated disc by removing surface layers of tissue, the patient is be prepared in any conventional manner with anesthetics and FIG. 8A depicts the elongate extension member 20 and its working face 15 being advanced into a working space WS to the targeted layer L. The surgeon may advance the working face 15 under endoscopic vision or by other manners known in the art (not shown), such as being assisted by real-time imaging. FIG. 8B represents an enlarged view of the working face 15 in a workspace that is filled with a fluid 80. FIGS. 8B & 9A-9E show that the patient's body is coupled to a ground pad or return (−) electrode 85 as is known in the art.

Figure 9A:
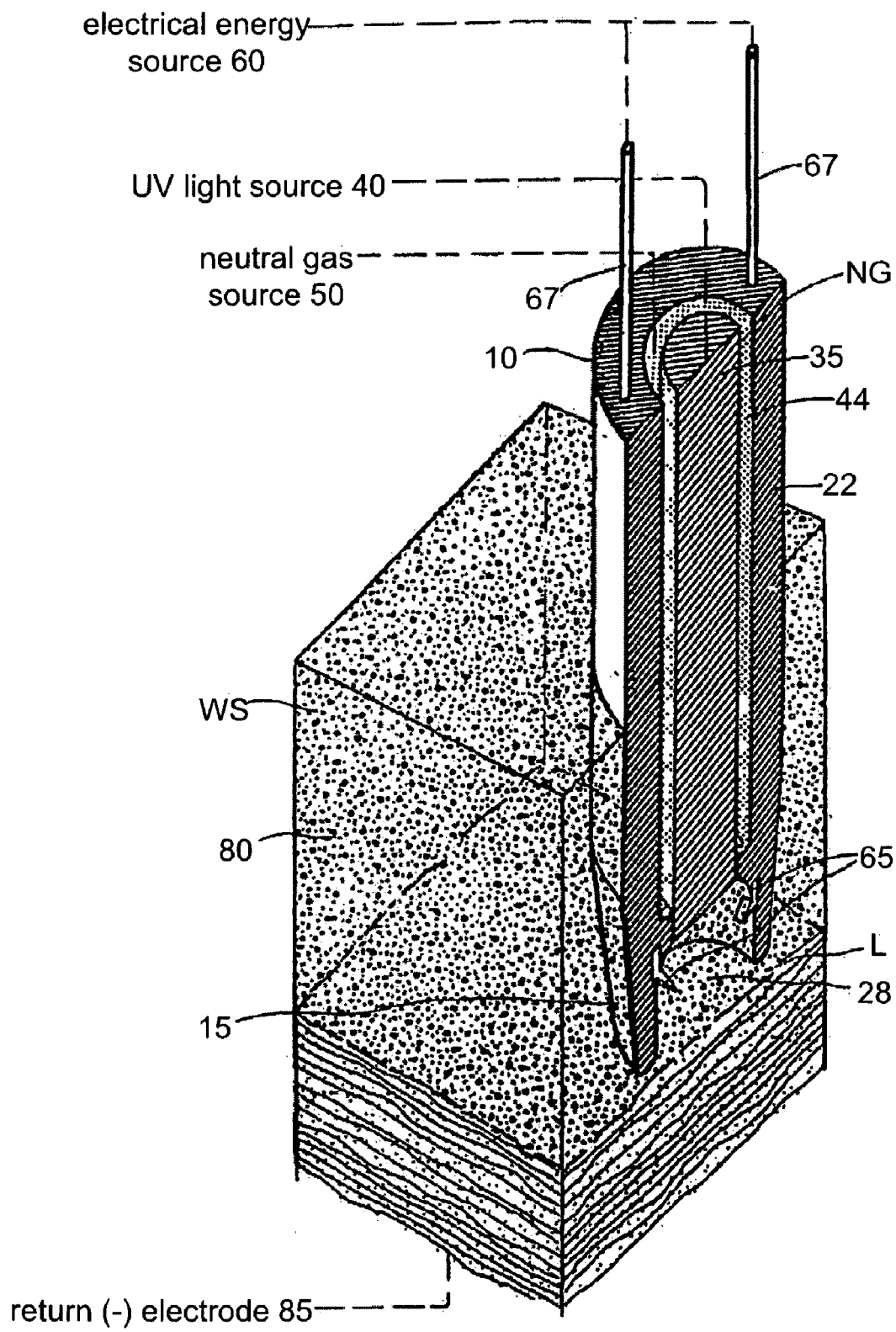
FIGS. 9A-9E are greatly enlarged views of the sequence of steps that comprise the method of practicing the principles of the invention for removing layers of any surface of a body structure immersed in a fluid.
Figure 9B:
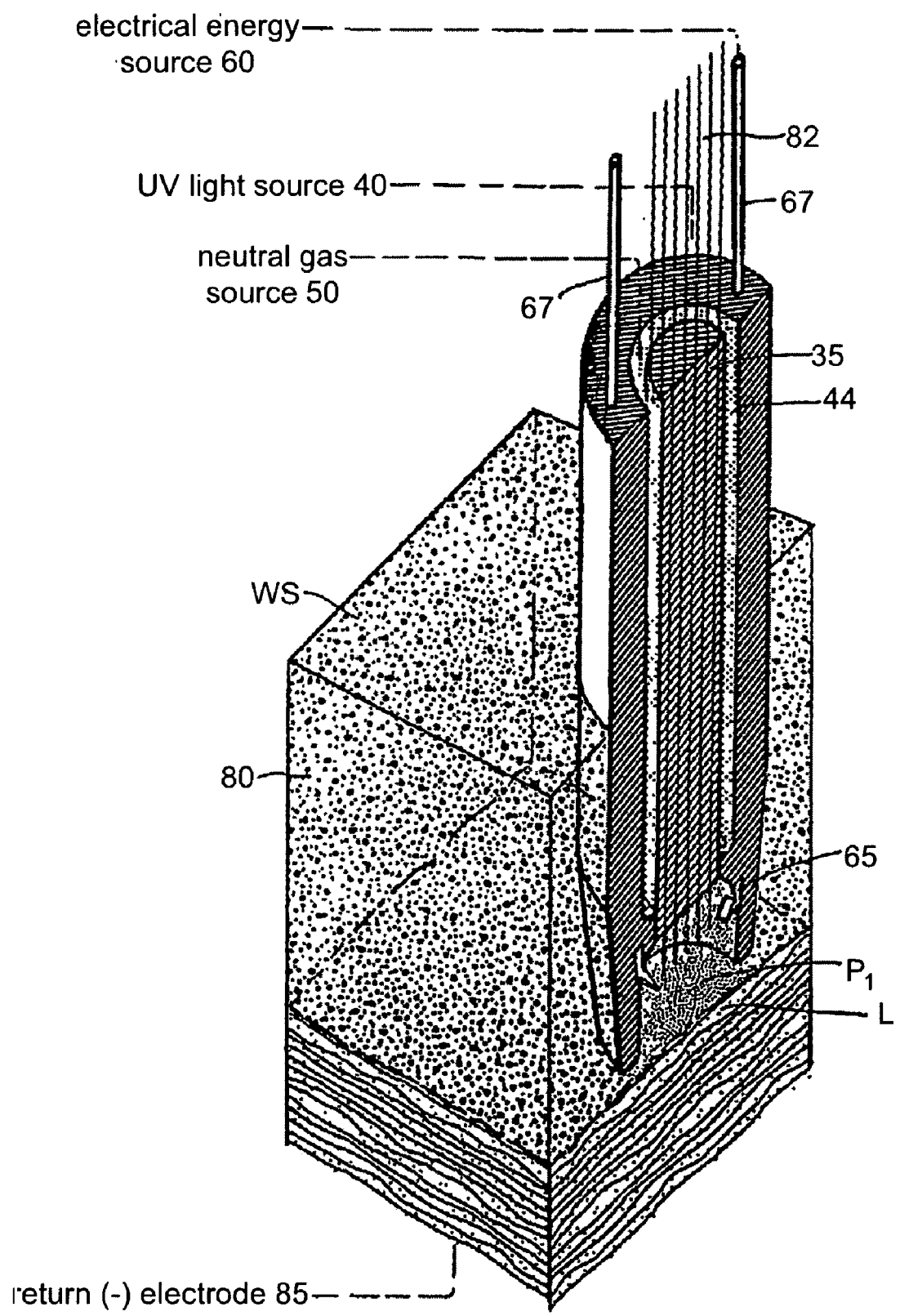

Now referring to FIG. 9A, a sectional view of the distal end of extension member 20 is shown positioned proximate (within about 1 mm. or less), or pressed gently against the targeted layer L (it should be appreciated that layer L may be the surface layer of any body structure). FIG. 9B then shows actuation of the system by controller 45 wherein a neutral gas NG is introduced through lumen 44 into the working face 15 with the volume being captured by the concave shape structure 28 and the surrounding fluid 80 which prevents the gas from rapidly dispersing.

Figure 9C:
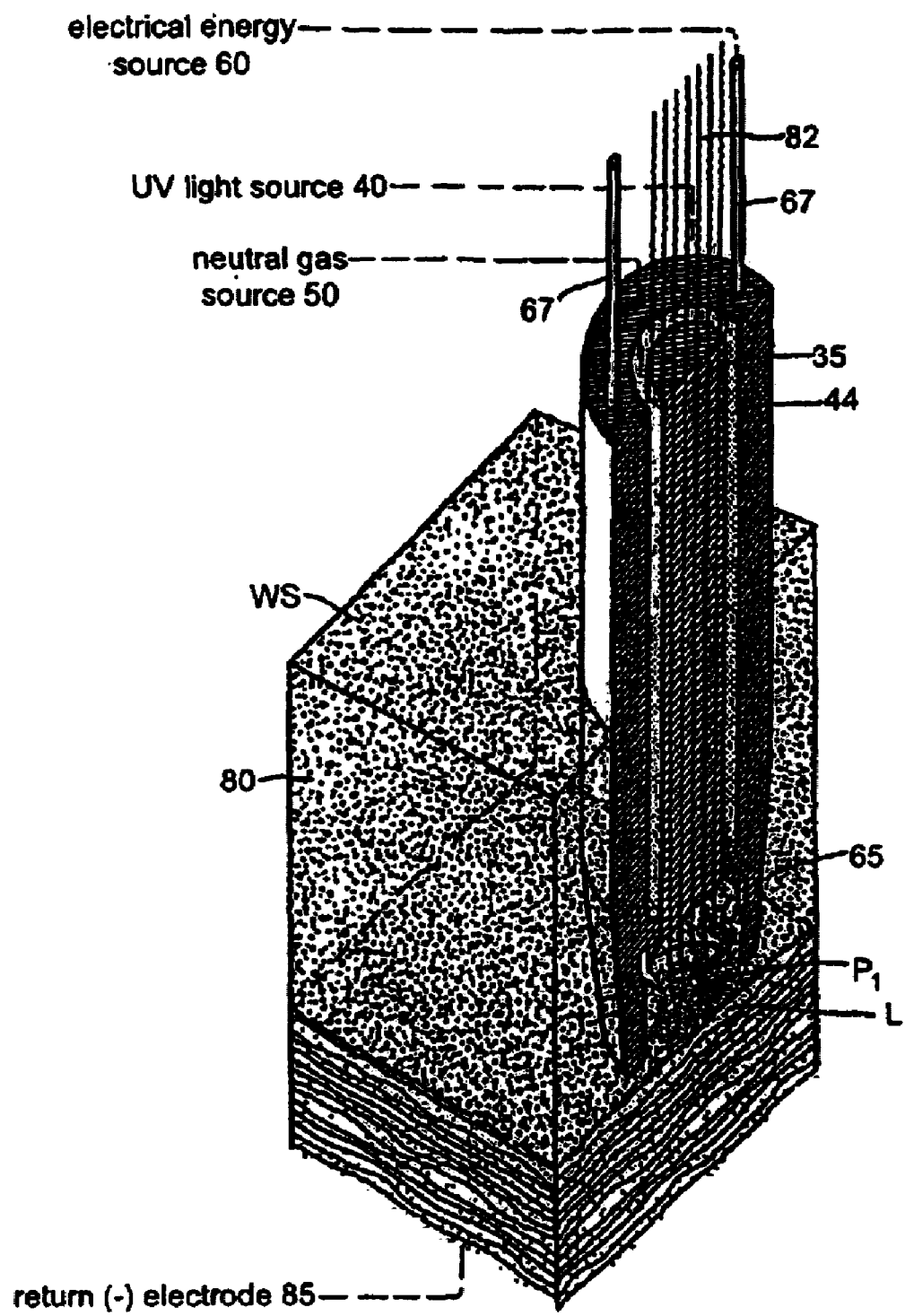
Figure 9D:
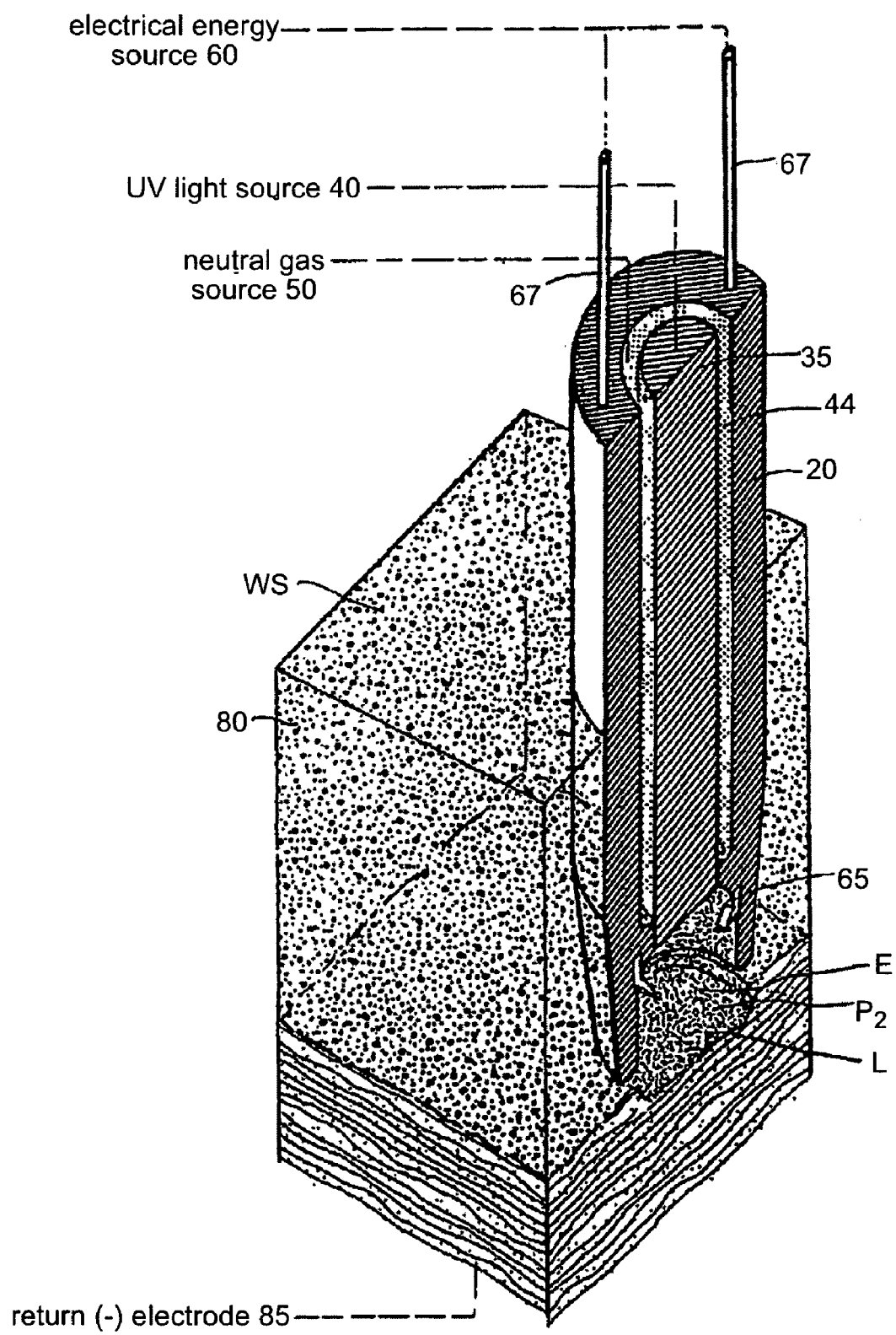
Figure 9E:
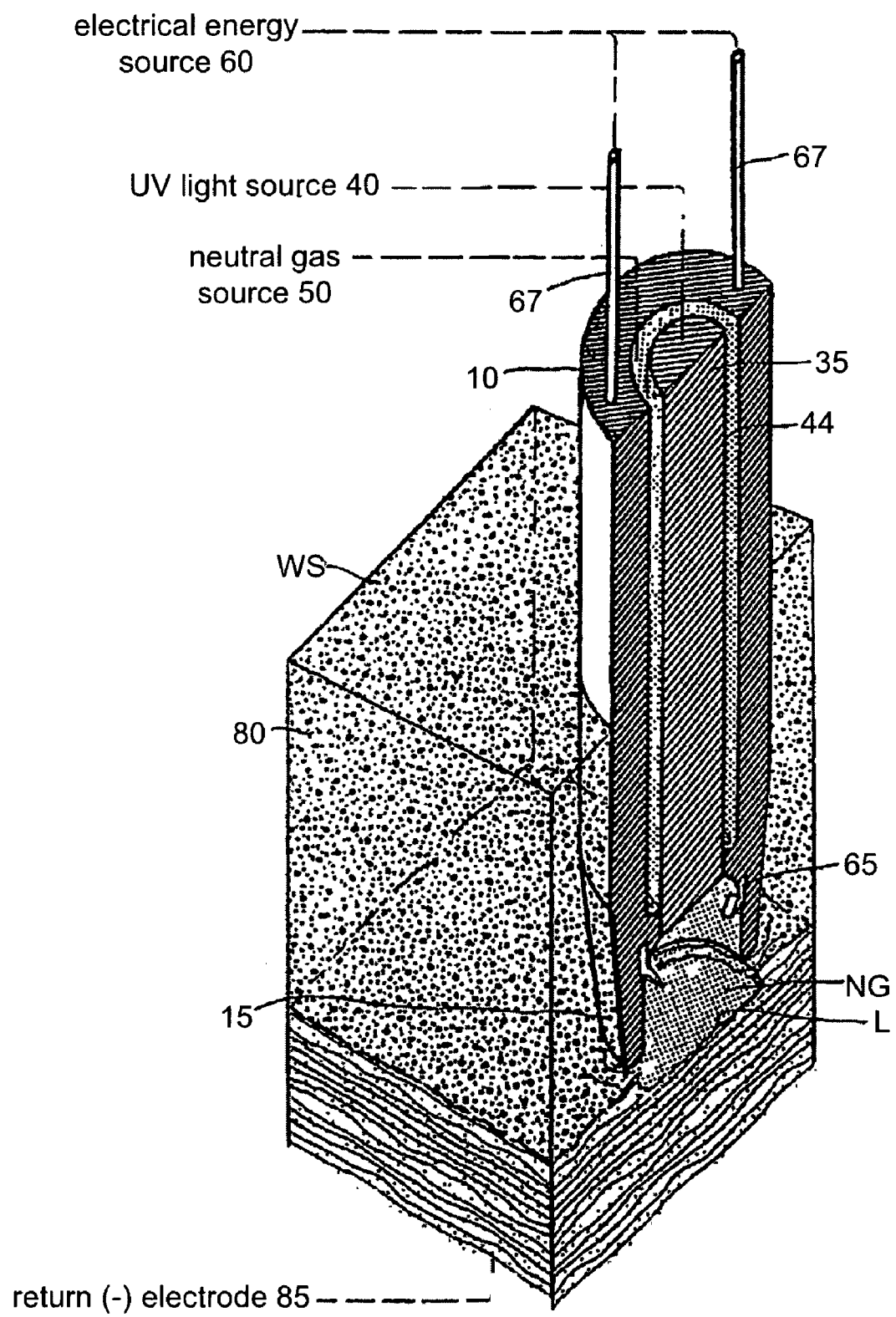

Now turning to FIG. 9C, the controller 45 after a pre-selected time interval irradiates the neutral gas volume with UV energy via beam 82 that is carried through optic fiber 35 from source 40. FIG. 9C thus depicts the step of photoionizing the neutral gas volume to create a conductive plasma indicated at $P_1$ that will remain in such non-equilibrium state for a first brief time interval. In FIG. 9D, the controller 45, after a pre-selected very brief time interval, triggers the power source 60 to deliver an intense electrical energy pulse from the active electrode surface 66 across the plasma to layer L (that is coupled to return electrode). FIG. 9D thus depicts the volatilization or commencement of ionization of layer L which, in effect, begins to alter the condition with other species to form an altered plasma indicated at $P_2$. In FIG. 9D, the volatilization of the surface layer L removes material from the layer by application of an energy quantity to the layer with ejecta E depicted in the plasma $P_2$, wherein the ejecta is essentially gases and possibly material fragments (depth of material removal exaggerated in FIG. 9D for a single plasma creation event). In a very brief time interval subsequent to the ultrafast fast event depicted in FIG. 9D, the plasma $P_2$ will decay. Thereafter a repetition of the plasma-mediated material removal process occurs as the controller 45 repeats the plasma-mediated ablative pulses in accordance with the events depicted in FIGS. 9A-9D. FIG. 9E shows the next step in this sequence with the neutral gas NG being introduced into the working face 15. It should be appreciated that the probe may be translated across layer L to remove material in a path or maintained in a stationary to drill a hole in the layer, either of which may be an element of the procedure. The distalmost surface of the probe preferably is to be held gently against the tissue layer, of slightly above the tissue layer In a diskectomy procedure as indicated in FIG. 9A, material is removed as required under endoscopic visualization, without thermal collateral damage to surrounding tissue.

The method of the invention may further include the step of analyzing the emission spectra by means of the fiber optic 35 which is coupled to a remote plasma luminescence spectroscopy system and controller 45. For example, the plume following a ultrafast plasma creation event in removing disc material in the exemplary procedure will provide emissions that can be compared with reference data for a known material in a disc, such as calcium If the emissions from the plasma exhibit characteristics that compare with non-targeted disc material, such as a nerve, the spectroscopy system can signal the controller 45 to terminate energy delivery.

IV. Construction of Type "B" System for Plasma-Assisted Cold Ablation.

A Type "B" embodiment (not shown) is very similar to the Type "A" embodiment except that the central core of the probe carries an optic fiber that is utilized to collect emitted light emissions from the plasma $P_2$ indicated in FIGS. 9D-9E. The emission peaks of the plasma $P_2$ are fed to a spectroscopic analyzer system 90 (see FIG. 5) and compared to the peaks in reference data to determine whether non-targeted tissue types have been affected by the ablation. The system is connected to controller 45 and may be programmed to terminate the ablation process within ns or ms.

The Type "B" system also includes impedance-measuring circuitry for triggering the delivery of electrical energy to the (photoionized gas) plasma $P_1$ as indicated in FIG. 9C. In other words, instead of providing programming in controller 45 that triggers energy delivery in a pre-selected time sequence, the impedance-measuring circuitry can continuously measure impedance within the region between the active electrode surface 66 and layer L which is altered by (i) the photoionization of the neutral gas volume as shown in FIG. 9C as well as its confinement, and (ii) the distance between the working face 15 and layer L.

Another aspect of the Type "B" embodiment of the invention (not shown) is the provision for aspiration of ejecta and fluid from the workspace. For example, if the targeted layer is a portion of malignant tissue, it may be useful to sequence aspiration of the ablated tissue fragments (along with gas and fluid) from the workspace. The controller would be adapted to provide such pulsed aspiration between pulsed applications of energy. The passageway for receiving such removed material particles would preferably be a concentric lumen around the extension member 20 of FIG. 6, but it could also be any type of interior passageway and fall within the scope of the invention.

V. Construction and Method of Use of Exemplary Type "C" System for Plasma-Assisted Material Removal.

In a previous part of this disclosure (see "Summary and Objects of the Invention"), a number of processes were described to cause, induce or develop ionization of a captured neutral gas volume (or bubble), and thereafter terminate ionization of the gas, in an interface between a probe working end and a targeted site ts. Such an instantaneously and independently ionized gas volume can then cause an intense application or arc of electrical energy from an electrode to the targeted site ts across the gas volume to volumetrically remove surface layers of an anatomic structure. Several ionization processes were described above, viz., photoionization (PI), field ionization (FI), thermal ionization (TI) and the ionization of surface analytes from a solid material. In this Type "C" embodiment 205, the use of independent field ionization (FI) means is described as an option in Section V(C) below and at times referred to as the first energy source. In addition, a working end carrying a microchannel plate (MCP) is disclosed in Section V(B) below which comprises an electron-emissive coating on a microchannel structure that, it is postulated, can enhance the energy of a plasma for causing volumetric material removal. Both the Type "A" and "C" systems utilize the same gas source 50 for introducing the neutral gas volume to working surface. The Type "C" system also is coupled to controller 45 and electrical source 60 (second energy source) as described above that allows for the time-controlled and volume-metered introduction of the neutral gas volume (media $m_2$) to the working end. All parameters of electrical energy delivery may be programmed to generate trains of energy applications to the targeted site ts at selected repetition rates, or in a continuous mode, as described in the Type "A" system above.

A. Intense Pulsed Electric Discharge Mode of Operation of Type "C" Working End

Figure 10:
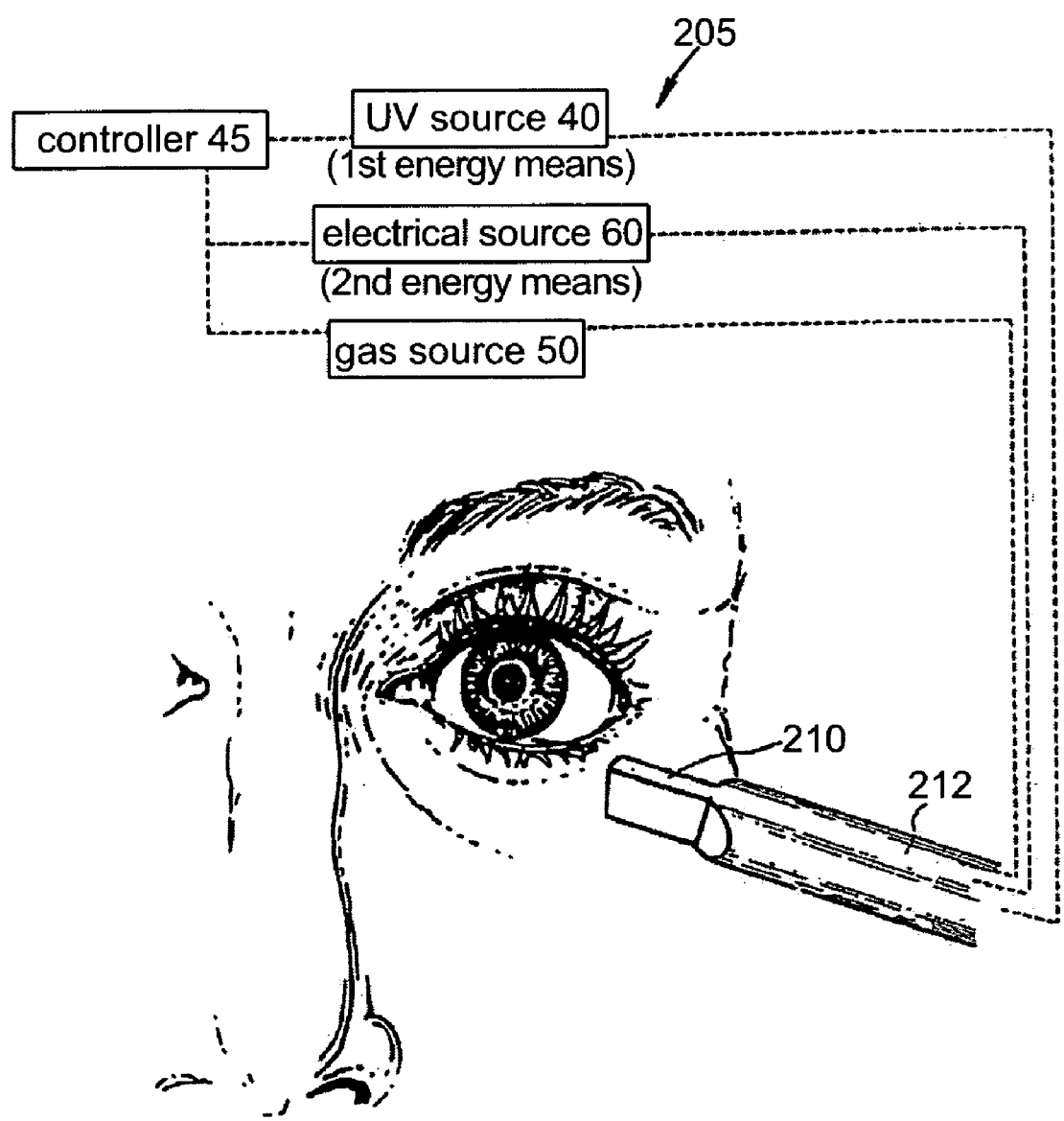
FIG. 10 is a perspective view of the working end of an exemplary Type "C" system of the invention and its use in a skin resurfacing procedure.
Figure 11:
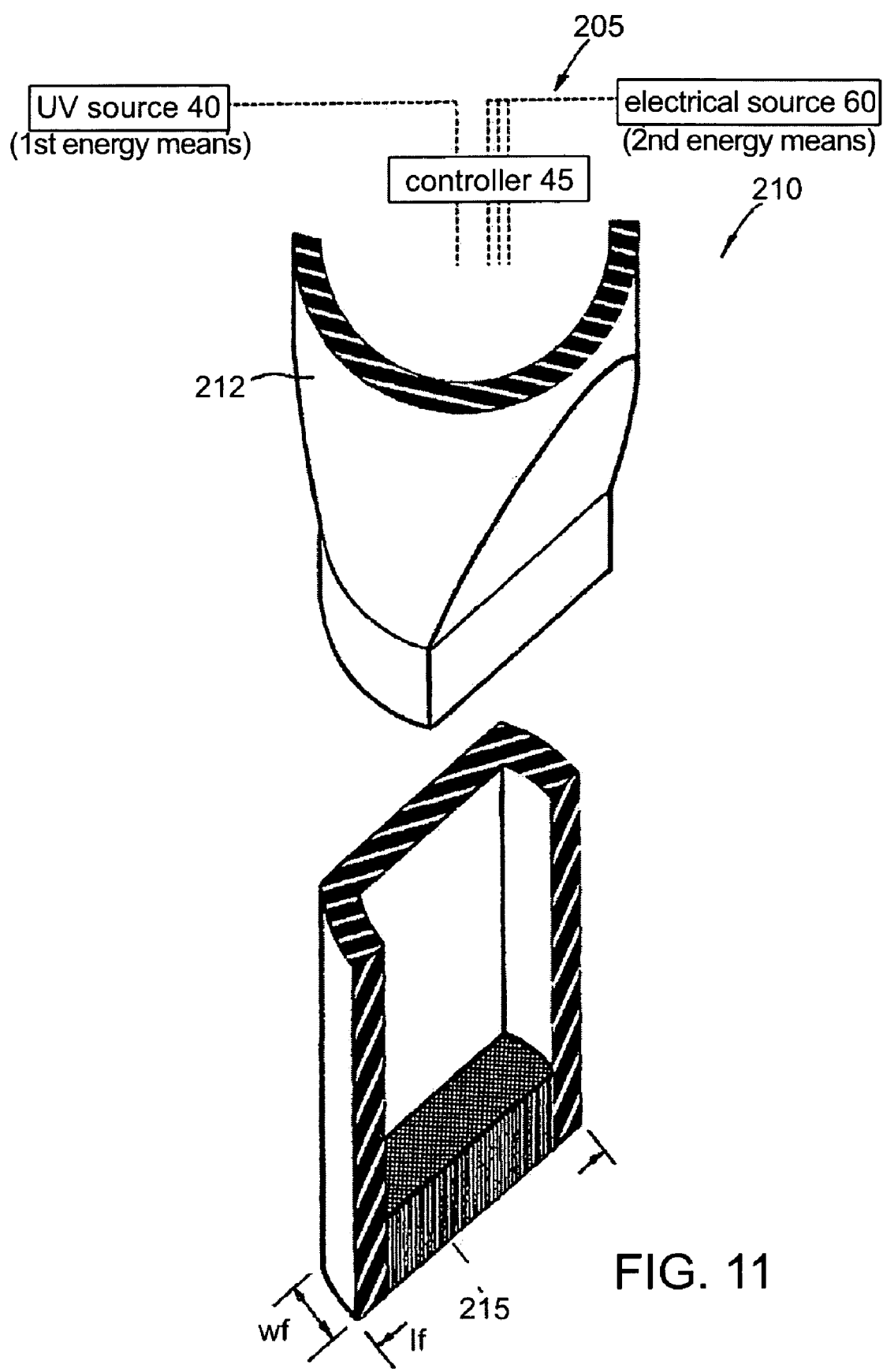
FIG. 11 is a sectional view of the working end of FIG. 10 showing the microchannel structure of the working surface and a block schematic diagram of the energy sources of the system.

More in particular, the Type "C" system of FIGS. 10 and 11 depicts an exemplary working end 210 of a probe member 212 that is adapted for use in a skin resurfacing procedure. For example, FIG. 10 shows the working end being translated over a skin surface very close to a patient's eye, which may be problematic for laser resurfacing. As will be described below, energy applied by the working surface to the skin can be modulated easily to cause very thin layer ablations for sensitive areas, such as periocular regions, in manners not possible with a laser. Also, the same instrument may deliver a first selected intensity of energy to the main portions of the patient's face, and a second selected energy intensity to periocular regions. FIGS. 10-11 show the exemplary working end with a narrow width-of-face dimension indicated at wf in comparison to a length-of-face dimension If across the working surface 215. In an instrument adapted for unidirectional translation or painting across tissue, such as in skin resurfacing, it is preferable to have such a narrow width with substantially parallel sides (transverse to the direction of translation) to control the number of successive energy-tissue interactions that occur as the working face 215 passes over any location. As will be described below, any width dimension across a working face may be defined by the number of features (or microchannels) at which a discrete energy-tissue interactions are localized.

In this Type "C" system 205, an exemplary working end 210 of a probe member 212 (see FIGS. 11 & 12) has a working surface 215 that carries a microchannel structure comprising of a plurality of channels (e.g., 220a-220d in FIG. 12) having open distal terminations 222a-222d in the working surface. The microchannel structure can be fabricated by the same processes as a micro-channel plate (MCP) or may be fabricated by a plasma-processing means known in the MEMS field (microelectrical machining). The insulator material 224 of the working surface may be glass, plastic, ceramic, a form of silicon or any other suitable material. As an example of fabricating the microchannels, a microchannel plate (NCP) is a device that is commercially available for photo-detection purposes and may be used in the present invention, both for the basic microchannel structure, and optionally for electron avalanche means as will be described below. In an MCP, a tubular cladding glass is mechanically supported in its bore by the insertion of a rod of etchable core glass to produce a potential microchannel. The assembly is then pulled through an oven and drawn down in diameter to produce a microchannel (after the core is etched away). A plurality of such drawn-down assemblies then are stacked and drawn down through the oven until a selected diameter is achieved for the core. Thereafter, the assembly is fused together and the cores are etched away leaving the microchannel structure. While commercially available MCP's typically may have channels or capillaries ranging from about 5_m and 25_m in diameter, for photodetection purposes, it can be seen that any suitable diameter of channels can be fabricated by the above methods. Another manner of fabricating the microchannel structure of the present invention is to use conventional semi-conductor processing methods to create both the microchannels in an insulator material and the electrode layer arrangements as will be described below.

Figure 12:
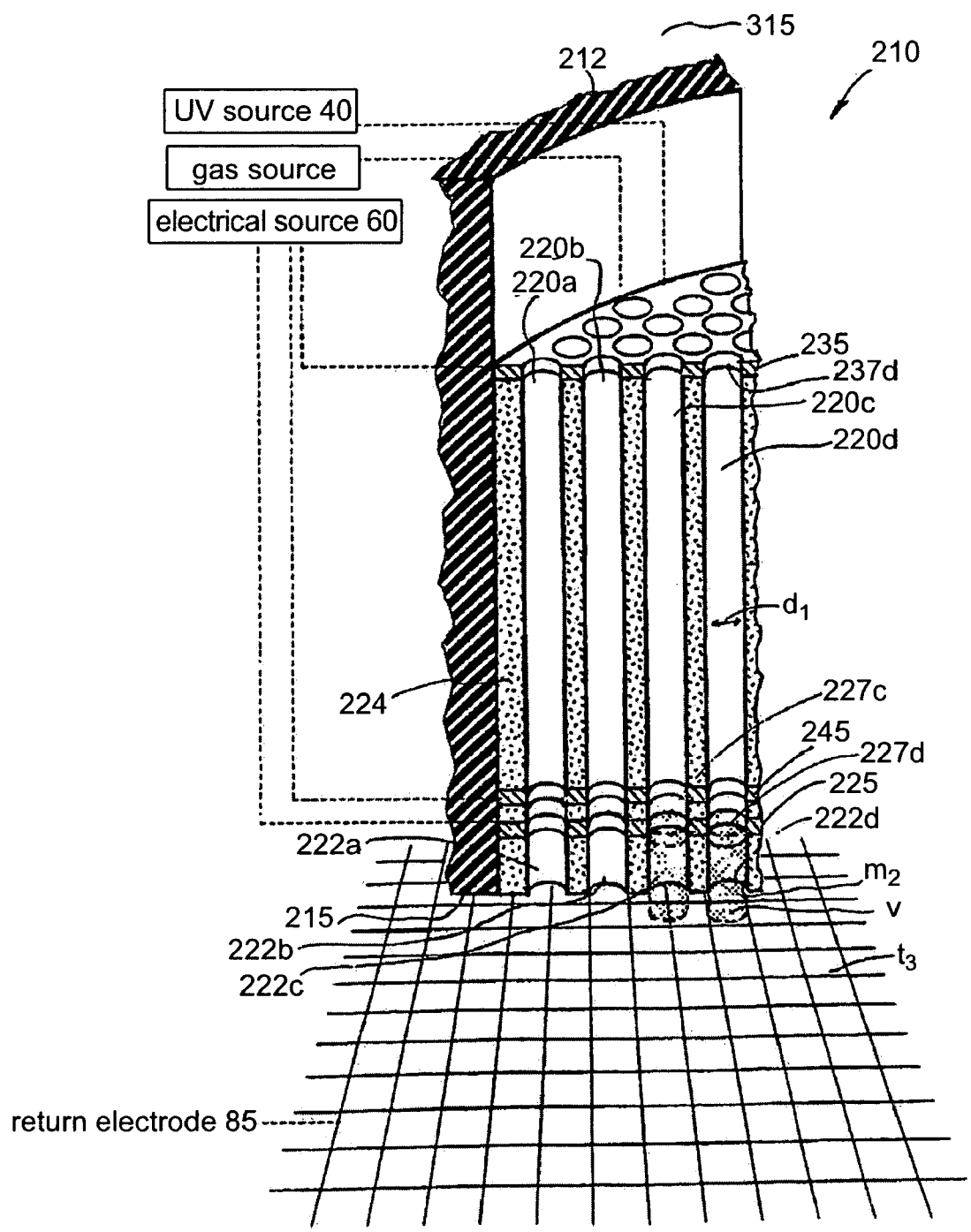
FIG. 12 is a greatly enlarged sectional view of the working end of FIG. 11 showing the microchannel structure of the working surface in more detail.
Figure 13:
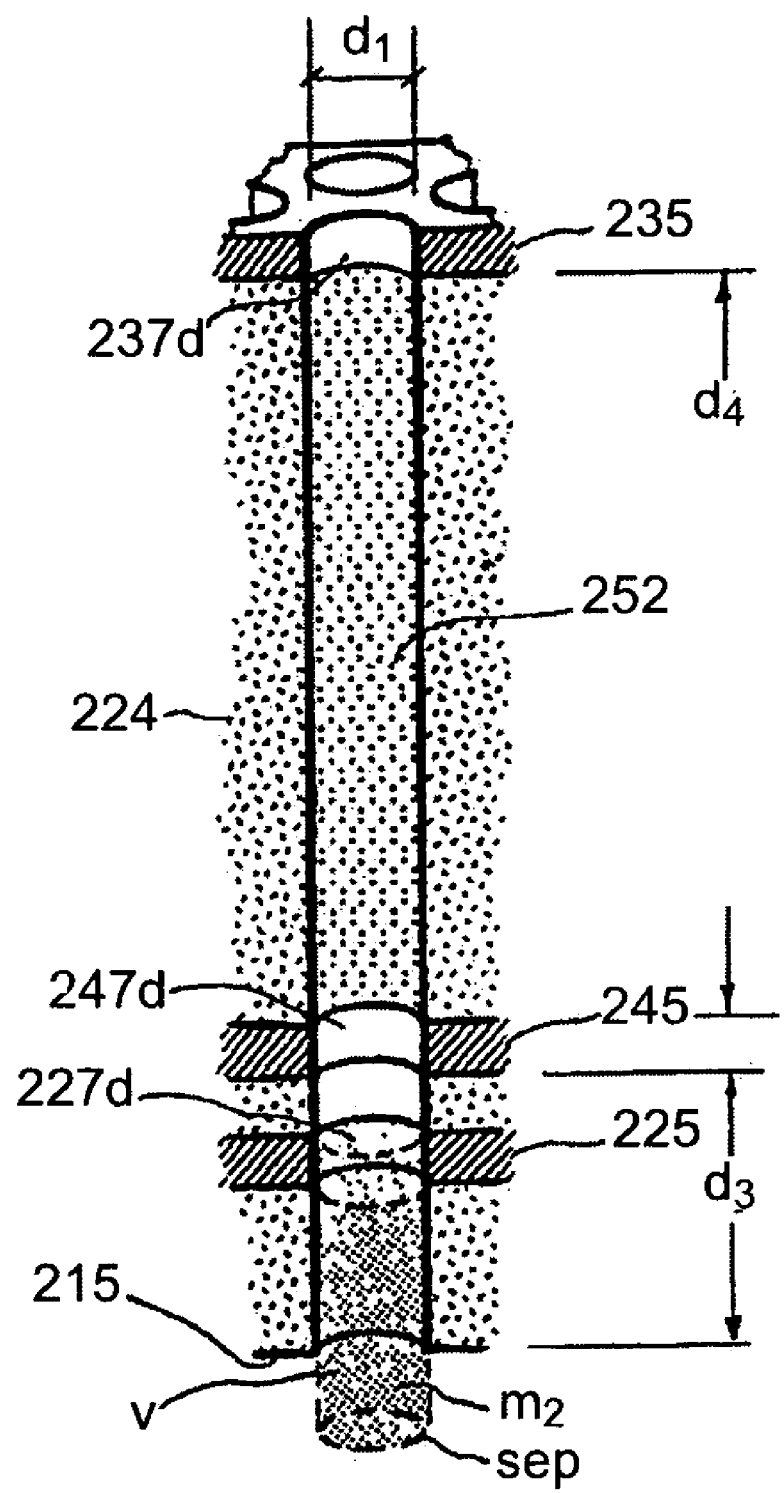
FIG. 13 is an enlarged sectional view of a single microchannel similar to FIG. 12 showing an optional electronemissive coating added to the proximal region of the microchannel structure.

In FIG. 12, an enlarged sectional view of a very small portion of the microchannel structure shows several microchannels with open distal terminations 222a-222d in the working surface 215. In any embodiment, an electrode arrangement or layer indicated at 225 (also called the ablation electrode) is provided with exposed surfaces 227a-227d that interface with volumes of media $m_2$ (a gas described in detail below) contained within the microchannels to thereafter apply energy to tissue. In this exemplary embodiment, a microchannel at its open end has a cross-section that is less than about 500 µm. More preferably, the microchannels or chambers portions have a selected cross-sectional dimension at the open terminations 222a-222d in that ranges from about 5 µm to 400 µm (see FIG. 13). Still more preferably, the microchannel open terminations 222a-222d range from about 25 µm to 200 µm. The open terminations are spaced apart by an insulator portion 224 ranging in dimension from about 5 µm to 500 µm. In any Type "C" embodiment, the electrode exposed surfaces 227a-227d are spaced inwardly or proximal from the distalmost working surface 215 a selected dimension $d_2$ that ranges from about 5 µm to 500 µm, in general varying in dimension in direct proportion with the cross-section of the channel and the voltage levels used. In other words, the electrode exposed surfaces 227a-227d have a covering layer of insulator material 224 that prevents direct contact of any electrode with tissue in contact with the surface 215.

Figure 14A:
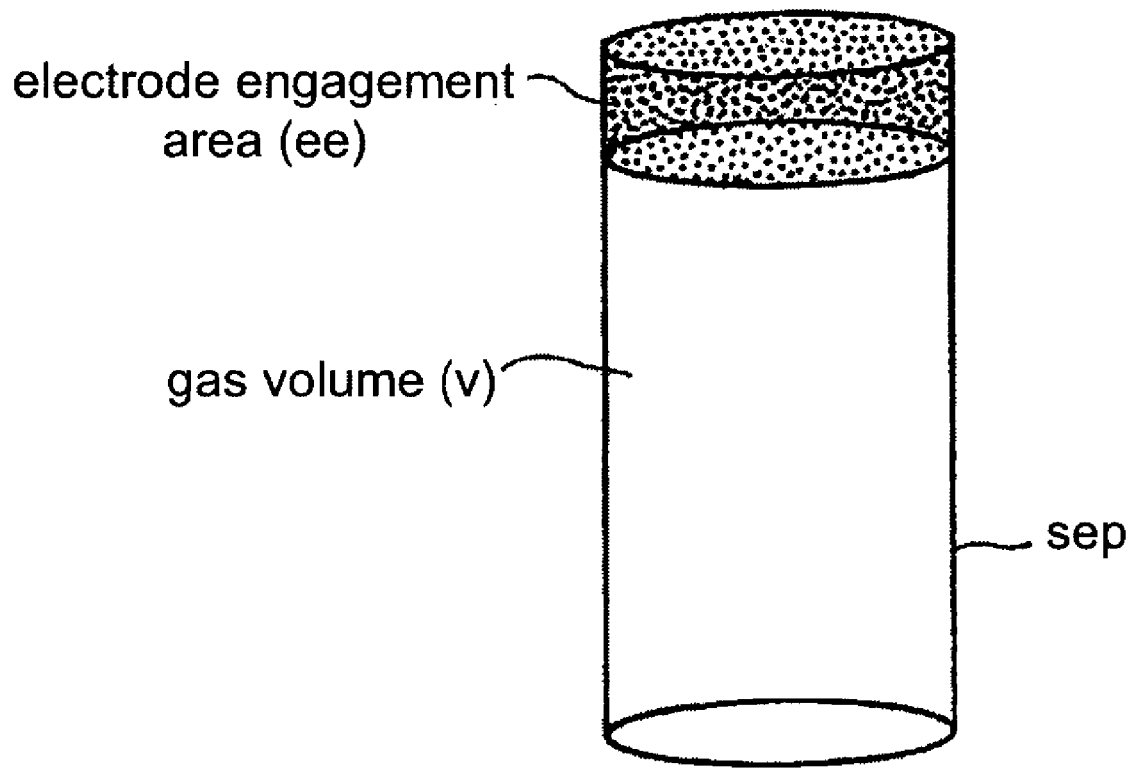
FIG. 14A is a view of an exemplary micro-scale gas volume without the surrounding structure of the working surface that illustrates a surface engagement plane about the volume and the area that engages an electrode.
Figure 14B:
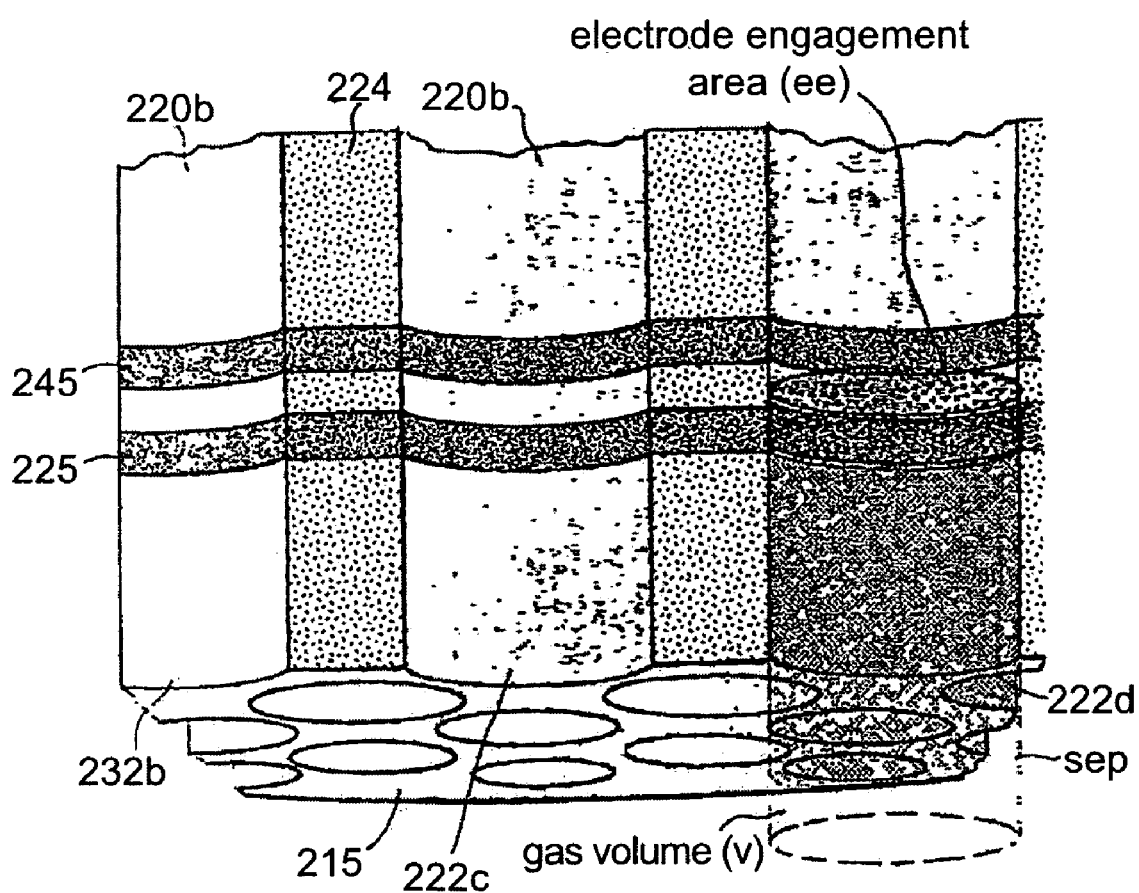
FIG. 14B is another view of the exemplary micro-scale gas volume of FIG. 14A shown in a relation to a microchannel with a surrounding gas environment also depicted graphically.

In FIG. 12, an objective of the invention is illustrated wherein a particular volume of media $m_2$ is shown captured in the distal portion of two channels 220c and 220d. The method of the invention creates the discrete transient media volumes indicated at v, and thereafter ionizes and deionizes such volumes v, within microsecond intervals to controllably cause electrical energy to cross the media volume v from an electrode exposed surface (e.g., 227a-227d) to the targeted site ts. In FIG. 12, the media volumes v are shaded to indicate an ionized condition as would occur when UV light is radiated through a light-channel 35 within member 212 exactly as described in the Type "A" embodiment (see FIG. 5C). For purposes of explaining the method of the invention, FIG. 14A shows the media volume v independent of the working end structure wherein the exterior boundary of the media volume v in herein termed a surface engagement plane sep wherein the media surface engages both the exposed electrode surface (e.g., 227a-227d) and targeted tissue ts to deliver energy to tissue. FIG. 14B shows a single media volume v in a perspective view of an end portion of a microchannel 220c. In FIGS. 14A-14B and subsequent Figures, the media volume v is illustrated with a proximal surface portion (with hatched graphics) that is in contact with the electrode surfaces (e.g., 227a-227d of FIG. 12) herein called an electrode engagement area indicated at ee. In this disclosure and other applications cross-referenced herein, the concept of controllably forming a volume v or bubble of media $m_2$ between an electrode surface and a precisely localized target site ts is a key component of the method of the invention. FIG. 12 shows the targeted site ts as a grid of arbitrary units, for example at the smallest scale from about 5 µm to 10 µm, in which the volume v engages or contacts the targeted site ts at a precise location to thereafter cause an energy-tissue interaction eti proximate to the microchannel-open termination 222a-222d that will approximate the cross-sectional dimension of that microchannel termination.

As can be seen in FIGS. 11-12, two other paired electrode layers 235 and 245 are provided having electrode exposed surfaces 237a-237d and 247a-247d within the microchannels, respectively. This electrode pair, and more particularly electrode 245, is spaced apart from electrode layer 225 by a suitable thickness insulator layer 224 to prevent the possibility of unwanted electrical interactions between electrode layers 225 and 245. The electrode pair 235 and 245 cooperate with each other to perform an optional method of the invention that utilizes high voltages described below, and thus the distal electrode 245 is spaced a selected dimension $d_3$ from the distal working surface 215 to prevent an electrical discharge to the targeted site ts from electrode 245 (see FIG. 13). The electrode layers 235 and 245 are spaced apart a selected dimension indicated at $d_4$ for causing an intense electrical field between the electrodes that cooperate with an electron-emissive surface coating 252 in the microchannel interior further described below. All electrodes 225, 235 and 245 are coupled to the electrical source 60 by separate leads. The use of electrodes 235 and 245 offer an optional enhanced mode for applying energy delivery to the targeted site ts (described below). In a basic energy delivery modality, the photoionization means and single electrode layer 225 can be utilized to cause precise volumetric tissue removal, which is similar to method performed by the Type "A" system in FIGS. 5A-5E above and is briefly described next.

Figure 15A:
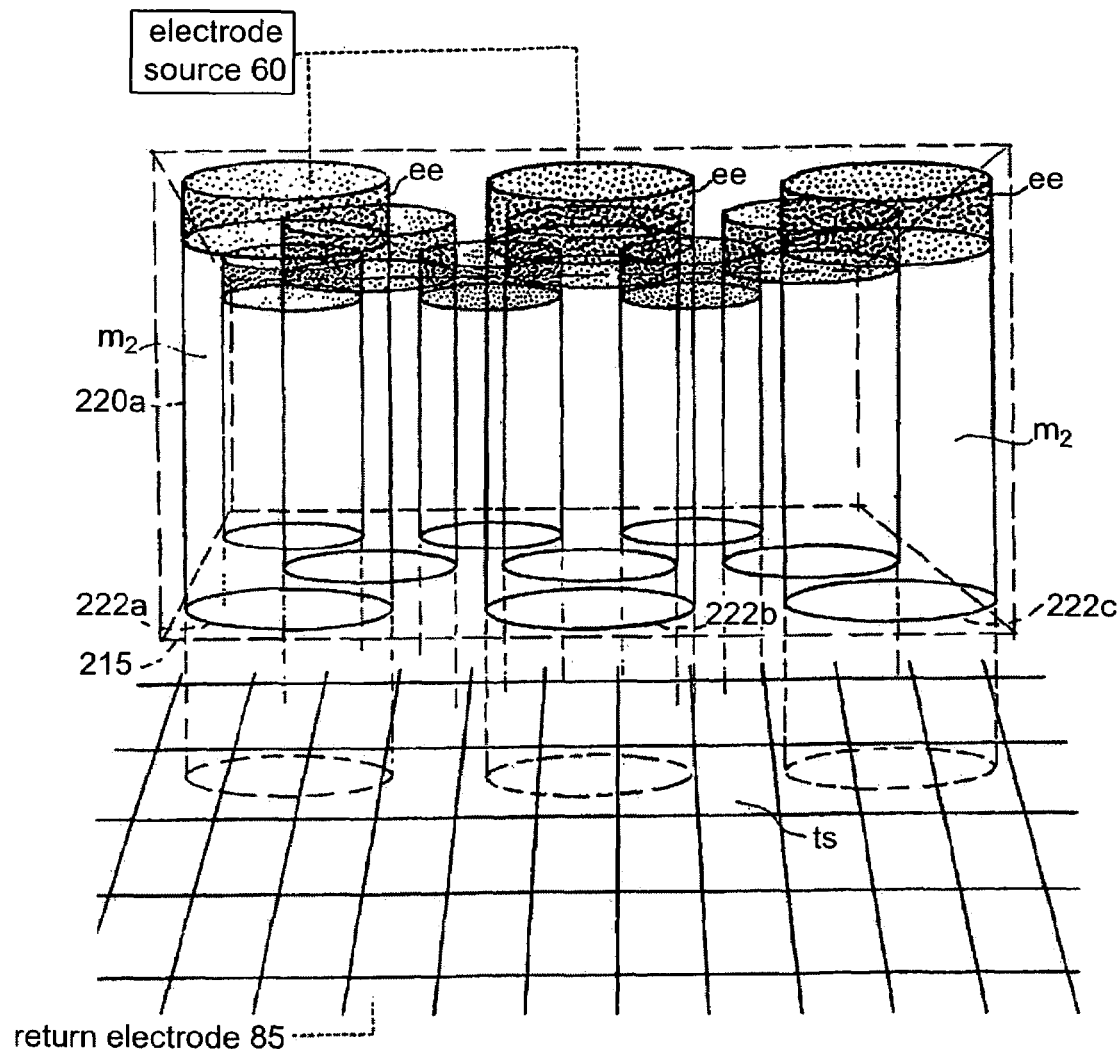
FIGS. 15A-15E are views of a first mode of practicing the principles of the invention with the Type "C" system of FIGS. 11-12.
Figure 15B:
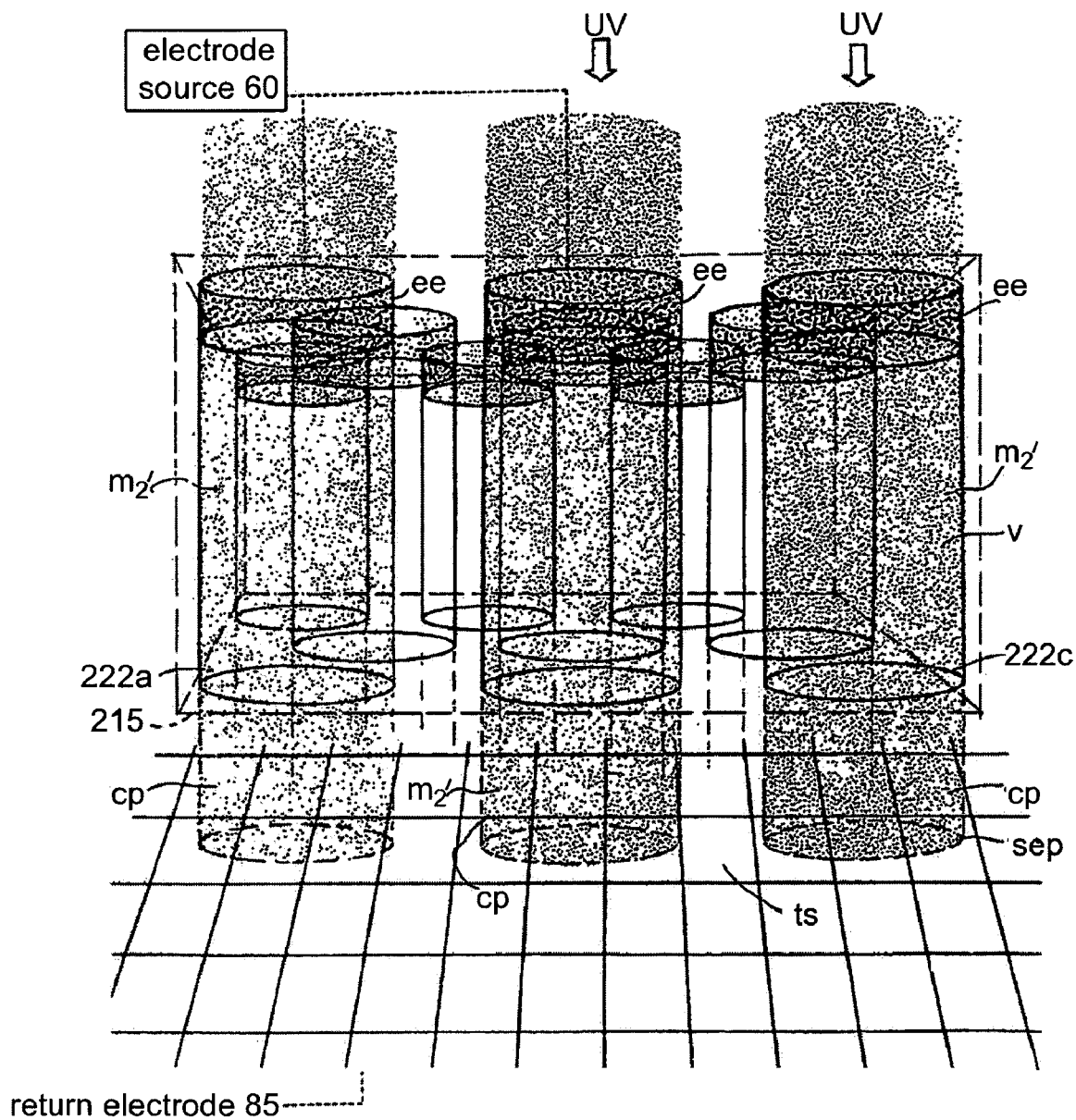

In a first operational mode of the working end 210, FIGS. 15A-15E graphically depict the use of the instrument and its distal working surface 215 to volumetrically remove surface tissues by causing a plurality of discrete and spaced apart, micro-scale, precisely localized energy-tissue interactions eti or ablations. FIG. 15A-15B show a perspective view of view three adjacent media volumes v within the working surface 215, microchannels 220a-220c and open terminations microchannels 222a-222c in phantom view. The open terminations 222a-222c are within a dimensional range r of the surface of the targeted site ts which again is graphically illustrated in a grid measured in arbitrary units. Of interest, the range r is defined as a particular dimension that is achievable by the method of the invention for creating a directed path or conductive path cp of electrical energy irradiation beyond the working surface 215 to deliver energy to tissue. In other words, it is postulated that UV radiation through the microchannels 220a-220c will illuminate a conductive path cp extending substantially beyond the working surface 215 and within media $m_1$ (the surrounding non-conductive gas environment) to the targeted site ts. The substantial confinement of this conductive path within surrounding media $m_1$ will exist for a very brief interval before its ionization degrades and blends with the surrounding gas media ml. However, during the interval in which the conductive path is substantially intact, the path cp will direct electrical energy through the free space fs beyond the working surface to the targeted site ts. In this respect, the conductive path cp in combination with the timed delivery of electrical energy from electrode engagement region ee exhibits the key characteristics of laser beams insofar as utilized for laser-tissue interactions. That is, controlled amounts of energy can be delivered through free space to a precisely localized point on the targeted site ts. The method of the invention has a limited free space range r of energy propagation, when compared to a laser, but it is believed the invention will provide a range r that is from about 100 μm to 2000 μm for working surfaces with the larger above-specified microchannel terminations 222a-222c.

Again referring to FIGS. 15A-15B, the first Figure depicts (i) a neutral gas media such as the environment (air or $m_1$) stabilized in and about the working surface or preferably (ii) a selected biocompatible neutral media $m_2$ (e.g., $CO_2$, argon, etc.) flowing through the microchannels from a source as detailed in the Type "A" embodiment. At this point in time, or a slight time interval prior to the ionization step of FIG. 15B, electrical potential is created at the electrodes and engagement area ee (e.g., at a time $T_0$). Optionally, the electrical potential is initiated contemporaneously with the ionization step of FIG. 15B. FIG. 15B depicts the next step of the invention wherein the media volumes v that extend from the electrode engagement area ee to the targeted site ts are ionized (e.g., at a time $T_1$), which is indicated graphically by shading and further indicated as media $m_2$ being altered to media $m_2'$. In this mode of operation, the media is ionized by photoionization means (first energy source) comprising UV radiation delivered to the proximal end of the microchannel structure, based on the same means described in the Type "A" embodiment which need not be repeated. As can be seen in FIG. 15B, each open microchannel termination 222a-222c is within range r of the targeted site and the ionized media $m_2'$ extends across any freespace fs to interface with the targeted site in an area substantially equivalent to the cross section of the open termination 222a-222c.

Figure 15C:
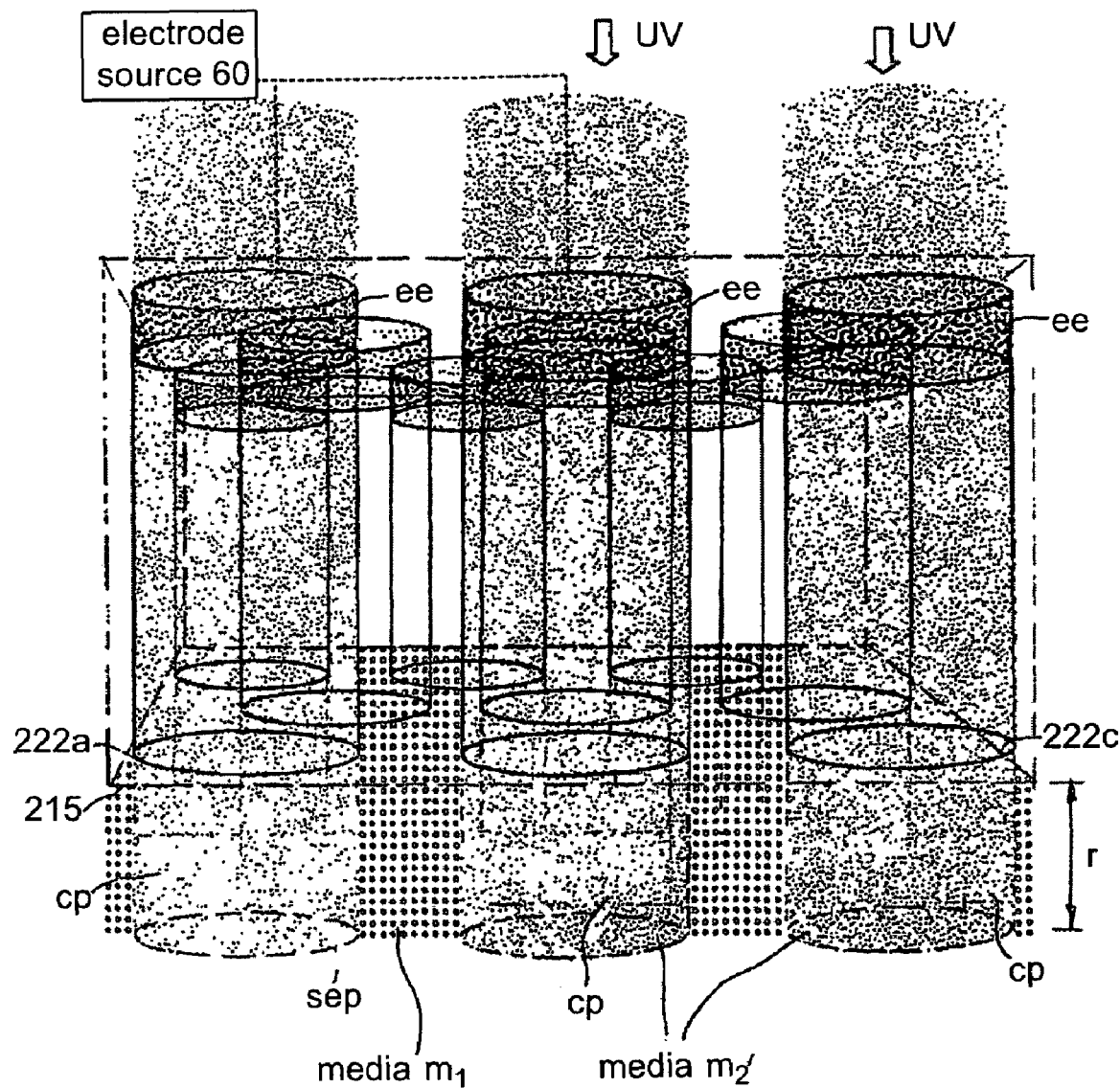
Figure 15D:
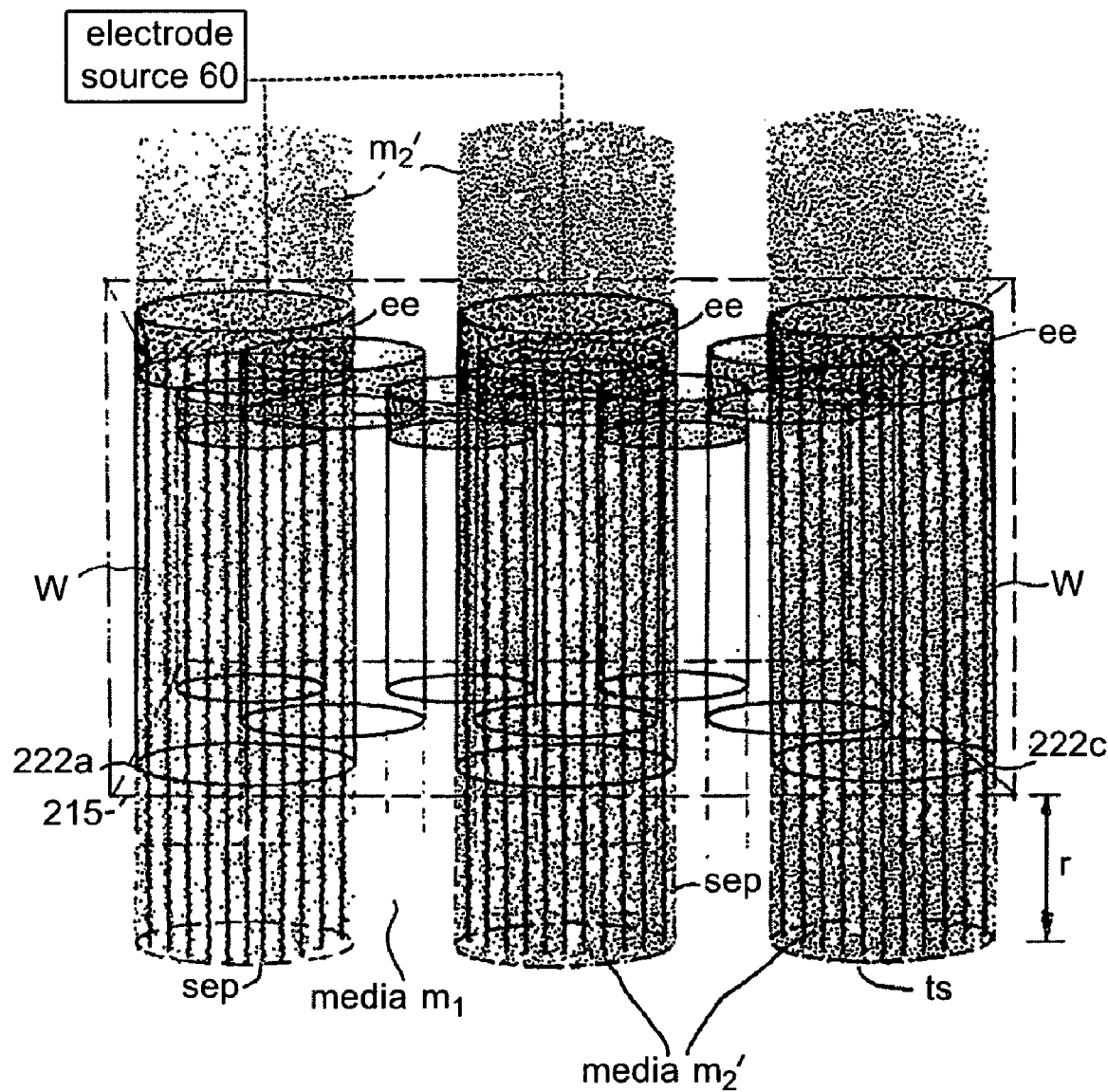

FIG. 15C shows a view very similar to FIG. 15B and depicts the range r of the conductive path cp within the surrounding non-conductive media $m_1$ that will occur for a brief interval, as described above. FIG. 15D graphically represents a result of the ionization step of FIGS. 15B and 15C wherein the now conductive media $m_2'$ of the volumes v instantly delivers electrical energy across the volumes v from the electrode engagement areas ee to regions of the targeted surface ts engaged by the volumes v. The energy application is graphically depicted by waveforms w of the electric field or discharge in FIG. 15D.

Figure 15E:
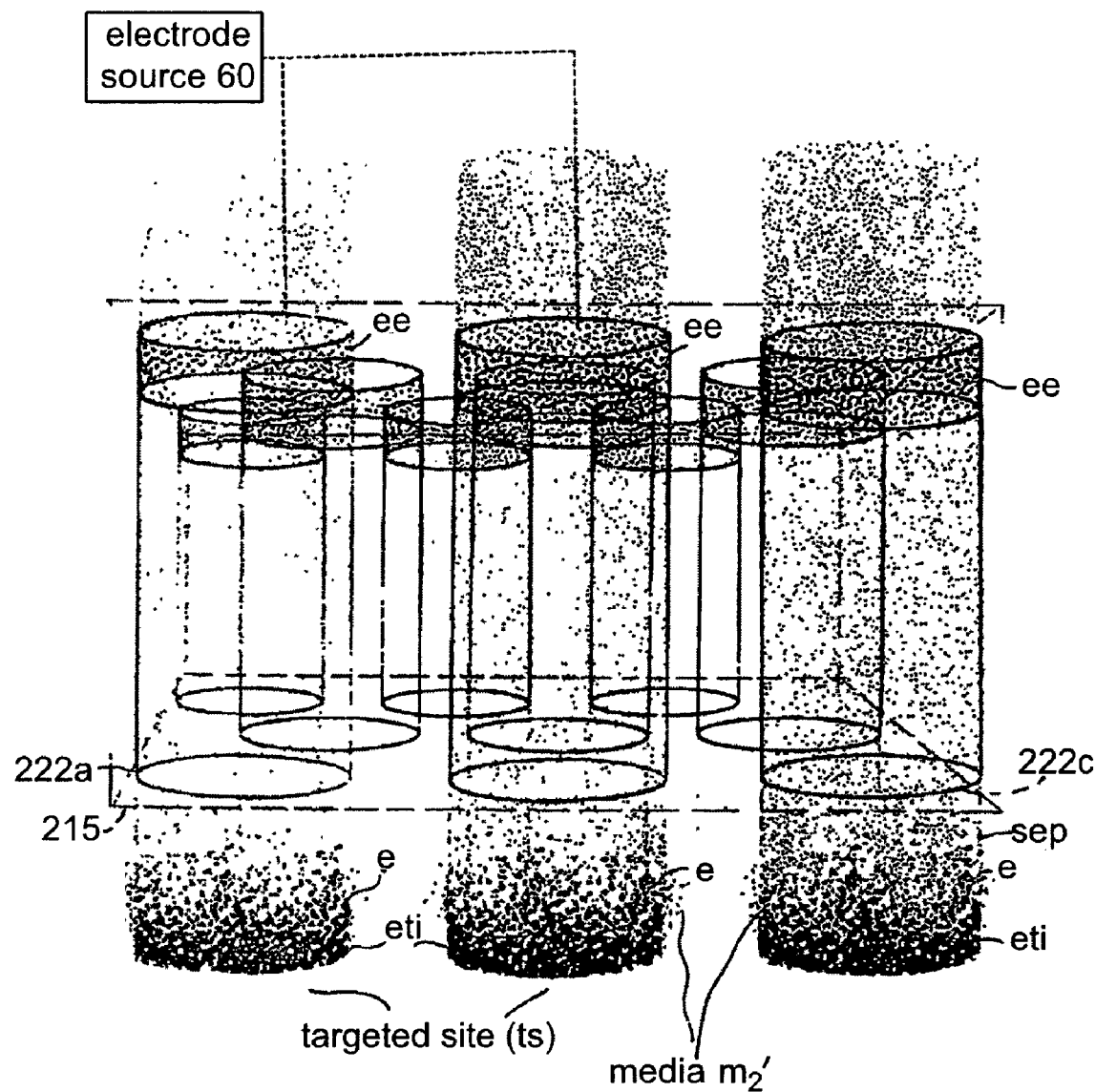

Of particular interest, FIG. 15E next graphically depicts the energy-tissue interactions eti that would occur practically contemporaneous with the energy application step of FIG. 15D. It can be seen that a series of discrete, precisely localized, time-controlled energy-tissue interactions eti or ablations will be caused by the method of the invention and result in ejecta e of water vapor and cell debris. The intense energy potential at the electrode interface ee with the gas volume v is carried to the tissue surface to cause intense energy densities that ablate tissue by vaporization of thin surface layers for the brief interval that the ionized media $m_2'$ remains.

The next step of the method of the invention (not shown) is (i) the termination of photoionizing UV radiation to the gas media in the microchannel structure thereby returning such gases to a non-conductive nature (see FIG. 15A); and optionally (ii) the continuous or pulsed inflows of the neutral gas through the microchannel structure to insure the gas volumes therein are instantly returned to neutral. Contemporaneous with this step, the electrical potential at the electrodes is terminated.

Following the above sequence of steps which occur in a micro-second time frame, the steps of the method are repeated after a very brief selected interval that exceeds the thermal relaxation of the targeted site, as described above. The time intervals for utilizing the photoionization means for switching the gas media from non-conductive to conductive may be repeated at a pulse rate between about 200 ns and 500 ms. Stated another way, the interval between repetitions of the complete steps of photoionization and electrical energy applications, may range from about 500 ns to 500 ms to insure thermal relaxation of the targeted site.

Figure 3:
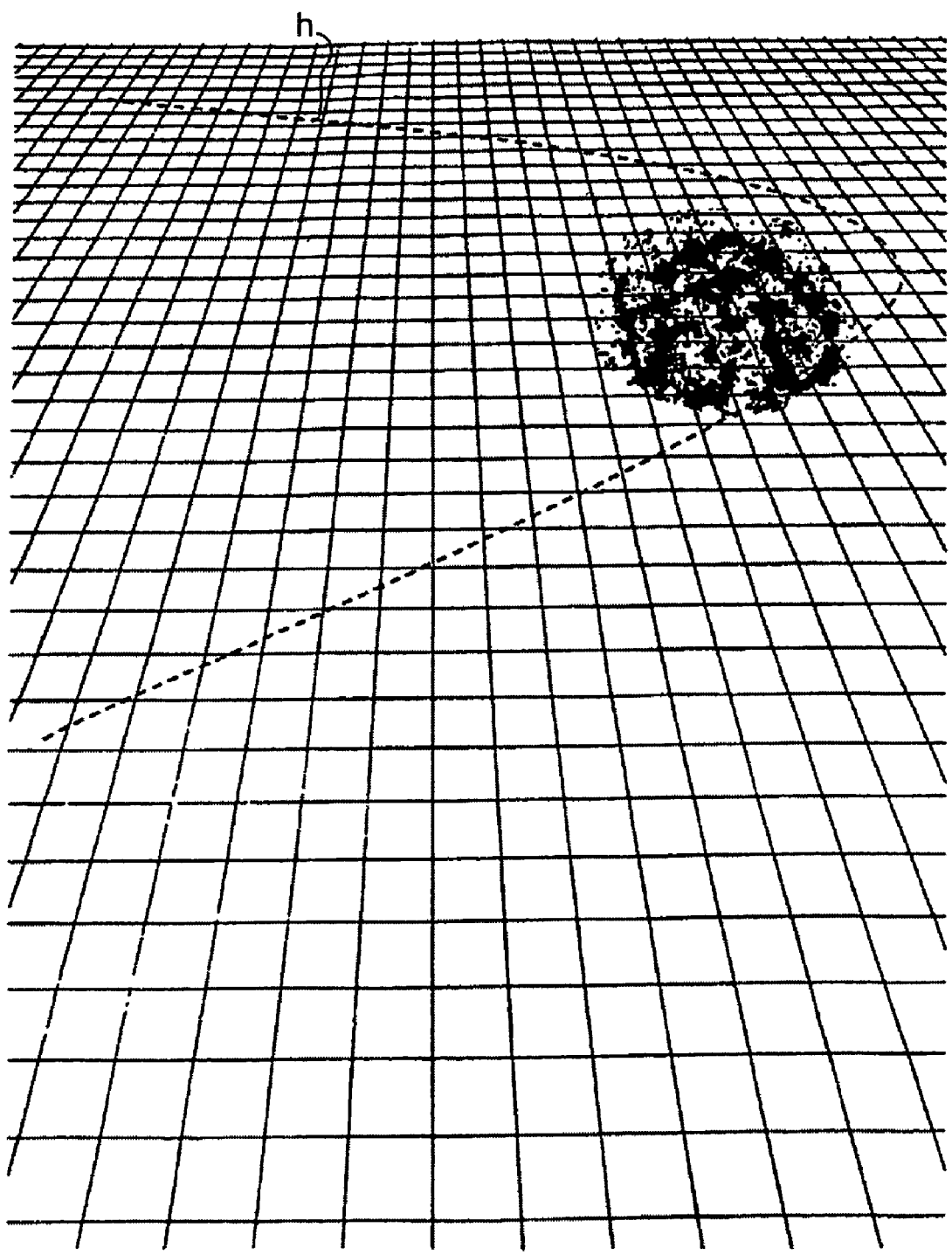
FIG. 3 is a micron-scaled grid representing a tissue surface that provides another view depicting the prior art lack of localization of an energy application event utilizing the prior art instruments of either FIG. 1A or FIG. 1B.
Figure 4:
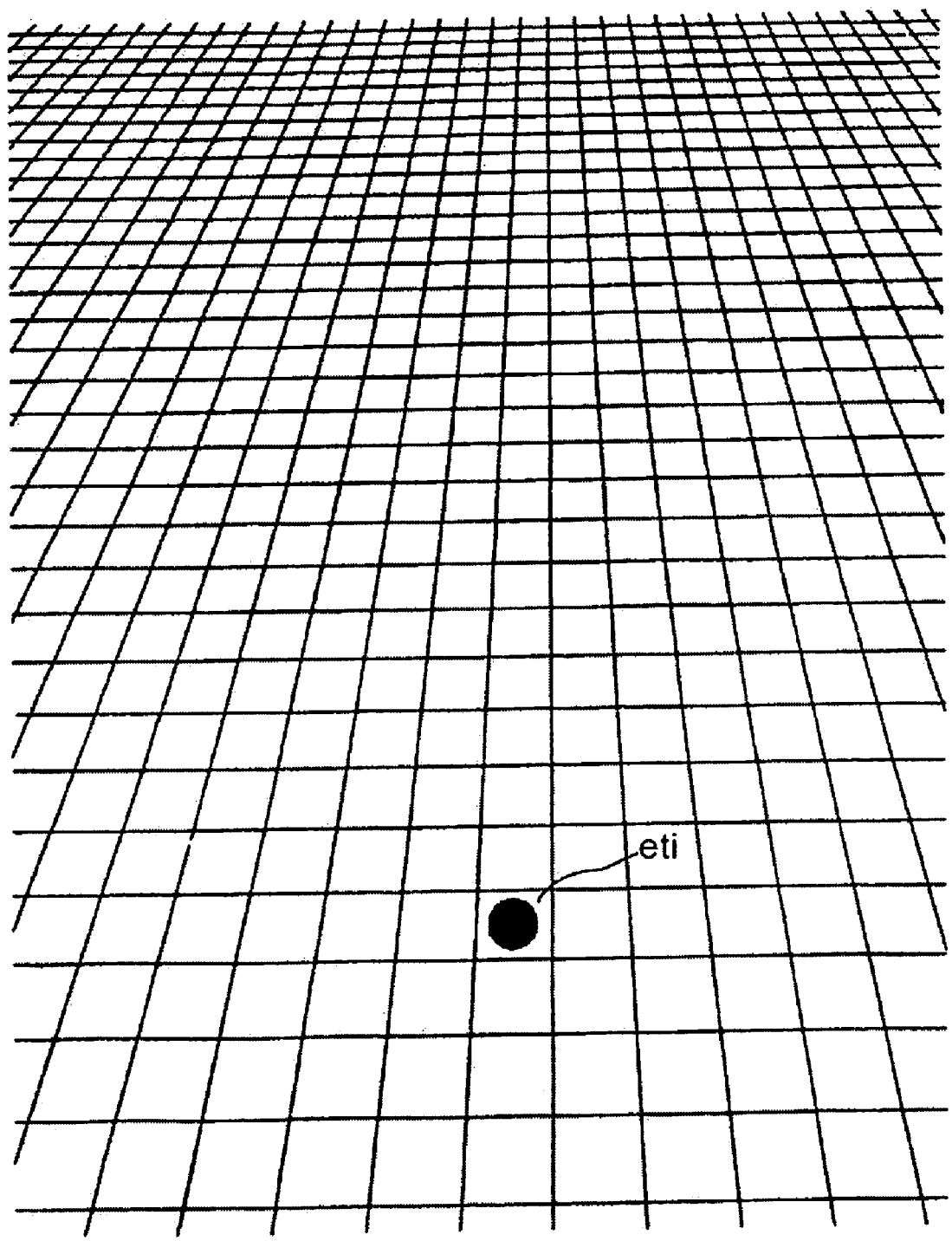
FIG. 4 is a micron-scaled grid representing a tissue surface similar to that of FIG. 3 that indicates the resolution of energy-tissue interactions that are possible with the present invention.
Figure 16A:
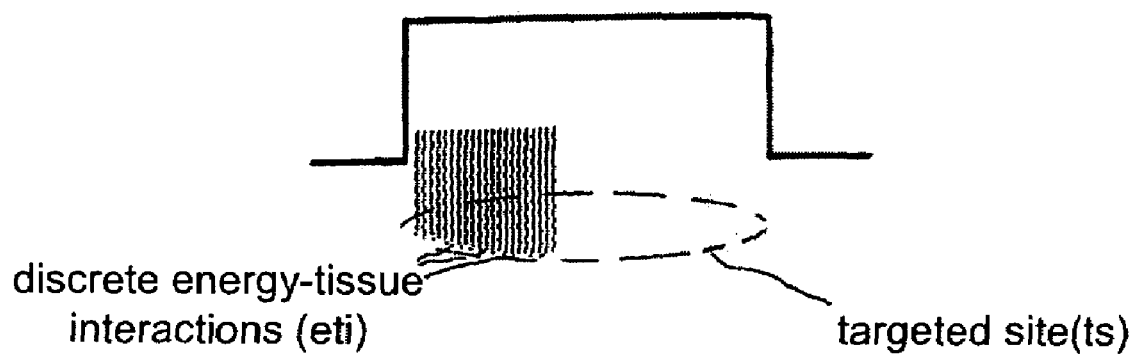
FIG. 16A is a graphical view of a "top hat" energy distribution across a laser energy-tissue interaction.
Figure 16B:
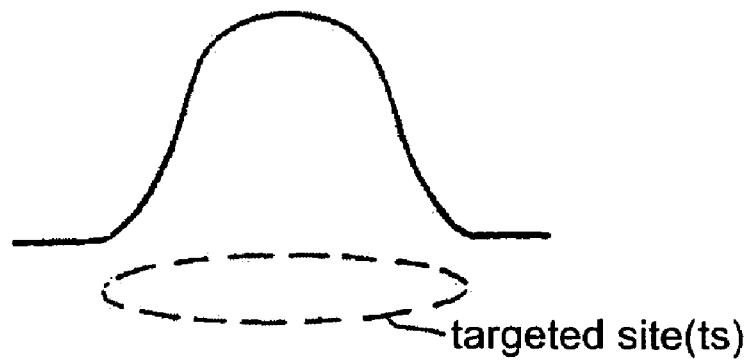
FIG. 16B is a graphical view of a Gaussian energy distribution across a laser energy-tissue interaction.

It can be seen in FIG. 15E that energy application to a targeted site ts will result in a very even distribution of energy across the site having the dimensions of the width wf and length lf of the working surface 215 (see FIG. 11). Further, it can be understood that by painting the working surface 215 across the targeted site ts, an even ablation will occur in a path due to the large number of discrete energy-tissue interaction sites eti (see FIG. 15E). In an early section of this disclosure, it was explained that in prior art ablation modalities, the distribution of energy densities and ablation effects across an energy application site were random, and the dimensions across any such energy application site also would be random due to the random size of the insulative bubble that is formed (see application of energy to tissue in FIG. 3) The working surface 215 and method of the present invention thus solve the problem of uneven and random energy distributions across a targeted site by the novel micronization means of the invention, with respect both to the feature dimensions of the working surface 215 and the resultant dimensions across a particular the energy-tissue interaction eti. By this means, an aggregation or grid of such discrete localized energy-tissue interactions eti (ablations) can be designed to comprise any desired dimension of an ablation area, for example to match the size of a prior art ablation if desired. Further, the present invention thus can be favorably compared to a laser energy-tissue interaction. In laser irradiation of a tissue surface, energy distribution across a site may be controlled largely by optics, with a desirable "top hat" energy distribution shown in FIG. 16A where energy is delivered evenly across an irradiated site, and the generally less preferred Gaussian energy distribution of FIG. 16B where higher energy densities are caused in the center of the site with a bell curve defining a taper-off of the energy delivered toward the perimeter of the site. Thus, the present invention, by distributing a large number of discrete energy-tissue interactions evenly over a particular application of energy per selected time interval at a targeted site ts, it can be said for the first time that energy can be applied to a targeted body structure from an electrical source that effectively results in a substantially even "top hat" energy distribution across the site. It is believed that working electrode surfaces with features micronized as described above to perform the novel method of electrosurgical ablation can be used advantageously in every form of electrosurgical instrument used for ablation, for example, simple mono-polar cutting electrodes, ablation catheter working ends, stereotactic needle working ends used for precise tumor ablation in the brain or breast or elsewhere, and all other ablation electrodes. The micronization of the energy tissue interactions eti also limit collateral thermal damage to the level of insignificance due to the limited depth of any application of energy that is substantially confined within very thin surface cell layers.

The working end 215 of the device of FIGS. 10-11 may further be provided with a perimeter suction channel as is known in the art (not shown) for aspirating tissue debris from the targeted site at the working end is translated over the tissue. The open apertures or apertures of such a suction channel preferably would be spaced around the perimeter or edge of the microchannel structure.

B. Alternative Energetic Plasma Mode of Operation of Type "C" Working End

The previous section described the application of high intensity electrical energy in pulses to a targeted site ts to cause volumetric material removal wherein the ablation will cause substantially little collateral thermal damage to tissue due to (i) the micron dimension of the discrete energy-tissue interactions that ablate only very thin cell layers, and (ii) the thermal relaxation of the targeted site ts between timed applications of energy at the 100's or 1000's of discrete, localized sites. It is believed that an alternative mode of operation will prove possible with the Type "C" working end in which electrical energy is delivered continuously to the microchannel structure, along with optional means of enhancing such energy delivery, to cause sustainable highly energetic microplasma volumes about the open microchannel terminations 222a-222c (see FIG. 12) capable of volatilizing surface molecules over a selected time interval to cause volumetric material removal.

Figure 17:
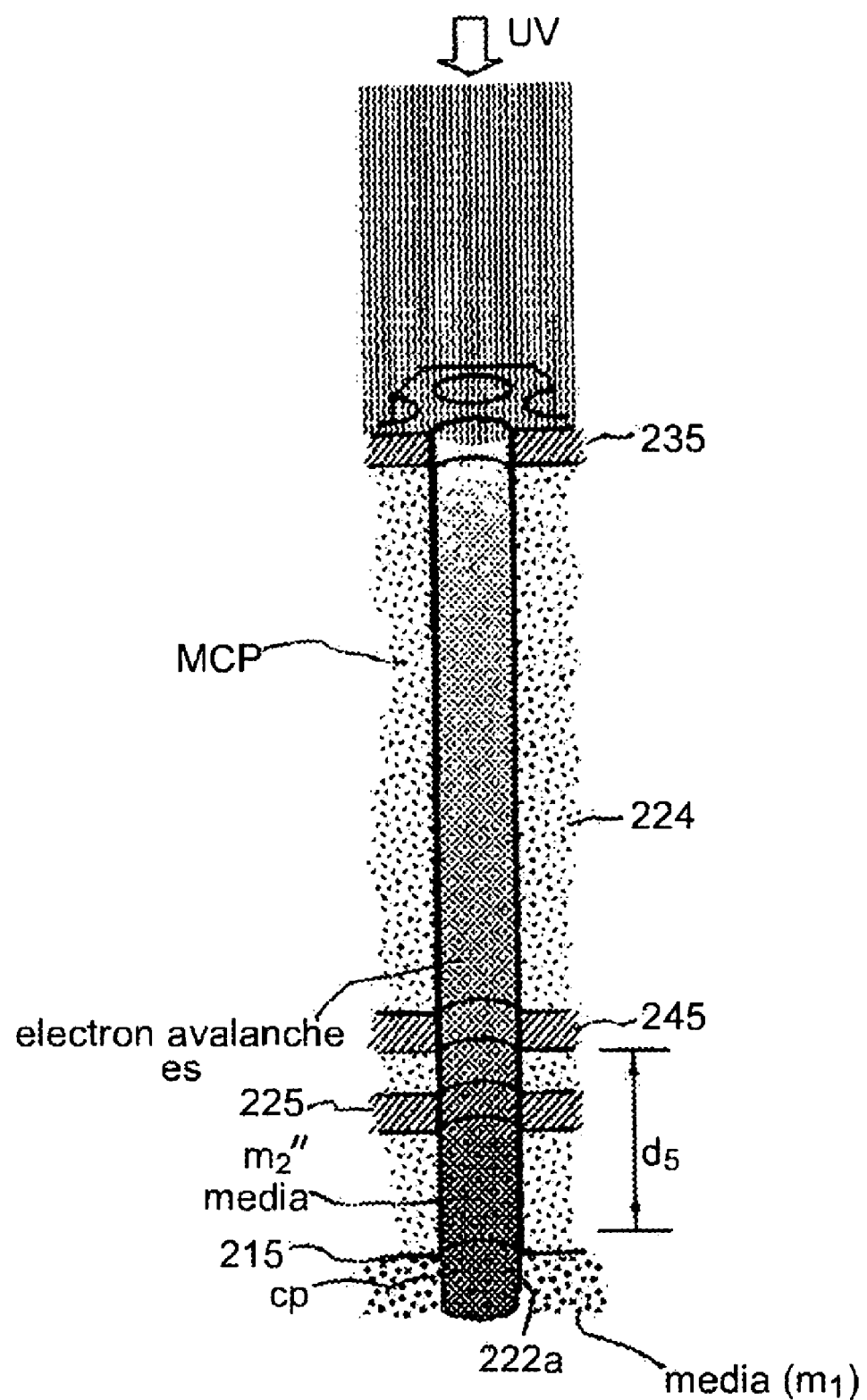
FIG. 17 is a view of a second mode of practicing the principles of the invention with the Type "C" system by utilizing electron emissions from a microchannel plate (MCP) to energize the gas volumes depicted in FIG. 11 to achieve a plasma-mediated ablation.

More in particular, referring to FIG. 17, the electron avalanche means of the microchannel plate (MCP) structure may be energized in this alternative mode of operation to create the energetic microplasma indicated at $m_2"$ (i.e., $m_2'$ identified ionized media in the previous mode of operation; $m_241$ identifies the enhanced plasma of the alternative mode) about the exemplary open microchannel termination 222a. The steps of this alternative method comprise initially delivering appropriate electrical energy to the paired electrode layers 235 and 245 of the microchannel structure, which is in the range of 100 to 2000 volts. Thereafter, the steps previously described are initiated; that is electrical potential is created at electrode 225 and then the UV source is triggered to photoionize the media volume v that is within the microchannel structure. In this case, as depicted in FIG. 17, the UV photons strike the electron-emissive surface coating 252 of the microchannels between the paired electrode layers 235 and 245 and cause an electron spray (avalanche) indicated at es wherein the electrons can freely travel the minimal distance $d_s$ to greatly increase in the free electron population of the microplasma $m_2"$ to assist in the molecular volatilization of the surface of the targeted site (see FIG. 17). In this mode of operation, the electrical potential at electrode layer 225 may be continuous rather than pulsed to maintain the microplasmas at a high intensity, and if the dimension between the open microchannel terminations 222a-222b is across and about the working surface 215 to interface with the targeted site ts. This instrument and method, it is believed, will be able to create and sustain a sufficiently energetic microplasma to cause a true plasma-mediated ablation of tissue at voltages at electrode 225 in the range of 100 V to 600 V. At these sufficiently high energy levels (or voltage V), it is believed that energy in the range of 3.0 eV to 8.0 eV can be created to cause breakdown of the carbon-carbon bonds, carbon-nitrogen bonds, and other similar bonds in surface molecules. When comparing the system disclosed by Eggers et al (U.S. Pat. Nos. 5,873,855; 5,888,198; 5,891,095; 6,024,733; 6,032,674; 6,066,134) and commercialized as the Coblator™ system, it can be easily understood this prior art system expends much of its available energy to continuously thermally vaporize random elements (NaCl) within a cool liquid to produce random insulative gas bubbles over and about a large working end, which bubbles thereafter are ionized randomly by an intense electrical discharge therein and there across. In contrast, the present invention expends no energy to vaporize a liquid to produce the required gas volumes. The present invention independently produces and introduces a neutral gas into the working end. Further, the present invention utilizes both photoionization means and an optional electron avalanche means to energize the plasma volumes. Still further, the microplasma volumes are captured within the microchannel structure and such micron-sized volumes can efficiently sustain an energetic plasma.

Figure 18:
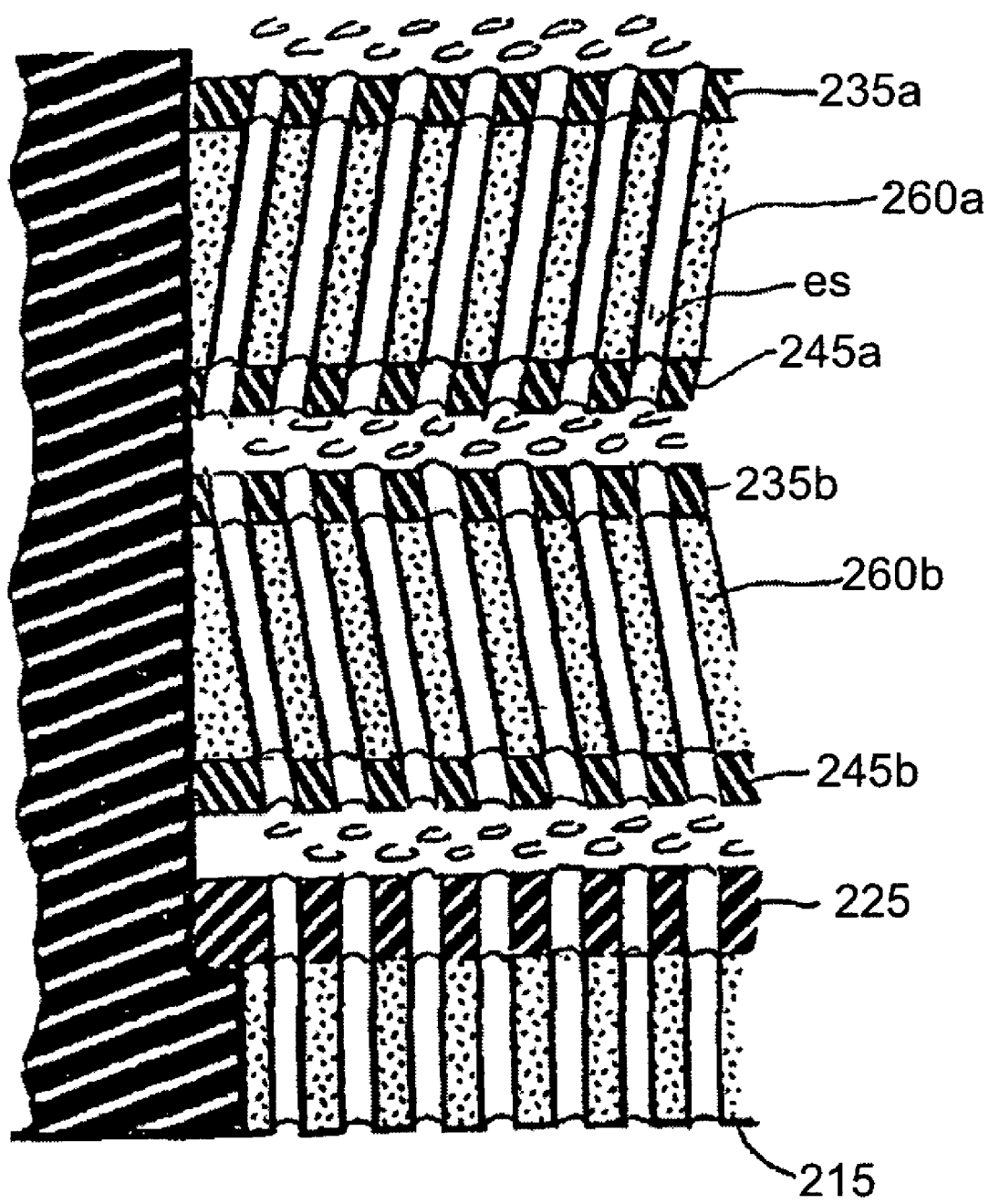
FIG. 18 is a view of an alternative embodiment of working end for practicing the method of FIG. 17 in which multiple MCP's are arranged in a chevron pattern to further enhance an electron avalanche in plasma volumes.

FIG. 18 illustrates a variation on the Type "C" working end of FIG. 17 that provides a multiple layer MCP structure, in an optional chevron configuration, to further enhance the electron population of the microplasmas $m_2"$. The working surface 215 again carries the same electrode 225. A first microchannel plate (MCP) layer (not-to-scale) indicated at 260a has paired electrode layers 235a and 245a that function as previously described. A second MCP layer (not-toscale) indicated at 260b has paired electrode layers 235b and 245b. There may be further layers, and the purpose of the chevron pattern is cause the electron spray es from a more proximal layer to strike the walls of the more distal microchannel at an angle to thereby increase electron emissions.

C. Alternative Field Ionization (FI) Mode of Operation of Type "C" Working End

The previous sections have described the method of using a Type "C" working end wherein the ionization means comprise a light-carrying channel 35 and a UV source to deliver energy to the working end. Other ionization means independent of the ablation electrode 225 are possible have been disclosed (see, e.g., co-pending U.S. Ser. No. 09/317, 768 filed May 24, 1999(Docket No. S-QP-002) titled Photoionized Gas Enabled Electrical Discharge Technique for Plasma-Mediated Cold Tissue Ablation) and are listed again in the first paragraph of Section V above. There may be requirements for certain instruments that make it difficult or expensive to rely on light-channeling means 35 to deliver UV energy to a working surface. For example, it may be difficult to fabricate a light channel in an elongate catheter having a very small diameter. Also, it may be expensive to fabricate a light channel in an elongate introducer member in which the axis of the microchannel structure is transverse to the axis of the introducer.

For this reason, a working surface 215 with microchannel structure substantially the same as depicted in FIG. 12 may be used without photoionization means. Instead, the paired electrode layers 235 and 245 with exposed surfaces 237 and 247 within microchannels 220a-220d (absent electron-emissive coating 252) may be used to cause field ionization of an introduced neutral gas, with the other steps of pulsed energy delivery to cause tissue ablation the same as described previously (see FIG. 19D).

Figure 19A:
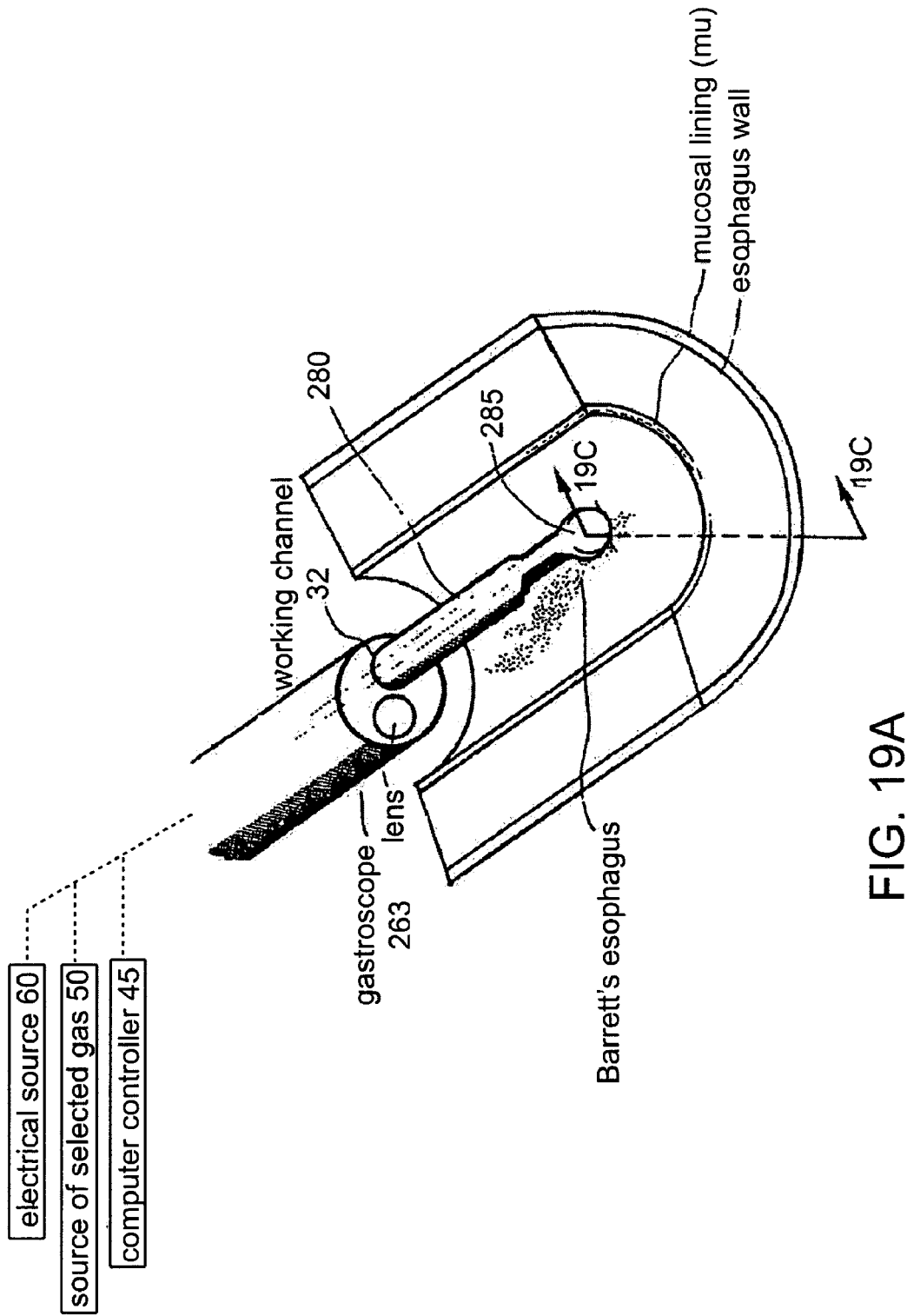
FIG. 19A is a view of the distal end of another probe member that carries a microchannel plate structure similar to that of FIG. 11, this time utilizing field ionization of captured gas volumes, the working end adapted for thin layer ablation of mucosal layers.
Figure 19B:
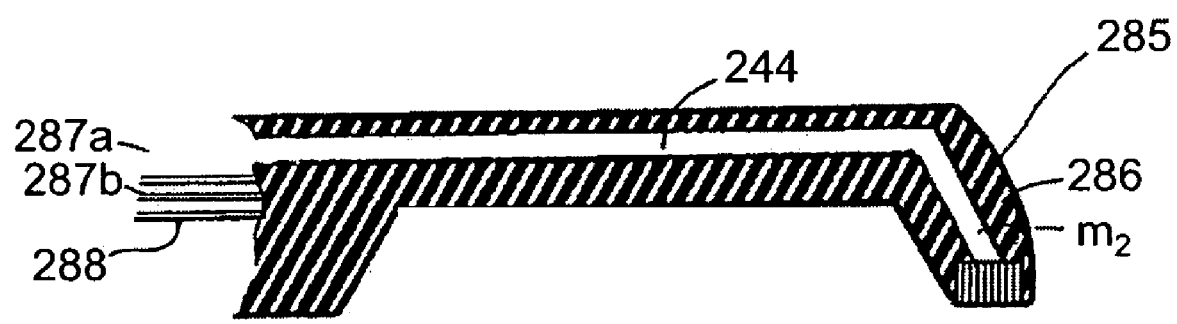
FIG. 19B is a sectional view of the distal end of the probe member of FIG. 19A.
Figure 19C:
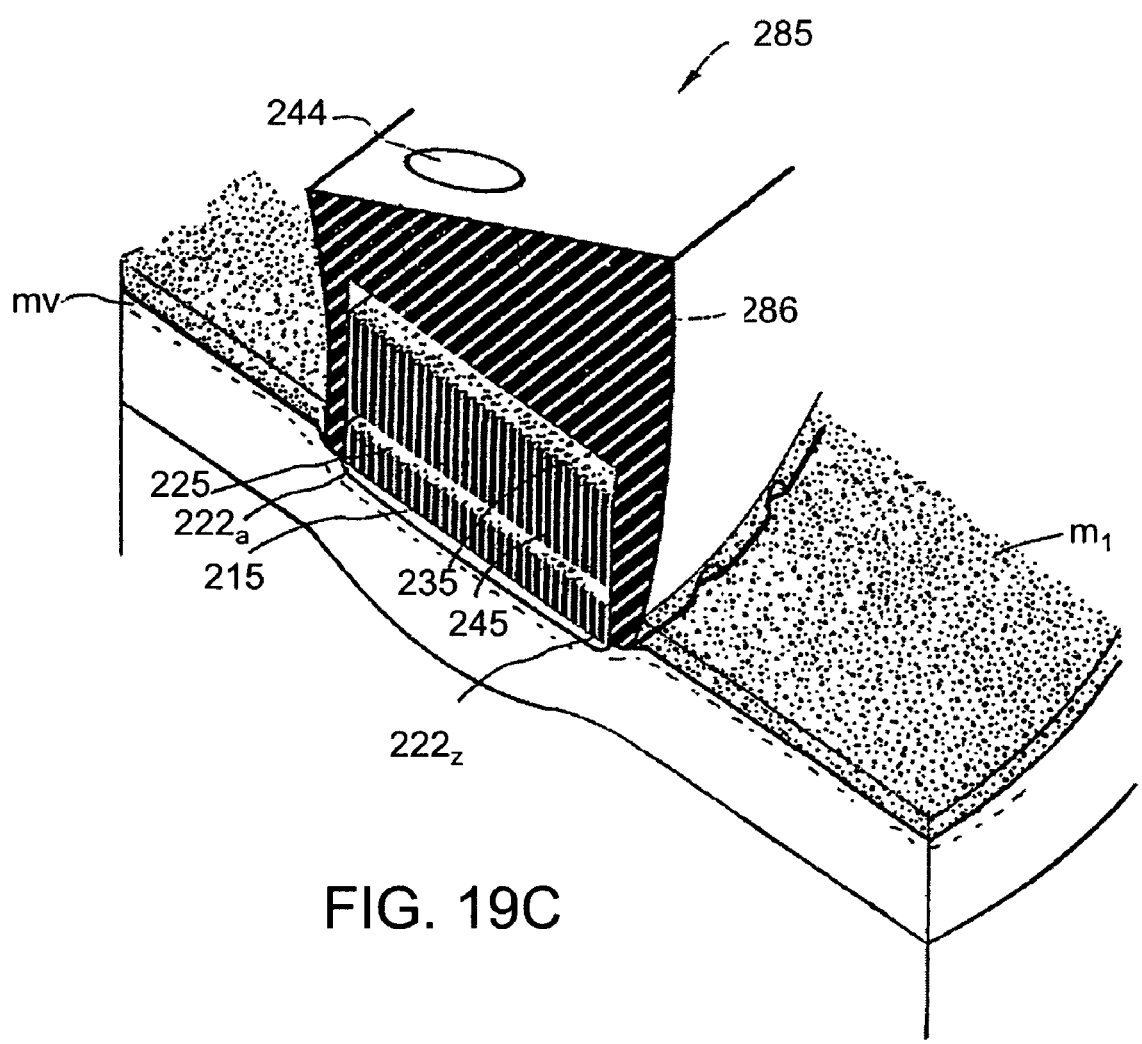
FIG. 19C is a greatly enlarged sectional view of the working end of the probe member of FIG. 19B showing the microchannel structure.
Figure 19D:
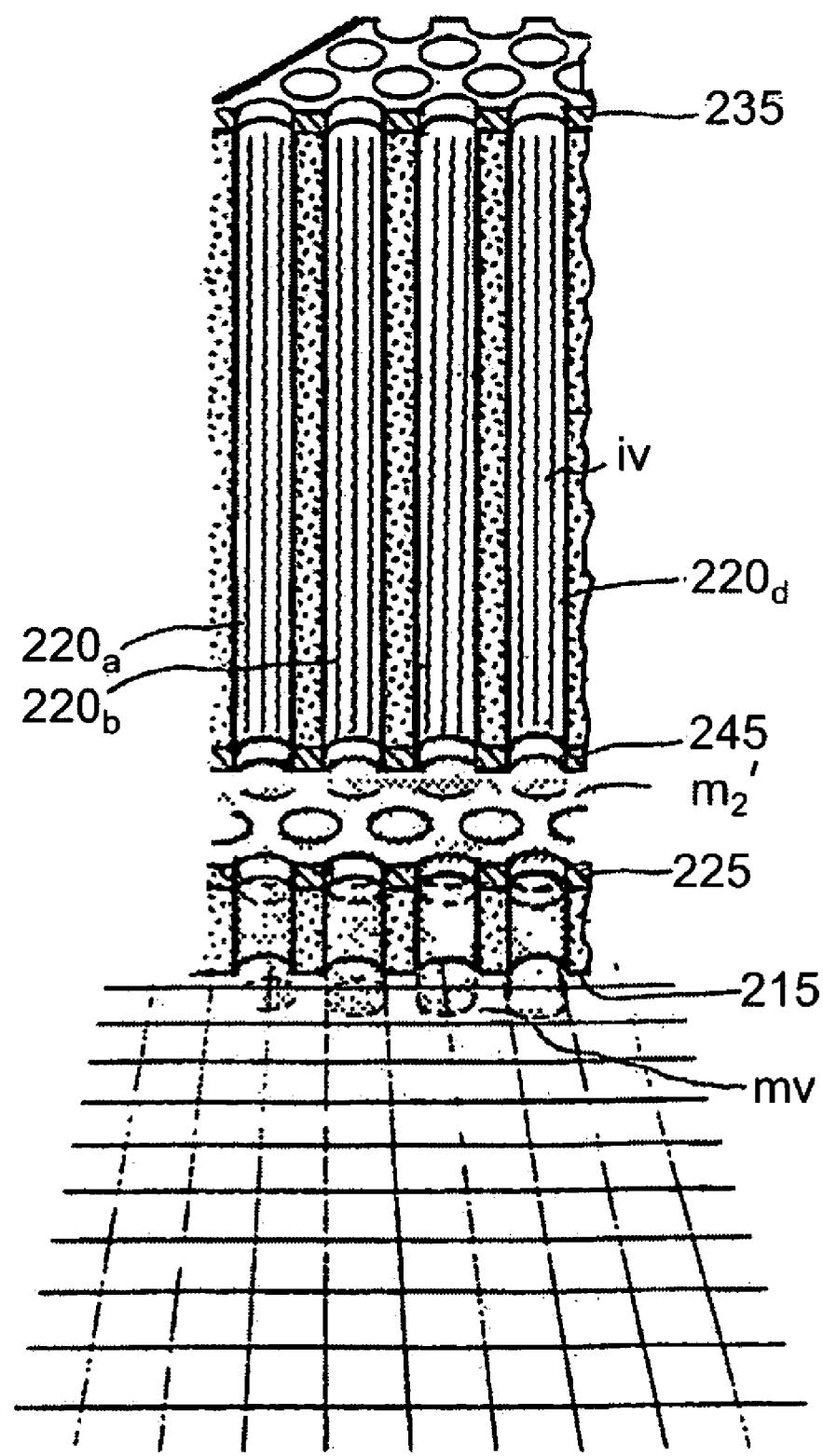
FIG. 19D is a view of practicing the principles of the invention with the working end of FIG. 19C using field ionization means to switch the gas volumes flowing through the microchannel structure between conductive and nonconductive states.

Referring to FIGS. 19A-19C, an exemplary elongate catheter-type device 280 is shown that is dimensioned for introduction through a working channel 282 of a gastroscope 283 for the thin layer ablation of irregular or pre-cancerous cell layers in the mucosal lining mu of an esophagus, such as in a treatment of Barrett's esophagus (see FIG. 19A). It should be appreciated that the working end could be used for skin resurfacing or any other thin layer ablation. For example, the catheter-type device 280 may be from about 2.0 mm. to 4.0 mm. in diameter. The working end 285 of the device is an insulator body 286 and carries a microchannel structure having a distal working surface 215 and electrode layer 225 substantially as described above (see FIGS. 19B-19D). Referring to FIG. 19D, it can further be seen that the microchannel structure carries paired, spaced apart electrode layers 235 and 245, the same as in the previous configuration of FIG. 12 without electron-emissive coating 252. The electrodes 235 and 245 are coupled to the electrical source 60 by leads 287a and 287b, respectively (FIG. 19B). The electrode layer 225 is coupled to the electrical source by lead 288. A simplified method of fabricating a microchannel structure for experimentation as shown in FIG. 19C (or FIG. 12) is to sandwich two MCP plates together as shown in more detail in FIG. 19D. The electrode layers 235 and 245 of the more proximal plate are coupled to the electrical source. Only the inner electrode 225 of the distal MCP is coupled to the electrical source thus providing an electrode layer-insulated and spaced apart from the working surface.

Figure 1B:
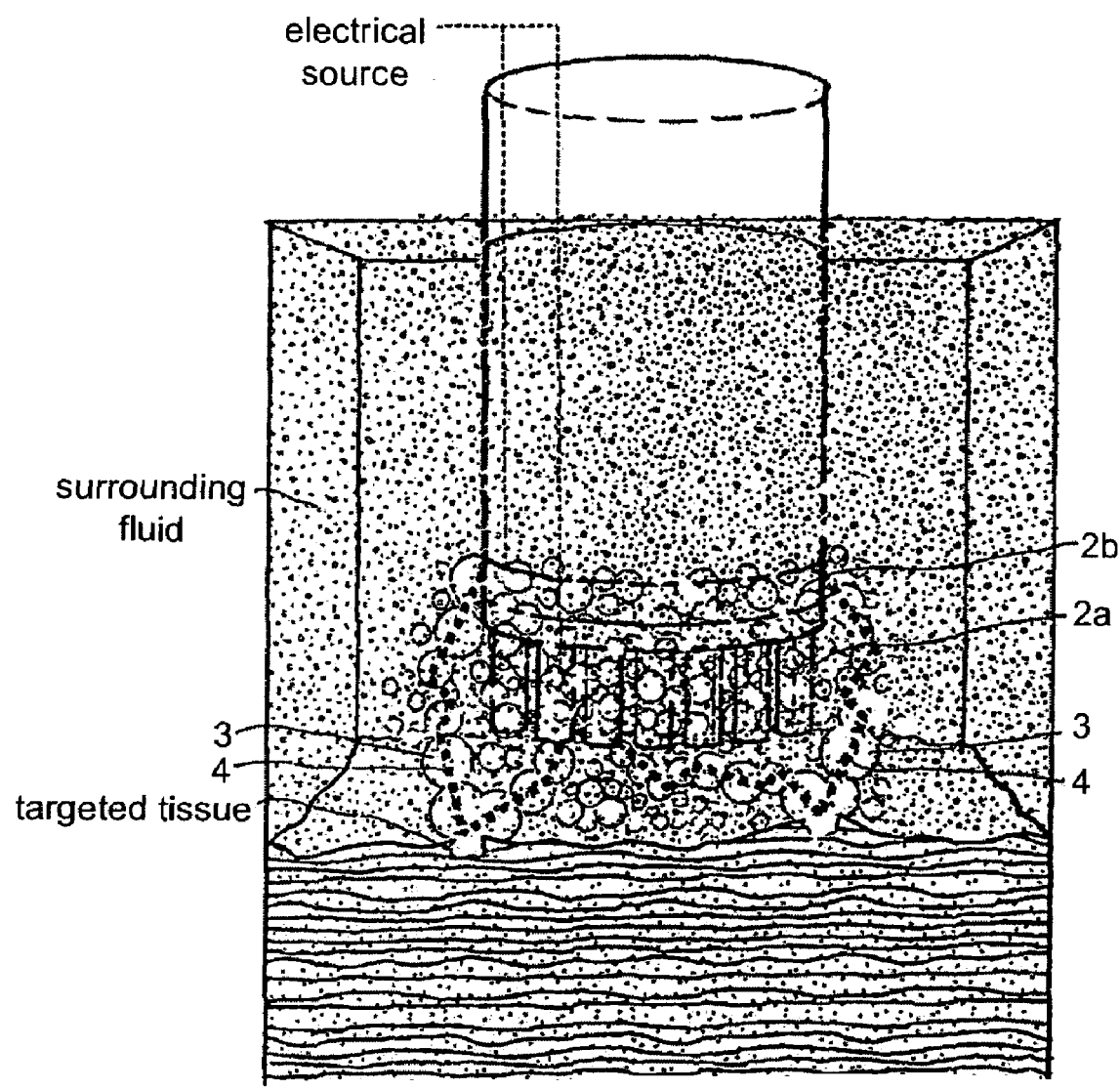
FIG. 1B is a view of a prior art working end of a bi-polar probe in relation to a tissue surface illustrating its the method of ablating tissue.
Figure 2:
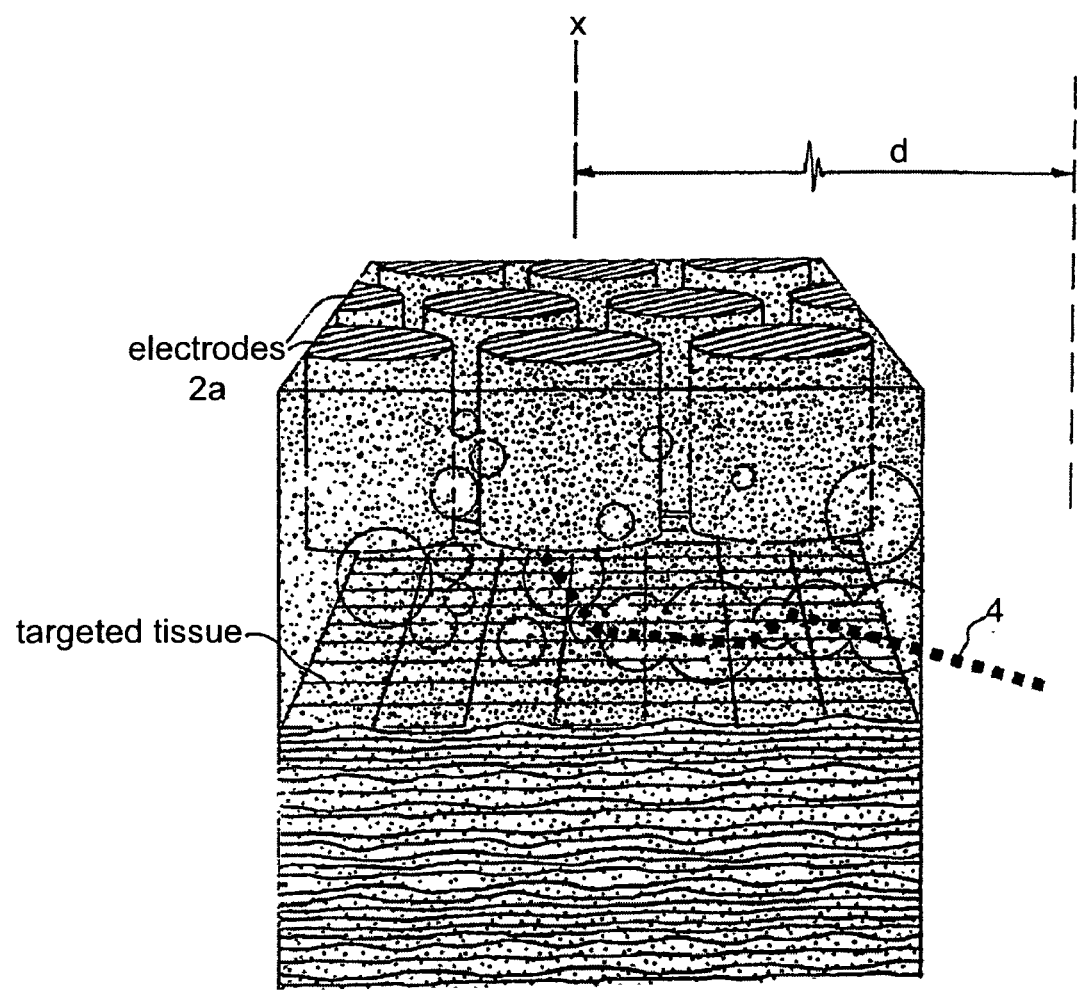
FIG. 2 is a sectional view of a portion of the prior art working end of FIG. 1B depicting the lack of localization of an energy application event.

In performing the method of the invention with the microchannel structure of FIGS. 19A-19C, the neutral gas media $m_2$ flows through the interior passageway 244 of the catheter body 268, as described in the previous embodiment. As can be understood in FIG. 19C, the flow of media $m_2$ through the microchannel structure displaces any surface fluids indicated at ml from the mucosa. Next, the neutral media $m_2$ is altered to a conductive or ionized media $m_2'$ by generating an intense electric field within the microchannel portions between the paired electrode layers 235 and 245 as depicted in FIG. 19D. In other words, field ionization means are utilized to ionize the gas volumes flowing within the microchannel structure. The ionized gas will thereafter remain conductive as it flows through the working surface 215 thus creating the conductive media volumes v, the same as depicted in FIGS. 15C-15E. The conductivity of the gas volumes v within and about the open microchannel terminations 222a-222z (cf. FIG. 1 SD) can thus be ionized and deionized in rapid intervals (as described above with photoionization) by rapid on/off modulation of the intense electric field (e.g., ranging from 200 to 5000 volts) between paired electrode layers 235 and 245 to achieve pulsed energy applications and micro-scale ablations as depicted in FIG. 15E. It is believed that by providing an independent means (first energy source at electrodes 235 and 245) for switching the media between conductive and non-conductive at a selected high repetition rate, the invention will provide precise control over the brief intervals in which the energy-tissue interactions eti occur, rather than the uncontrolled intervals which would occur if high intensity current were delivered to electrode layer 225 alone to cause random time intervals of ionization and electrical discharge across the gas volumes. As shown in FIG. 19A, the working end can be translated across the mucosal lining mu under endoscopic vision to ablate very thin cell layers substantially without collateral thermal damage to deeper tissue layers.

VI. Construction of Exemplary Type De "D" System for Plasma-Assisted Material Removal.

The previous sections described application of high intensity electrical energy to cause volumetric removal of tissue layers (i) in a pulsed high intensity mode for creating micron dimensioned discrete energy-tissue interactions to ablate tissue, or (ii) in the creation of a continuously sustained layer of high energy microplasmas about the working surface of the instrument to cause true plasma-mediated molecular volatilization of surface macromolecules to remove tissue volume. The Type "D" system described next functions almost identically to plasma-mediated system described previously, with the exception that the electrode arrangement of the working surface is adapted to insure that maximal average voltage is applied to the ionized gas volumes v continuously (cf FIG. 1 SD), rather than in intervals that vary with current frequency.

Figure 20:
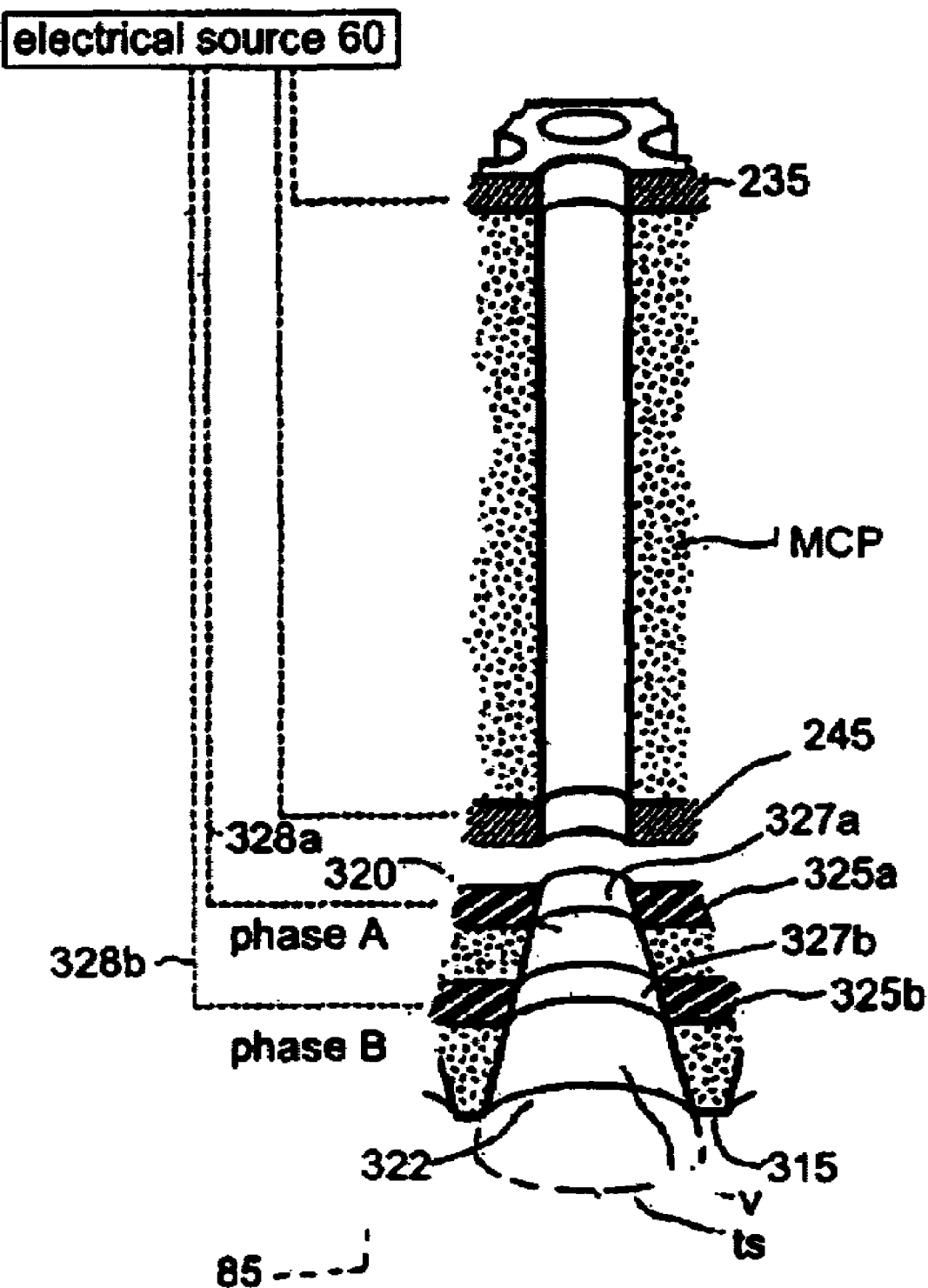
FIG. 20 is a cut-away view of a working surface of an exemplary Type "D" system which is similar to the Type "C" system except for the use of multiple out-of-phase electrodes to insure continuous high voltage energy delivery to a plasma for plasma mediated ablations.

A portion of the Type "D" working surface 315 and microchannel structure is shown in FIG. 20 with the novel electrode arrangement that comprises at least two spaced apart electrode layers 325a and 325b instead of one electrode layer (e.g., electrode layer 225 of the Type "C" embodiment of FIGS. 11-12). The scope of the invention includes anywhere from 2 to about 4 electrode layers and for clarity, the invention is described with two such electrode layers. FIG. 20 shows an exemplary working surface 315 and two electrode layers 325a and 325b with exposed surfaces 327a and 327b in the microchannels 320 (collectively). These two electrode layers are separate from the MCP electrode layers 235 and 245 that are the same as previously described. Each of the electrode layers 325a and 325b is coupled to the electrical source 60 and controller 45 by a separate lead 329a and 329b. Of particular interest, the electrical source 60 is capable of generating overlapping waveforms of the voltage delivered to each electrode layer 325a and 325b, by which in meant that the energy delivered to each electrode's frequency is out of phase with the other, depicted as Phase A and Phase B in FIG. 20. In a system with two such electrode layers 325a and 325b, the phase of the waveforms would be shifted by about ½ the frequency of the waveform; in a system with three such electrode layers 325a-325c (not shown) the phase of the waveforms would be shifted by about ⅓ the frequency, etc. An electrical source 60 can be adapted with circuitry known in the art to deliver such out-of-phase voltage waveforms to the spaced apart electrodes.

In general, it is postulated that such a system with spaced apart electrode layers 325a and 325b will cooperate with a return electrode 85 to maintain high voltage energy delivery to microplasma volumes v formed about the open distal terminations 322 of microchannels to insure a continuous high energy plasma for causing molecular volatilization of the surface molecules at the targeted site ts. In the operation of the previous Type "C" embodiment, the electric field between the electrode 225 and return electrode 85 would diminish in intensity depending of the voltage waveform as voltage difference between the active electrode 225 and the return electrode 85 varied. In this embodiment, an additional voltage differential would occur at certain intervals of the selected frequency between the out-of-phase voltages at the electrode layers 325a and 325b, in addition to the field created between these electrode layers and the return electrode 85. Thus, a method of the invention relating to the Type "D" system comprises (i) providing at least two closely spaced electrodes that have overlapping or out-of-phase voltage waveforms in an instrument working surface, in addition to a return electrode that cooperates with the working surface in contact with the targeted site ts or on the spaced apart portion of the instrument working end, (ii) creating and transiently capturing (by any suitable bubble creation means) a neutral gas volume that engages the at least two out-of-phase electrodes and further engages the targeted site ts; (iii) delivering intense energy to the electrode arrangement (e.g., in frequency range of about 250 kHz to 3.5 MHz) to sustainably ionized the transient gas volumes at high energy levels sufficient to cause volumetric removal of the surface layers of the targeted site ts.

Figure 21:
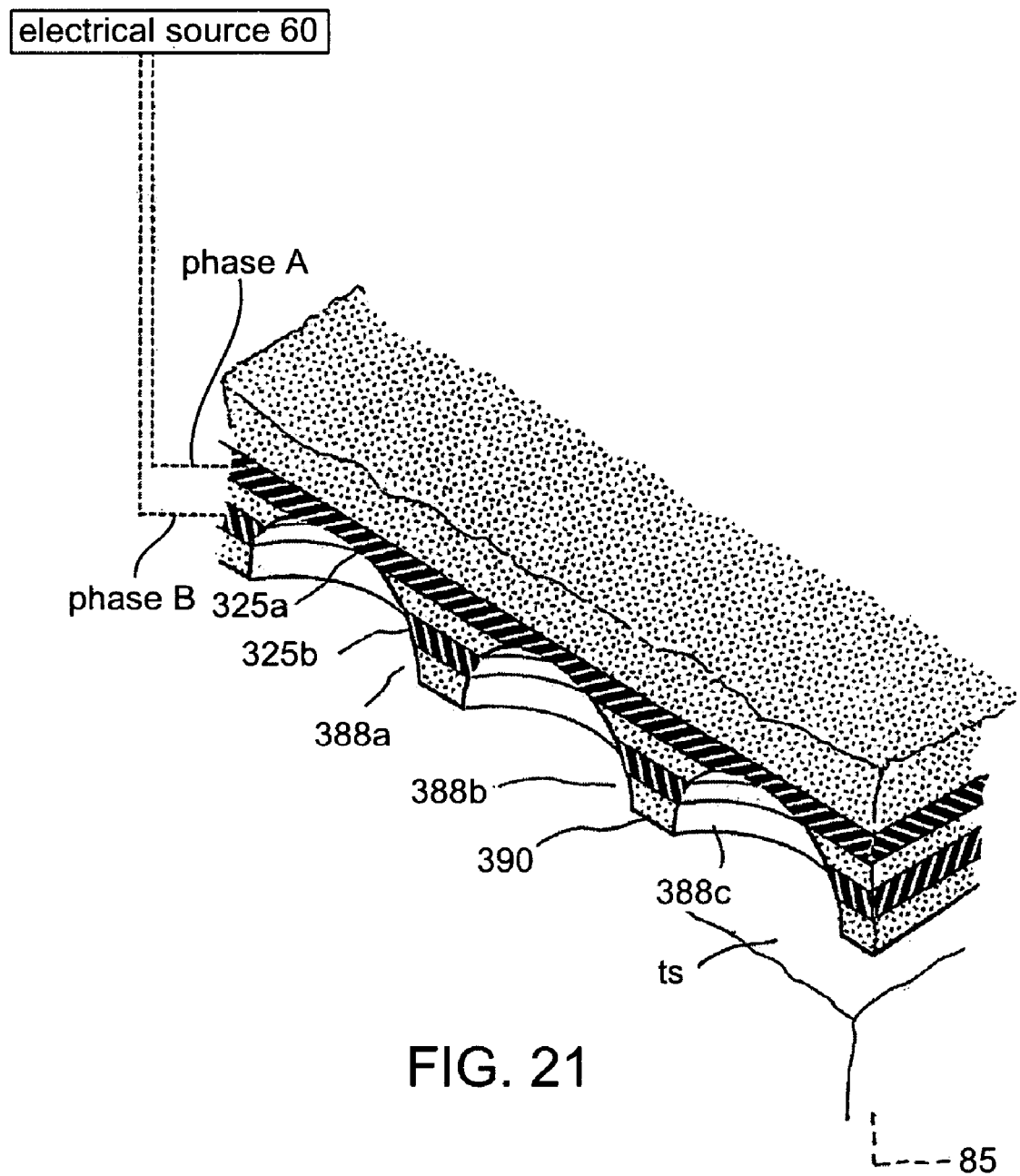
FIG. 21 is a sectional view of a working surface similar to that of FIG. 20 adapted for functioning without the neutral gas inflows through open-ended microchannels.

FIG. 21 generalizes the invention insofar as it relates to the utilization of multiple, closely spaced, overlapping phase electrodes 325a and 325b in a multiple adjacent recessed channel or chamber portions 388a-88c having the above-described micron dimensions in a working surface 390 that does not provide an independent means for introducing neutral gas volumes to the working surface. In other words, the invention may be used with high-intensity energy delivery (described above) to vaporize insulative bubbles from a fluid on, or within, the targeted tissue surface and to thereafter cause an intense energy discharge across the bubble to ablate tissue. The micron dimensions of the features of such a working surface 390 in combination with the out-of-phase energy applications to multiple electrodes provides a novel modality of tissue ablation, wherein the intensity of energy delivery across the expanding and collapsing bubbles is enhanced by the higher average voltages over a selected time interval to cause limited collateral thermal damage.

VII. Construction of Exemplary Type "E" System for Energy Application

Figure 22A:
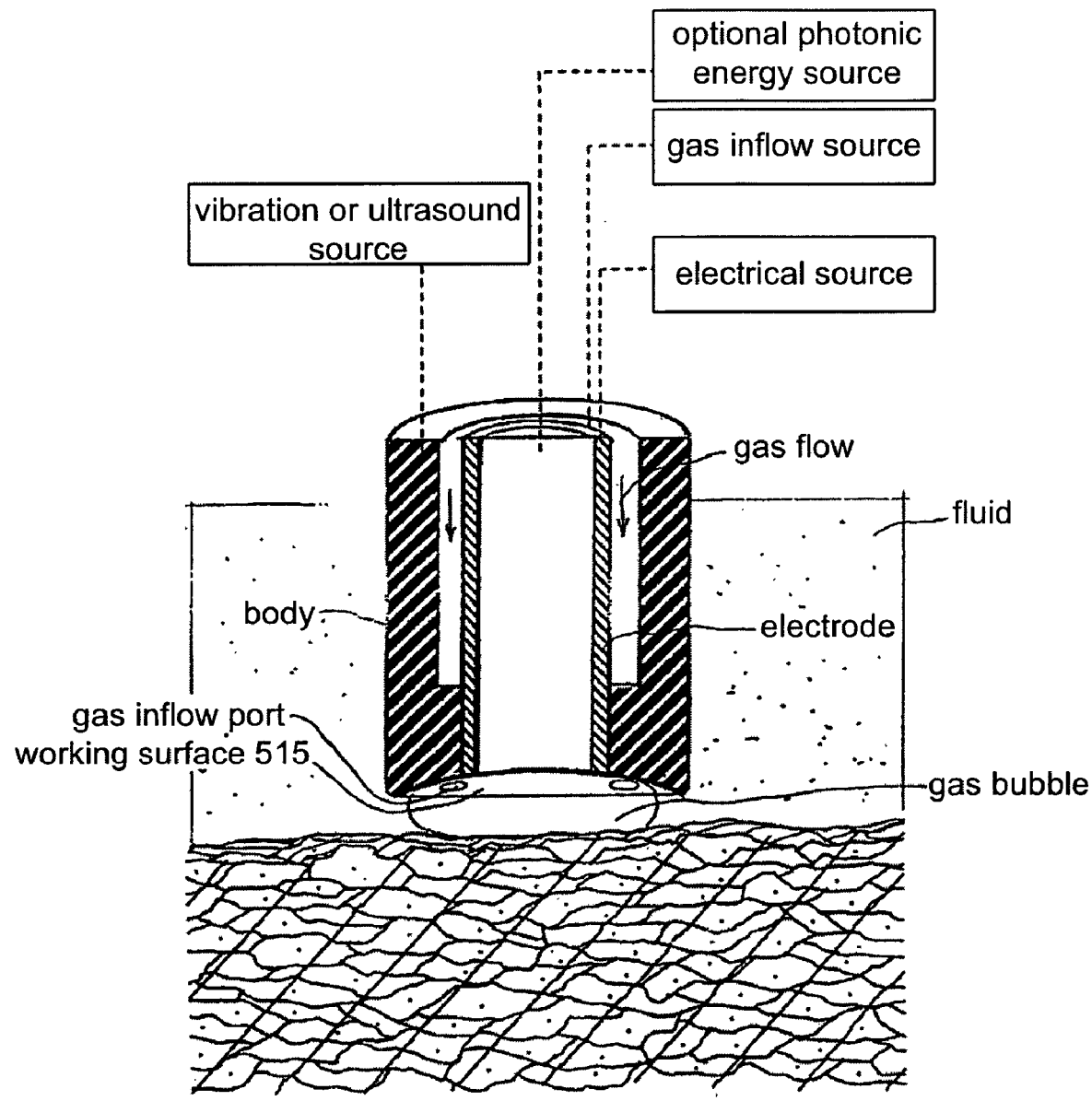
FIG. 22A is a sectional view of a working surface of a Type "E" system with the addition of a vibration source coupled to thereto.
Figure 22B:
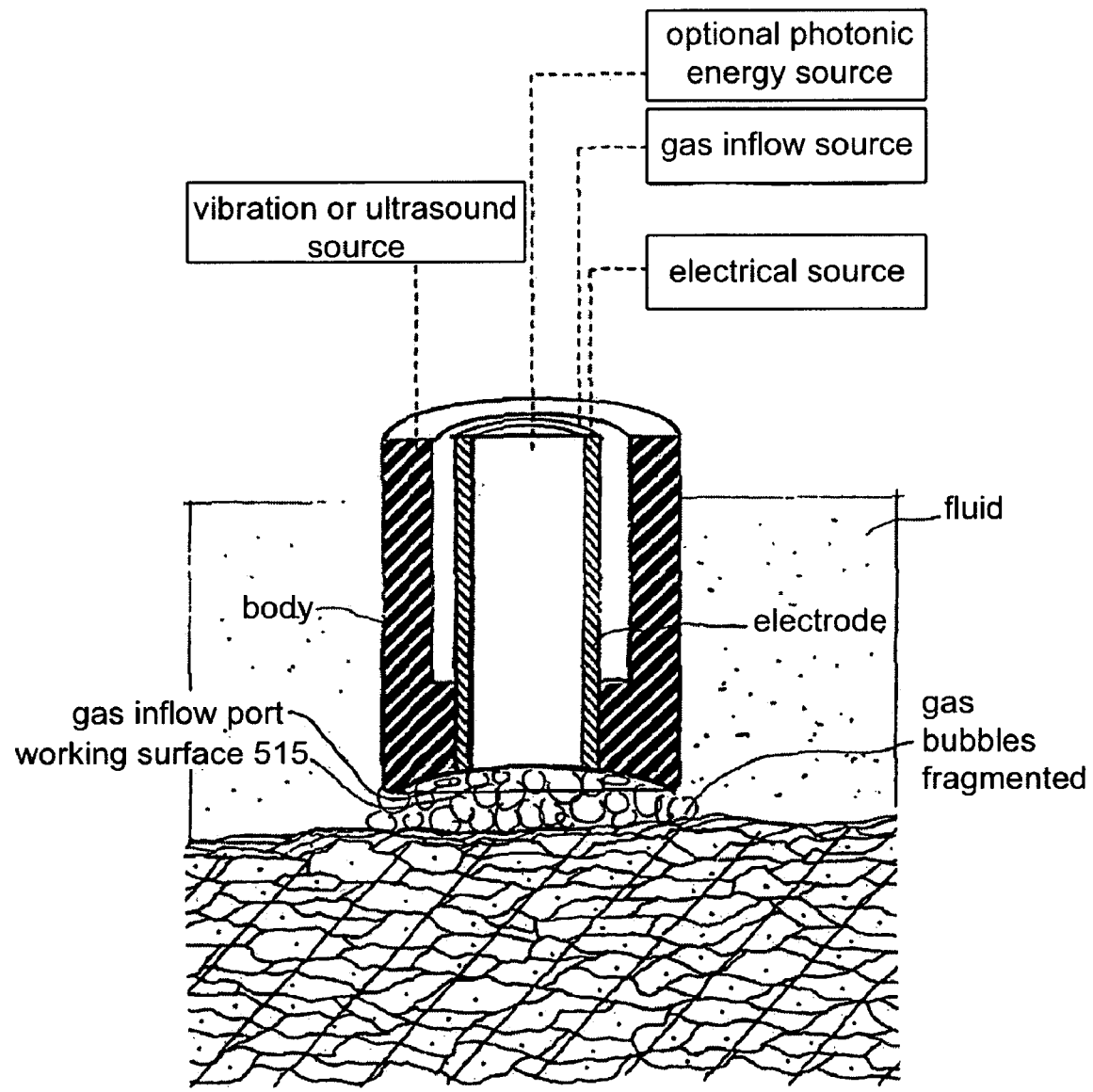
FIG. 22B is another sectional view of the working surface of FIG. 22A illustrating a method use.

FIGS. 22A-22B below illustrate a Type "E" embodiment 400 that provides an additional energy delivery mode that has been found to optimize the formation, character and dimension of gas bubbles in the interface between the working surface 415 and the targeted tissue.

More in particular, it has been found the application of vibrational energy to, and about, the working surface can increase the efficiency of the electrical energy application across the transient gas volume or bubbles that are formed between the working surface and the targeted tissue. In one embodiment referring to FIG. 22, the instrument body 410 extends to a working surface 415 that, for convenience shows a single media entrance channel 422 but a plurality of microchannel entrance ports are more practical for a typical dimension working end as shown in FIGS. 12, 13, 19C, 19C and 20. A remote source of a selected gas as described previously is operatively coupled to the instrument to provide flow through the at least one single media entrance channel 422 to the working surface.

The embodiment of FIG. 22A further shows that a vibration source 430 is operatively coupled to the instrument body 410. The scope of the invention includes any vibration source and preferably is any ultrasonic transducer known in the art that can couple acoustic energy to the instrument body 410. One type of ultrasonic transmission system can provide a proximal body portion (not shown) of the instrument (a transducer portion) that comprises at least one piezoelectric element together with opposing polarity electrodes coupled to each such element. The piezoelectric elements can be fabricated of a suitable material, e.g., lead zirconate-titanate, or any other piezoelectric material. In use, the piezoelectric elements convert an electrical signal into mechanical energy that results in a longitudinal vibratory motion in a shaft portion of the instrument body to deliver such energy to the working surface 415. Such an ultrasonic transmission unit is tuned acoustically as is known in the art to provide that the selected longitudinal vibration frequency that can be effective in vibrating the gas introduced through the at least one channel. In one embodiment, the gas is introduced through the working end surface through a plurality of channels having a cross-section of leas than about 1 micron. More preferably, the channels have a cross-section of less than about 0.5 microns. State another way, the channels preferably are of a selected dimension that is too small to allow inflow of fluid—but will still allow gas flow therethrough. Such a dimension will insure that a gas volume is trapped about the opening of each channel termination for energy delivery thereacross.

When the above described ultrasonic assembly is energized, a vibratory motion in the form of a standing wave is generated throughout the length of the instrument body 410. The propagation of such vibratory motion at particular points along the length of the instrument body 410 depends on the exact longitudinal location at which the vibratory motion is measured. A minimum in the vibratory motion or standing wave is commonly referred to as a node, wherein motion is at minimal level. The location at which the vibratory motion reaches a peak in the standing wave is referred to as an anti-node, and the length of the instrument body 410 is selected to provide an anti-node characteristics generally at the working surface 415 to deliver a maximum amount of energy thereto. Any suitable electrical source and controller can be coupled to the piezoelectric elements to drive or excite the ultrasonic assembly at any suitable resonant frequency of the tuned acoustic assembly.

In operation, the piezoelectric elements are energized in response to an electrical signal provided by source to thereby produce an acoustic standing wave in the instrument body contemporaneous with the introduction of a selected gas to the working surface (see FIG. 22A-22B). The delivery of the acoustic energy alters the characteristic of the gas volume transiently captured between the working surface and the targeted tissue. The acoustic energy application has been found to be useful for lowering the power or voltage requirements to apply ablative energy across the gas interface between working surface 415 and the targeted tissue, for example in the fluid environment of FIGS. 22A-22B. Without wishing to be limited to any particular theory to explain the reasons for the increases effectiveness of the energy application, it is believed that the acoustic energy alters or diminishes the surface tension of the gas volume(s) or bubbles in the fluid environment, fragments the gas bubble(s) into smaller dimensions, detaches the gas bubbles from the working surface, or in general, very rapidly creates a more refined gas volume between the working surface and the targeted tissue. By this means, the voltage required to cause an ablative electrical discharge across the introduced gas is lessened.

The vibrational or acoustic energy as described above can be applied in a continuous manner to the working end, or it can be applied in a pulsed manner. The scope of the invention includes the use of such vibrational energy in any electrosurgical working end that is adapted to apply energy to tissue, and in particular to such instruments that are adapted to apply energy for purposes of ablation or volumetric removal as described above. The types of instrument working ends that fall within the scope of the invention includes, but is not limited to, probe working ends for applying energy to tissue in procedures in orthopedics, endovascular interventions, neurointerventions, ENT, urology and general surgery. The invention also may be used in the jaws of grasping-type instruments. The vibrational energy can be combined with the instruments described above that use photoionization of the gas volume, or the vibrational energy can be used independently thereof—still in combination with the electrical energy application components described above.

Figure 23:
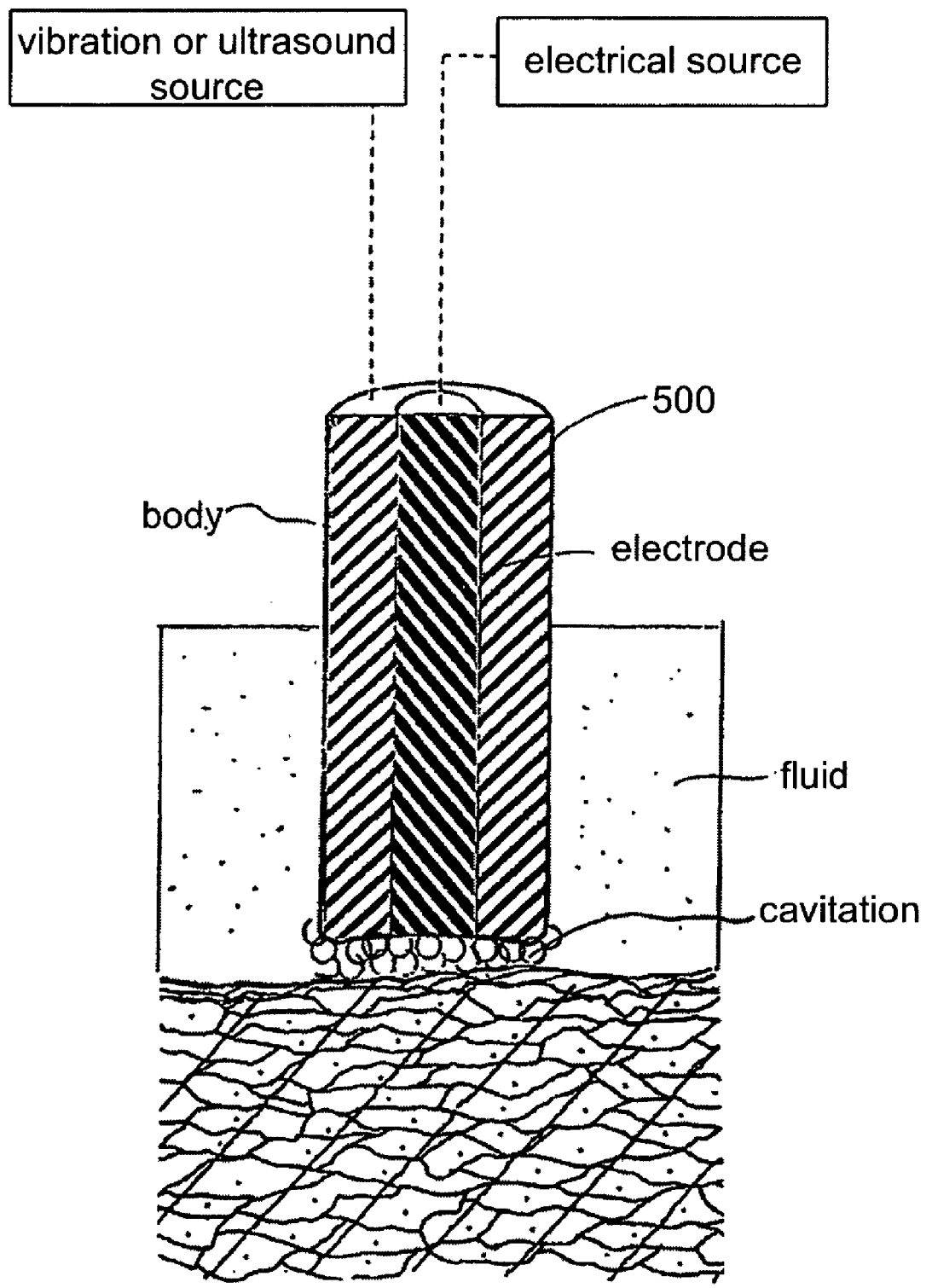
FIG. 23 is a sectional view of a working surface of another Type "E" system that uses ultrasonic energy to create cavitation that cooperates with electrical energy application to the targeted tissue.

In another embodiment shown in FIG. 23, the probe working end 500 can use ultrasound energy at the working surface 515 to create cavitation bubbles to provide an interface between the working surface and the targeted tissue. Such cavitation bubbles can causes by an intense energy application of energy to a targeted media. When absorption of energy by the target media results in thermoelastic expansion of the target and a rise in internal pressures within the target. The term stress confinement refers to the process of causing an increase in pressure within a targeted media before the pressure can dissipate from the target at the speed of sound. When there exists a defined or free boundary between the targeted media and different surrounding media—such as a liquid or gas interface with the target—the target expands at its surface and then snaps back. The expansion phase is positive pressure or stress and the snap-back is negative stress. When the negative stress exceeds the strength of target media, that media breaks, disintegrates or ejects a surface portion thereof. For example, an intense energy application whether from an electrical source, laser source or acoustic (mechanical) source can induce from 100° to 1000° C. temperature rises in a targeted composition and thereby can cause transient pressures of from 100-1000 atmospheres to explode the targeted composition. The same process of energy deposition in a targeted media can cause the formation of a bipolar positive/negative stress wave that propagates into surrounding media. If the surrounding media were a substantially solid material, the stress wave causes a fracture or break in the material called a spall plane. If the surrounding media were a liquid or a soft tissue, the bi-polar positive/negative stress wave would create cavitation bubbles in the media. In a liquid such as water, when absorbing energy in an intense manner, even a slight 5° to 20° C. temperature rise within a nanosecond or microsecond energy application interval can yield a ±10 atm (atmosphere) bipolar stress wave— and the −10 atm negative stress can cause cavitation in water. Thus, the invention can use ultrasound energy as is known in the art to create such cavitation bubbles (either in a continuous mode or pulsed mode).

The scope of the invention includes the application of acoustic energy to create cavitation bubbles in a fluid media about the working surface of the probe. Thereafter, the invention includes the application of electrical energy across the environment of expanding and collapsing cavitation bubbles to ablate tissue. This type of probe does not need a gas inflow source of the previous embodiments, since the acoustic cavitation system provides the desired interface between the working surface 515 and the targeted tissue. This type of working end can be used with or without the photoionization method and apparatus described in previous embodiments.

While the plasma-assisted energy delivery methods above have been described in connection with several surgical procedures for volumetric tissue removal such as skin resurfacing, the ablation of pre-cancerous or malignant cell layers and in spine surgery, it will be clear to those having skill in the art that the system has operational characteristics that may be suitable for a wide range of volumetric tissue removal procedures in, or on, structure of a patient's body. The system and method of the invention are suitable for other arthroscopic surgeries, including partial meniscectomies, synovectomies, chondroplasties, tendon and cartilage removals, and in general resurfacing and texturing of cartilage, tendon and bone surfaces. In addition, in the ENT and GI fields, there are a variety of procedures that require volumetric tissue removal either at a tissue surface or at the end of a probe inserted percutaneously in treating nose and throat disorders, for example, soft palate volume reduction surgery, turbinate reduction surgery and jaw bone surgery. These procedures require that the surgeon be provided with means to remove tissue in close proximity to delicate structures and nerves that cannot be damaged, which procedures lend themselves to the methods disclosed herein. In many fields, the selective removal of malignant tissue or other tumors may be accomplished by the present invention. For example, a form of stereotactic-directed probe may be used to ablate breast lesions. The method of the invention also may have use in interventional cardiology to remove vascular occlusions. The method of the invention also may be useful for drilling holes in tissue such as in TMR procedures (transmyocardial revascularization). The material removal methods described above apply to all body structures, which include non-anatomic structures such as accretions, calculi and the like.

Those skilled in the art will appreciate that the exemplary embodiments and descriptions thereof are merely illustrative of the invention as a whole, and that variations in controlling the duration of intervals of energy delivery, in controlling the repetition rate, and in controlling the voltage applied to create the interval of intense electric fields may be made within the spirit and scope of the invention. Accordingly, the present invention is not limited to the specific embodiments described herein, but includes the features disclosed in the author's co-pending applications listed in the Section above titled "CROSS-REFERENCE TO RELATED APPLICATIONS" and the invention is defined by the scope of the appended claims. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A method for modifying tissue, comprising the steps of:
    positioning an instrument working end in a fluid immersed site proximate to targeted tissue wherein the working end includes at least one electrode;
    applying vibrational energy to the working end thereby creating at least one bubble in the fluid; and
    applying electrical energy from said at least one electrode across said at least one bubble to thereby modify the targeted tissue.

2. The method of claim 1, wherein said vibrational energy comprises ultrasonic vibration.

3. The method of claim 1, further including introducing a gas through at least one outlet in the working end.

4. A medical device for delivering energy to targeted tissue, comprising:
    a member defining a distal working surface;
    at least one electrode element carried in said working surface; and
    a vibration source coupled to said working surface wherein the working surface is configured to generate a cavitation bubble in a fluid contacting the working surface when the member is energized by the vibration source to create a standing wave in the member.

5. The medical device of claim 4, wherein the vibration source is an ultrasonic source.

6. The medical device of claim 4, wherein the member includes a tuned acoustic transmission assembly.

7. The medical device of claim 4, further comprising at least one channel with an open distal termination in said working surface.

8. The medical device of claim 7, further comprising a gas source coupled to the at least one channel.

9. The medical device of claim 4, further comprising a light energy channel with a distal termination in the working surface.

10. The medical device of claim 7, wherein said at least one channel has an open distal termination with a cross-sectional dimension less than 1 μm.

11. The medical device of claim 7, wherein said at least one channel has an open distal termination with a cross-sectional dimension less than 0.5 μm.

12. The medical device of claim 7, wherein said at least one channel defines a cross-sectional dimension that prevents fluid flows therethrough.

13. The medical device of claim 12, wherein said at least one channel defines a cross-sectional dimension that allows gas flows therethrough.

14. The medical device of claim 4, wherein the working surface includes at least one concavity.

15. The medical device of claim 4, wherein the working surface includes an electrode coupled to a first pole of an electrical source.

16. The medical device of claim 4, wherein the working surface includes first and second electrodes coupled to first and second opposing poles of an electrical source.

17. The medical device of claim 4, wherein the member has a length configured to produce an anti-node characteristic at the working surface.

* * * * *